United States Patent
Liu et al.

(10) Patent No.: US 11,535,633 B2
(45) Date of Patent: Dec. 27, 2022

(54) FUSED TRICYCLIC HETEROCYCLE COMPOUNDS AND THERAPEUTIC USES THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Dong Liu, Basking Ridge, NJ (US); Lei Chen, Basking Ridge, NJ (US); Linghang Zhuang, Chalfont, PA (US); Puhui Li, Plainsboro, NJ (US); Xinzhu Zhang, Franklin Park, NJ (US); Chunying Song, Newtown, PA (US); Matthew Miller, Branchburg, NJ (US); Qiyue Hu, Shanghai (CN); Yuna Yan, Shanghai (CN); Feng He, Shanghai (CN); Weikang Tao, North Brunswick, NJ (US)

(73) Assignees: Jiangsu Hengrui Medicine Co., Ltd., Lianyungang (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 17/255,712

(22) PCT Filed: Jun. 28, 2019

(86) PCT No.: PCT/US2019/039860
§ 371 (c)(1),
(2) Date: Dec. 23, 2020

(87) PCT Pub. No.: WO2020/006432
PCT Pub. Date: Jan. 2, 2020

(65) Prior Publication Data
US 2021/0300944 A1    Sep. 30, 2021

Related U.S. Application Data

(60) Provisional application No. 62/691,208, filed on Jun. 28, 2018.

(51) Int. Cl.
| | | |
|---|---|---|
| C07D 498/06 | (2006.01) | |
| A61K 31/5365 | (2006.01) | |
| A61K 31/5383 | (2006.01) | |
| A61P 29/00 | (2006.01) | |
| A61P 31/12 | (2006.01) | |
| A61P 31/18 | (2006.01) | |
| A61P 35/00 | (2006.01) | |
| C07D 487/06 | (2006.01) | |

(52) U.S. Cl.
CPC ......... *C07D 498/06* (2013.01); *C07D 487/06* (2013.01)

(58) Field of Classification Search
CPC .............. C07D 498/06; A61K 31/5365; A61K 31/5383; A61P 29/00; A61P 31/12; A61P 31/18; A61P 35/00
See application file for complete search history.

(56) References Cited

U.S. PATENT DOCUMENTS

| | | | |
|---|---|---|---|
| 6,548,494 B1 | 4/2003 | Webber et al. | |
| 2002/0016098 A1 | 2/2002 | Poh et al. | |
| 2002/0160984 A1 | 10/2002 | Li et al. | |
| 2008/0318999 A1 | 12/2008 | Isaac et al. | |

FOREIGN PATENT DOCUMENTS

| | | |
|---|---|---|
| WO | 2010017248 A2 | 2/2010 |
| WO | 2013166000 A1 | 11/2013 |
| WO | 2017175147 A1 | 10/2017 |
| WO | 2017175156 A1 | 10/2017 |

OTHER PUBLICATIONS

Shanker A. and Marincola F., Cancer Immunol. Immunother., 2011, 60: 1061-1074.
Medzhitov, R. J. Immunol. 2013, 191, 4473-4474.
Matzinger, P., Science 2002, 296: 301-305.
Ng KW., et al., Trends in Immunology, 2018, 39: 44-54.
Ahn J. and Barber G., Current Opinion in Immunology 2014, 31:121-126.
Woo S et al., Immunity, 2014, 41:830-842.
Corrales et al., Cell Reports, 2015, 11:1018-1030.
Corrales L. and Gajewski F., Clin. Cancer Res., 2015, 21: 4774-4779.
Zitvogel L. et al., Nature Reviews Immunology, 2015, 15: 405-414.
Parker B. et al., Nat Rev Cancer, 2016, 16:131-144.
Francica B. et al., Cancer Immunol Res., 2018, 6: 1-12.

*Primary Examiner* — Brenda L Coleman
(74) *Attorney, Agent, or Firm* — Fox Rothschild LLP

(57) ABSTRACT

This application discloses a new class of fused tricyclic heterocycles of formula (I), preparation methods thereof, pharmaceutical compositions comprising these compounds, and pharmaceutically acceptable salts, solvates, or prodrugs thereof, and their uses for the treatment of diseases in which modulation of STING is beneficial, for example, cancers, pre-cancerous disorders, and viral infections.

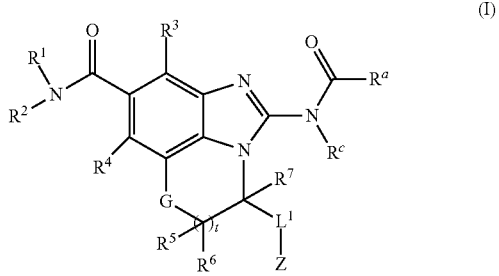

33 Claims, No Drawings

FUSED TRICYCLIC HETEROCYCLE COMPOUNDS AND THERAPEUTIC USES THEREOF

CROSS-REFERENCE TO RELATED APPLICATIONS

This application is a U.S. national phase application of International Application No. PCT/US2019/039860, filed on Jun. 28, 2019, which claims priority under 35 U.S.C. § 119(e) to U.S. Provisional Patent Application No. 62/691,208, filed on 28 Jun. 2018, the disclosures of which are incorporated herein by reference in their entirety.

FIELD OF THE INVENTION

The present invention relates to fused tricyclic heterocycles as agonists of the stimulator of interferon genes (STING), and preparation methods, pharmaceutical compositions, and medical uses thereof for the treatment of diseases in which modulation of STING is beneficial, for example, cancer, pre-cancerous disorders, hepatitis B virus (HBV), hepatitis C virus (HCV), influenza, human immunodeficiency virus infection, AIDS, inflammation, and infectious diseases, or use as immunogenic composition or vaccine adjuvants.

BACKGROUND OF THE INVENTION

Vertebrates defend against microorganisms or respond to signals from cellular or tissue damage by innate and adaptive immunity. Innate immunity has no antigen specificity and executes the defense mechanisms immediately after an antigen's appearance in the body. Adaptive immunity requires time to generate a full response, but is antigen-specific and long lasting. Once an antigen has been processed and recognized, the adaptive immune system utilizes a set of immune cells specifically designed to attack that antigen. During the course of an adaptive immune response, memory immune cells are generated which allow for a more rapid and effective response to re-exposure to antigens. The innate immune system is required to activate our adaptive immune system. Numerous molecules and cells involved in innate immunity and adaptive immunity function cooperatively (Shanker A. and Marincola F, *Cancer Immunol. Immunother.*, 2011, 60: 1061-1074).

Innate immunity is initiated when the pathogen-associated molecular patterns (PAMPs) present in pathogens are recognized by pattern recognition receptors (PRRs) (Medzhitov, R. *J. Immunol.* 2013, 191, 4473-4474). Some endogenous damage-associated molecular patterns (DAMPs), including various tumor-derived antigens can also be recognized by these PRRs as well (Matzinger, P., *Science* 2002, 296: 301-305). The free cytosolic DNA from pathogens and abnormal cells can be recognized by DNA sensors. cGAS (cyclic GMP-AMP Synthase) has been shown to be an important DNA sensor and catalyzes free cytosolic DNA into cyclic di-nucleotides (CDN) 2'3'-GAMP (Ng K W, et al, *Trends in Immunology,* 2018, 39: 44-54).

Stimulator of interferon genes (STING; also known as MITA and MPYS, and encoded by TMEM173) is a signaling molecule associated with the endoplasmic reticulum (ER). Upon binding to the cyclic dinucleotides (CDNs) generated by cGAS as well as bacterial cyclic di-AMP (c-di-AMP) or c-di-GMP in the cytosol, STING undergoes a conformational change and forms a complex with TBK1. This complex translocates from the ER to the perinuclear golgi and then phosphorylates IRF3, which dimerizes and enters the nucleus to initiate the transcription of type I IFNs. TBK1 also phosphorylates residues on the protein IκB, leading to its degradation, which causes the activation and translocation of NF-κB to the nucleus and transcription of pro-inflammatory cytokines such as TNFα, IL-6 and IL-1β (Ahn J. and Barber G., *Current Opinion in Immunology* 2014, 31:121-126). Accumulating evidence indicates that STING-dependent signaling is critical in promoting antitumor immunity. STING deficient mice have decreased tumor rejection observed when compared with wild type mice (Woo S. et al, *Immunity,* 2014, 41:830-842). Activation of STING significantly suppressed the growth of multiple types of mouse tumor (Corrales et al., *Cell Reports,* 2015, 11:1018-1030).

The antitumor activity mediated by STING is at least partially via type I IFNs (Corrales L. and Gajewski F, *Clin. Cancer Res.,* 2015, 21: 4774-4779). The effect of type I IFNs (IFNα/β) on immune cells has been well established. Upon binding to IFNα/β, the IFNα/β receptor activates a cascade of events and induces the transcription of a wide variety of genes regulated by IFN-stimulated response elements (ISRE), thus modulating multiple types of immune cells. In particular, type I IFNs promote cross-priming, boost effector T cell function and expansion, mediate memory development, thereby coupling innate immunity with adaptive immunity (Zitvogel L. et al, *Nature Reviews Immunology,* 2015, 15: 405-414). Type I IFNs contribute to antitumor immunity in various types of cancer (Parker B. et al., *Nat Rev Cancer,* 2016, 16:131-144). TNFα may be another important contributor to the therapeutic effect observed with the activation of STING (Francica B. et al., *Cancer Immunol Res.,* 2018, 6: 1-12).

The patent applications disclosing STING modulators include WO2010017248, WO2013166000, WO2017175147 and WO2017175156.

In summary, STING activation may have significant impact on innate and adaptive immune response and accordingly may have a beneficial impact on the treatment of cancer and other diseases such as viral infection.

SUMMARY OF THE INVENTION

The present invention provides a new class of fused tricyclic heterocycle compounds as represented by formula (I) below useful as STING agonists and as therapeutic agents for the treatment of diseases in which modulation of STING is beneficial, for example, cancer, pre-cancerous disorders, hepatitis B virus (HBV), hepatitis C virus (HCV), influenza, human immunodeficiency virus infection, AIDS, inflammation, and other infectious diseases. These compounds can also be used as immunogenic composition or vaccine adjuvants.

Thus, in one aspect, the present invention provides a compound of formula (I), or a tautomer, or a pharmaceutically acceptable salt, prodrug, or solvate thereof:

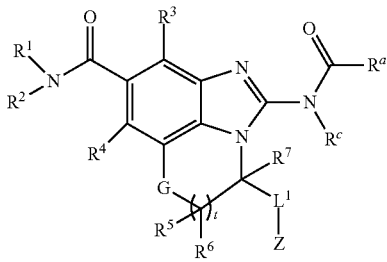

wherein:

R$^a$ is selected from the group consisting of alkyl, alkenyl, alkynyl, haloalkyl, and hydroxyalkyl, wherein the alkyl, alkenyl or alkynyl is unsubstituted or substituted with one or more, preferably one to five, and sometimes more preferably one to three, substituents selected from the group consisting of halogen, alkyl, alkoxy, haloalkyl, amino, nitro, cyano, hydroxy, hydroxyalkyl, carboxylic acid, cycloalkyl, heterocyclyl, aryl and heteroaryl;

or R$^a$ is

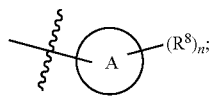

ring A is selected from the group consisting of cycloalkyl, heterocyclyl, aryl and heteroaryl;

G is O or NR$^b$;

R$^b$ is selected from the group consisting of hydrogen, alkyl, alkenyl, alkynyl alkoxy, alkoxyalkyl and haloalkyl; wherein the alkyl, alkenyl, alkynyl, alkoxy or alkoxyalkyl is unsubstituted or substituted with one or more, preferably one to five, and sometimes more preferably one to three, substituents selected from the group consisting of halogen, alkyl, alkoxy, haloalkyl, amino, cyano, hydroxy, hydroxyalkyl, carboxylic acid, cycloalkyl, heterocyclyl, aryl and heteroaryl;

R$^c$ is selected from the group consisting of hydrogen, alkyl, haloalkyl, alkenyl and alkynyl;

R$^1$ and R$^2$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, cyano, hydroxy, hydroxyalkyl, cycloalkyl, heterocyclyl, aryl and heteroaryl;

R$^3$ and R$^4$ are each independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

R$^5$, R$^6$ and R$^7$ are each independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

L$^1$ is selected from the group consisting of alkylene, alkenylene, NH, —(CH$_2$)$_s$NH—, —(CH$_2$)$_s$NH(CH$_2$)$_r$—, O, S(O)$_m$, C(O), —C(O)NH—, —NHC(O)—, and —HNC(O)NH—, wherein the alkylene or alkenylene is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, oxo, —C(O)OR$^{18}$, R$^{19}$, cycloalkyl, heterocyclyl, aryl and heteroaryl; two substitutes on the same carbon can form a cycloalkyl or heterocyclyl ring; two substitutes on adjacent carbons can form a cycloalkyl, heterocyclyl, aryl and heteroaryl ring;

or L$^1$ is absent;

Z is selected from the group consisting of —C(O)O-benzyl, butyloxy carbonyl, hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, —NR$^9$R$^{10}$, oxo, —C(O)OR$^{18}$, R$^{19}$, cycloalkyl, heterocyclyl, aryl and heteroaryl;

or Z is formula (Za) or a tautomer thereof:

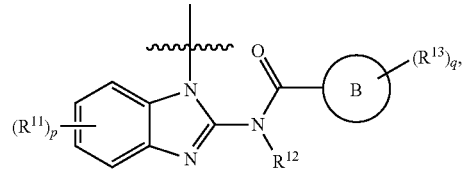

wherein ring B is selected from the group consisting of cycloalkyl, heterocyclyl, aryl and heteroaryl;

R$^8$ at each occurrence is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

R$^9$ and R$^{10}$ are identical or different, and each is independently selected from the group consisting of hydrogen, alkyl, —C(O)O-benzyl, haloalkyl, cycloalkyl, heterocyclyl, aryl and heteroaryl;

R$^{11}$ at each occurrence is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl; wherein the alkyl or alkoxy is unsubstituted or substituted with one or more, preferably one to five, and sometimes more preferably one to three, substituents selected from the group consisting of halogen, alkyl, alkoxy, alkenyl, alkynyl haloalkyl, amino, nitro, hydroxy, hydroxyalkyl, cyano, —O—P(O)(OH)$_2$, cycloalkyl, heterocyclyl and NR$^{16}$R$^{17}$;

R$^{12}$ is selected from the group consisting of hydrogen, alkyl, alkenyl and alkynyl;

R$^{13}$ at each occurrence is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^{14}$ and $R^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, hydroxy, cyano, nitro, alkyl, alkoxy, cycloalkyl, heterocyclyl, aryl and heteroaryl;

$R^{16}$ and $R^{17}$ are identical or different, and each is independently selected from hydrogen or alkyl;

or, $R^{16}$ and $R^{17}$ together with the nitrogen atom to which they are attached form a heterocyclyl, wherein the heterocyclyl contains one or two identical or different heteroatoms selected from the group consisting of N, O and S, and the heterocyclyl is optionally substituted by one or more, preferably one to five, and sometimes more preferably one to three, substituents selected from the group consisting of alkyl, alkoxy, halogen, amino, cyano, nitro, hydroxy and hydroxyalkyl;

$R^{18}$ is hydrogen or alkyl;

$R^{19}$ is cycloalkyl, heterocyclyl, aryl or heteroaryl, wherein the cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl and cyano;

n is 0, 1, 2, 3 or 4;
m is 0, 1 or 2;
s is integer of 1 to 6;
r is 1, 2, 3 or 4;

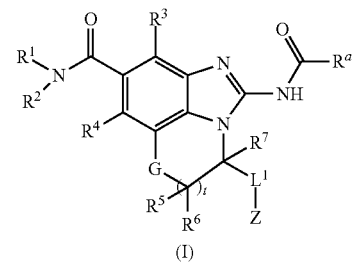

(I)

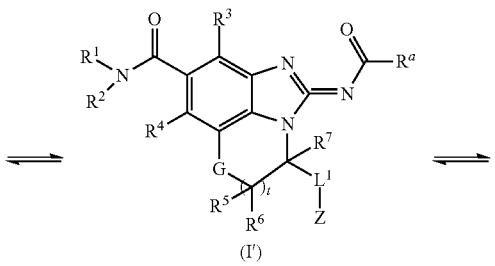

(I')

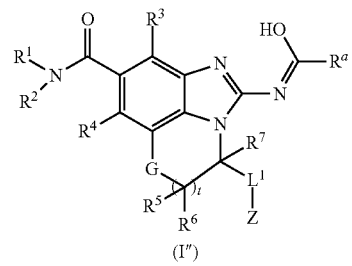

(I")

t is 1, 2, 3 or 4;
p is 0, 1, 2, 3 or 4; and
q is 0, 1, 2, 3 or 4.

In another aspect, the present invention provides a pharmaceutical composition, comprising a compound of formula (I), in any embodiment disclosed herein, or a tautomer, or a pharmaceutically acceptable salt, solvate, or prodrug thereof, and one or more pharmaceutically acceptable carriers, diluents, or other excipients.

In another aspect, the present invention provides a method of treating a STING-mediated disease or disorder, comprising administering to a subject in need thereof a therapeutically effective amount of a compound of formula (I), in any embodiment disclosed herein, or a tautomer, a pharmaceutically acceptable salt, solvate, prodrug, or composition thereof, In another aspect, the present invention provides use of a compound of formula (I), in any embodiment disclosed herein, or a tautomer, a pharmaceutically acceptable salt, solvate, or prodrug thereof, in the manufacture of a medicament for the treatment of a STING-mediated disease or disorder.

The STING-mediated disease or disorder includes, but is not limited to various cancers, a pre-cancerous syndromes, and viral infections, e.g., hepatitis B virus (HBV), hepatitis C virus (HCV), influenza, human immunodeficiency virus infection, AIDS, inflammation, infectious diseases or the like.

Other aspects and benefits of the present invention will be better understood through the detailed description, Examples, and claims.

DETAILED DESCRIPTION OF THE INVENTION

The present invention, in one aspect, provides a compound of formula (I), or a tautomer, or a pharmaceutically acceptable salt, prodrug, or solvate thereof, as defined above:

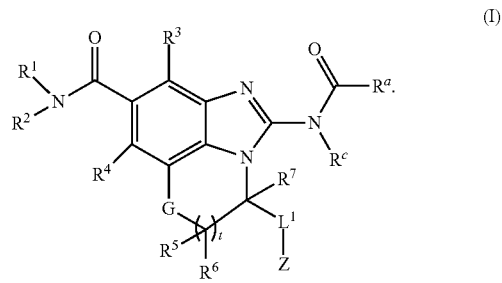

(I)

For illustration purpose, when $R^c$ is hydrogen, the compound may exist in any of the tautomer forms (I), (I'), or (I"), or a mixture thereof, all of which are encompassed by the present invention.

wherein: $R^a$, $L^1$, Z and $R^1$ to $R^7$ each as defined in formula (I).

In one embodiment, $L^1$ is a bond, and the compound of formula (I) is further characterized by formula (II):

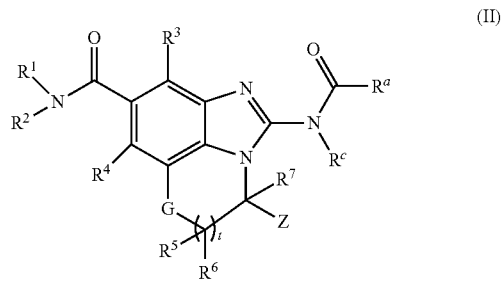

(II)

or a tautomer, or a pharmaceutically acceptable salt, solvate, or prodrug thereof;

wherein:

Z is selected from the group consisting of hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, oxo, —C(O)OR$^{18}$, R$^{19}$, —NHC(O)O-benzyl, cycloalkyl, heterocyclyl, aryl and heteroaryl;

G, R$^{18}$, R$^{19}$, t, R$^a$, R$^c$ and R$^1$ to R$^7$ are each as defined in formula (I).

In another embodiment, the compound of formula (I) is further characterized by formula (III):

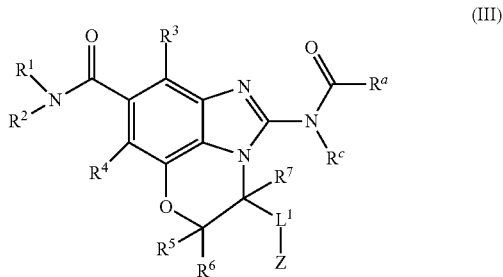

(III)

wherein:

R$^a$ is selected from the group consisting of alkyl, alkenyl, alkynyl, haloalkyl, and hydroxyalkyl, wherein the alkyl, alkenyl or alkynyl is unsubstituted or substituted with one or more, preferably one to five, and sometimes more preferably one to three, substituents selected from the group consisting of halogen, alkyl, alkoxy, haloalkyl, amino, nitro, cyano, hydroxy, hydroxyalkyl, carboxylic acid, cycloalkyl, heterocyclyl, aryl and heteroaryl;

or R$^a$ is

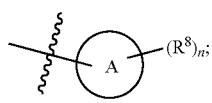

ring A is selected from the group consisting of cycloalkyl, heterocyclyl, aryl and heteroaryl;

R$^c$ is selected from the group consisting of hydrogen, alkyl, haloalkyl, alkenyl and alkynyl;

R$^1$ and R$^2$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, cyano, hydroxy, hydroxyalkyl, cycloalkyl, heterocyclyl, aryl and heteroaryl;

R$^3$ and R$^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

R$^5$, R$^6$ and R$^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

L$^1$ is selected from the group consisting of alkylene, alkenylene, NH, —(CH$_2$)$_s$NH—, O, S(O)$_m$, C(O), —C(O)NH—, —NHC(O)— or —HNC(O)NH—, wherein the alkylene or alkenylene is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl; two substitutes on the same carbon can form a cycloalkyl or heterocyclyl ring; two substitutes on adjacent carbons can form a cycloalkyl, heterocyclyl, aryl and heteroaryl ring;

or L$^1$ is absent;

Z is selected from the group consisting of —C(O)O-benzyl, butyloxy carbonyl, hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, —NR$^9$R$^{10}$, cycloalkyl, heterocyclyl, aryl and heteroaryl;

or Z is selected from a formula (Za) or a tautomer:

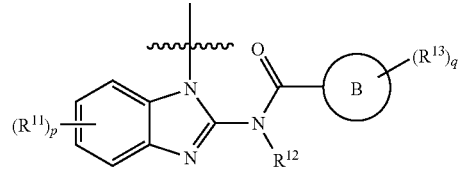

(Za)

wherein, ring B is selected from the group consisting of cycloalkyl, heterocyclyl, aryl and heteroaryl;

R$^8$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

R$^9$ and R$^{10}$ are identical or different, and each is independently selected from the group consisting of hydrogen, alkyl, —C(O)O-benzyl, haloalkyl, cycloalkyl, heterocyclyl, aryl and heteroaryl;

R$^{11}$ each is identical or different, and each is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl;

R$^{12}$ is selected from the group consisting of hydrogen, alkyl, alkenyl and alkynyl;

R$^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^{14}$ and $R^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, hydroxy, cyano, nitro, alkyl, alkoxy, cycloalkyl, heterocyclyl, aryl and heteroaryl;

n is 0, 1, 2, 3 or 4;
m is 0, 1 or 2;
s is integer of 1 to 6;
p is 0, 1, 2, 3 or 4; and
q is 0, 1, 2, 3 or 4.

When $R^c$ is hydrogen, the compound may exist in any of the tautomer forms (III), (III'), or (III''), or a mixture thereof, all of which are encompassed by the present invention:

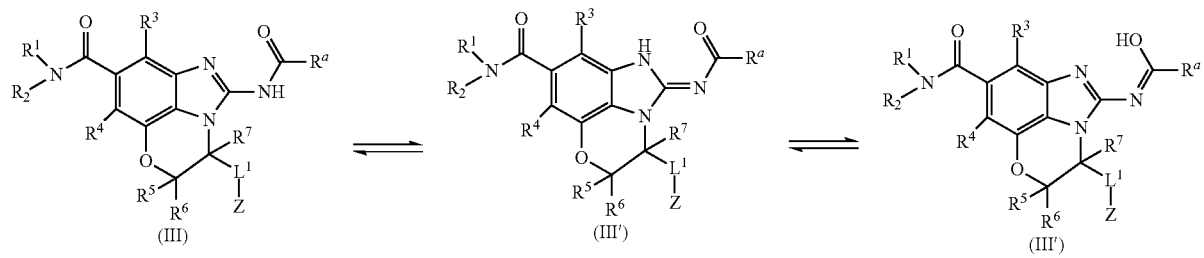

wherein: $R^a$, $L^1$, Z and $R^1$ to $R^7$ each as defined in formula (I).

In one embodiment, $L^1$ is a bond, and the compound of formula (I) or formula (III), further characterized by formula (IV):

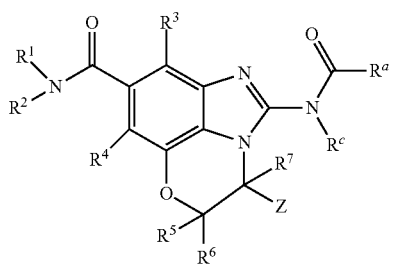

wherein:

Z is selected from the group consisting of hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, —NHC(O)O-benzyl, cycloalkyl, heterocyclyl, aryl and heteroaryl;

$R^a$, $R^c$ and $R^1$ to $R^7$ are each as defined in formula (I).

In another embodiment, in the compound of formula (I), or a tautomer, or a pharmaceutically acceptable salt, solvate, or prodrug thereof, $R^a$ is alkyl optionally substituted with one or more, preferably one to five, and sometimes more preferably one to three, carboxyl (—$CO_2H$) groups;

or $R^a$ is

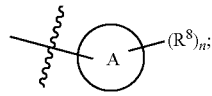

and ring A, $R^8$ and n are each as defined in formula (I).

In another embodiment, the compound of formula I) is further characterized by formula (V):

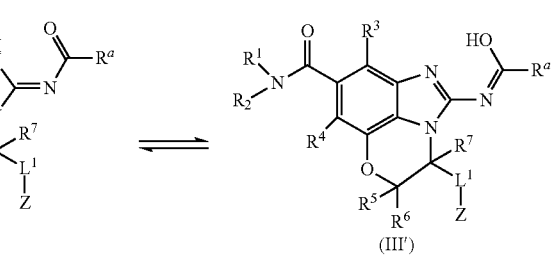

or a tautomer, or a pharmaceutically acceptable salt, solvate, or prodrug thereof;

wherein:

G, t, ring A, $R^c$, $R^1$ to $R^8$, $L^1$, Z and n are each as defined in formula (I).

In another embodiment, the compound of formula (I) is further characterized by formula (VI):

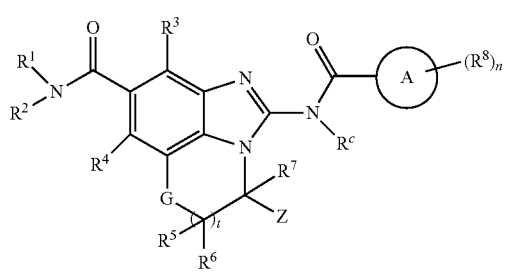

or a tautomer, or a pharmaceutically acceptable salt, solvate, or prodrug thereof;

wherein:

Z is selected from the group consisting of hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, oxo, —C(O)OR$^{18}$, R$^{19}$, —NHC(O)O-benzyl, cycloalkyl, heterocyclyl, aryl and heteroaryl;

G, R$^{18}$, R$^{19}$, t, ring A, R$^c$, R$^1$ to R$^8$ and n are each as defined in formula (I).

In another embodiment, the compound of formula (I) or formula (III) is further characterized by formula (VII):

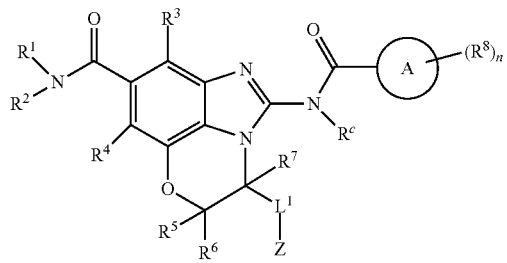

(VII)

or a tautomer, or a pharmaceutically acceptable salt, solvate, or prodrug thereof;

wherein:

ring A, R$^c$, R$^1$ to R$^8$, L$^1$, Z and n are each as defined in formula (I).

In another embodiment, R$^c$ is hydrogen and the compound of formula (VII) is further characterized by formula (VII'):

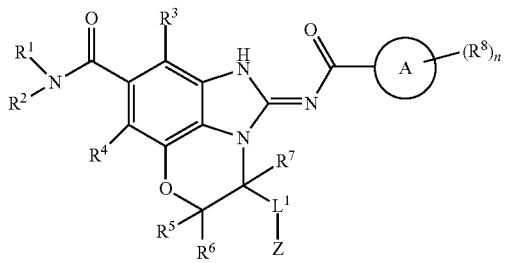

(VII')

or a tautomer, or a pharmaceutically acceptable salt, solvate, or prodrug thereof;

wherein:

ring A, R$^c$, R$^1$ to R$^8$, L$^1$, Z and n are each as defined in formula (VII).

In another embodiment, R$^c$ is hydrogen and the compound of formula (VII) is further characterized by formula (VII"):

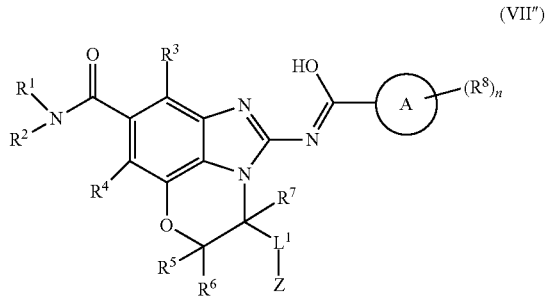

(VII")

or a tautomer, or a pharmaceutically acceptable salt, solvate, or prodrug thereof;

wherein:

ring A, R$^c$, R$^1$ to R$^8$, L$^1$, Z and n are each as defined in formula (VII).

In another embodiment, the compound of formula (I) or formula (III) is further characterized by formula (VIII):

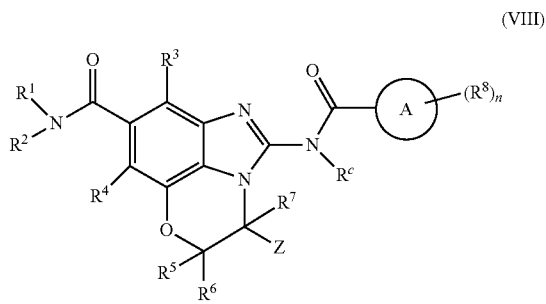

(VIII)

or a tautomer, or a pharmaceutically acceptable salt, solvate, or prodrug thereof;

wherein:

Z is selected from the group consisting of hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, —NHC(O)O-benzyl, cycloalkyl, heterocyclyl, aryl and heteroaryl; and ring A, R$^b$, R$^c$, R$^1$ to R$^8$ and n are each as defined in formula (I).

In another embodiment, in the compound of formula (I), or a tautomer, or a pharmaceutically acceptable salt, solvate, or prodrug thereof, R$^7$ is selected from the group consisting of hydrogen and alkyl.

In another embodiment, in the compound of formula (I), or a tautomer, or a pharmaceutically acceptable salt, solvate, or prodrug thereof, Z is selected from the group consisting of hydrogen, alkyl and alkenyl, wherein the alkyl is unsubstituted or substituted with one or more, preferably one to five, and sometimes more preferably one to three, substituents selected from the group consisting of halogen, hydroxyl and —NHC(O)O— benzyl.

In another embodiment, in the compound of formula (I), or a tautomer, or a pharmaceutically acceptable salt, solvate, or prodrug thereof wherein R$^{11}$ is selected from the group consisting of hydrogen, alkoxy and —C(O)NR$^{14}$R$^{15}$; wherein the alkoxy is unsubstituted or substituted with one or more, preferably one to five, and sometimes more preferably one to three, substituents selected from the group consisting of alkoxy, alkenyl, amino, hydroxy, hydroxyalkyl, cyano, —O—P(O)(OH)$_2$, cycloalkyl, heterocyclyl and NR$^{16}$R$^{17}$;

R$^{14}$ and R$^{15}$ are identical or different, and each is independently selected from hydrogen or alkyl;

R$^{16}$ and R$^{17}$ are identical or different, and each is independently selected from hydrogen or alkyl;

or, R$^{16}$ and R$^{17}$ together with the nitrogen atom to which they are attached form a heterocyclyl, wherein the heterocyclyl contains one or two identical or different heteroatoms selected from the group consisting of N, O and S.

In another embodiment, the compound of formula (I) is further characterized by formula (IX):

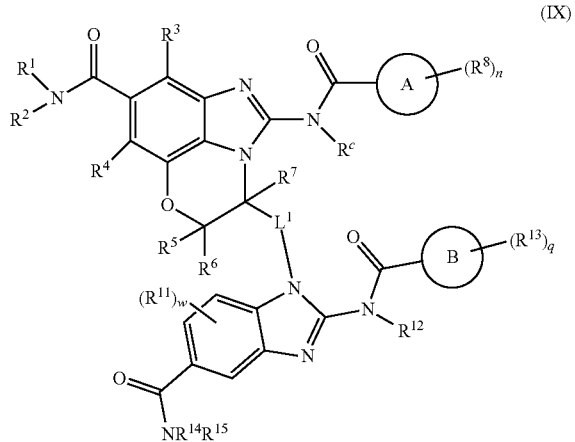

(IX)

or a tautomer, or a pharmaceutically acceptable salt, solvate, or prodrug thereof;
wherein:
L$^1$ is selected from the group consisting of —(CH$_2$)$_s$NH(CH$_2$)$_r$—, alkylene and alkenylene, wherein the alkylene or alkenylene is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

R$^{14}$ and R$^{15}$ are identical or different, and each is independently selected from the group consisting of hydrogen and alkyl;

w is 0, 1, 2 or 3; and
ring A, ring B, R$^c$, R$^1$ to R$^6$, R$^8$, R$^{11}$, R$^{12}$, R$^{13}$, r, s n and q are each as defined in formula (I);

preferably, R$^{11}$ is selected from hydrogen or alkoxy; wherein the alkoxy is unsubstituted or substituted with one or more, preferably one to five, and sometimes more preferably one to three, substituents selected from the group consisting of alkoxy, alkenyl, amino, hydroxy, —O—P(O)(OH)$_2$ and NR$^{16}$R$^{17}$;

R$^{16}$ and R$^{17}$ are identical or different, and each is independently selected from hydrogen or alkyl;

or, R$^{16}$ and R$^{17}$ together with the nitrogen atom to which they are attached form a heterocyclyl, wherein the heterocyclyl contains one or two identical or different heteroatoms selected from the group consisting of N, O and S.

In another embodiment, the compound of formula (I) is further characterized by formula (X):

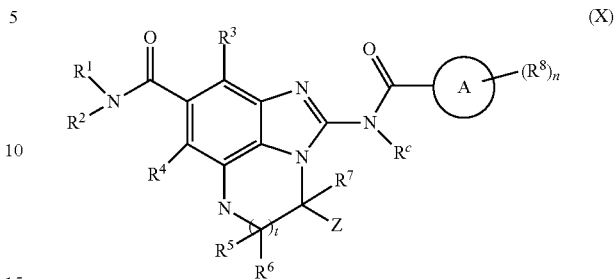

(X)

or a tautomer, or a pharmaceutically acceptable salt, solvate, or prodrug thereof;
wherein t, ring A, R$^c$, R$^1$ to R$^8$, L$^1$, Z and n are each as defined in formula (I).

In another embodiment, the compound of formula (I) is further characterized by formula (XI):

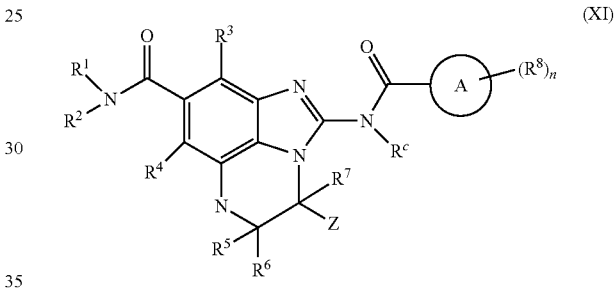

(XI)

or a tautomer, or a pharmaceutically acceptable salt, solvate, or prodrug thereof;
wherein ring A, R$^c$, R$^1$ to R$^8$, L$^1$, Z and n are each as defined in formula (I).

In another embodiment, in the compound of formula (I), or a tautomer, or a pharmaceutically acceptable salt, solvate, or prodrug thereof, t is 1.

In another embodiment, in the compound of formula (I), or a tautomer, or a pharmaceutically acceptable salt, solvate, or prodrug thereof, L$^1$ is selected from the group consisting of alkylene and alkenylene, wherein the alkylene or alkenylene is unsubstituted or substituted with one or more, preferably one to five, and sometimes more preferably one to three, substituents selected from the group consisting of halogen and hydroxy.

In another embodiment, in the compound of formula (I), or a tautomer, or a pharmaceutically acceptable salt, solvate, or prodrug thereof, L$^1$ is selected from the group consisting of alkylene and alkenylene, wherein the alkylene or alkenylene is unsubstituted or substituted with one or more, preferably one to five, and sometimes more preferably one to three, substituents selected from the group consisting of oxo, —C(O)OR$^{18}$, R$^{19}$, halogen and hydroxy;

R$^{18}$ is hydrogen or alkyl; R$^{19}$ is heteroaryl unsubstituted or substituted with one or more, preferably one to five, and sometimes more preferably one to three, substituents selected from alkyl or alkoxy, preferably, R$^{19}$ is heteroaryl unsubstituted or substituted with one or more, preferably one to five, and sometimes more preferably one to three, substituents selected from alkyl or alkoxy, preferably R$^{19}$ is group of

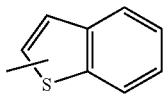

substituted with one or more, preferably one to five, and sometimes more preferably one to three, substituents selected from alkyl or alkoxy;

preferably, $L^1$ is selected from the group consisting of alkylene and alkenylene, wherein the alkylene or alkenylene is unsubstituted or substituted with one or more, preferably one to five, and sometimes more preferably one to three, hydroxy.

In another embodiment, in the compound of formula (I), or a tautomer, or a pharmaceutically acceptable salt, solvate, or prodrug thereof, ring A is selected from the group consisting of heteroaryl and aryl, preferably pyrazolyl or imidazolyl.

In another embodiment, in the compound of formula (I), or a tautomer, or a pharmaceutically acceptable salt, solvate, or prodrug thereof, ring B is selected from the group consisting of heteroaryl and aryl, preferably pyrazolyl or imidazolyl.

In another embodiment, in the compound of formula (I), or a tautomer, or a pharmaceutically acceptable salt, solvate, or prodrug thereof, $R^c$ is selected from the group consisting of hydrogen and alkyl.

In another embodiment of the invention, in the compound of formula (I), or a tautomer, or a pharmaceutically acceptable salt, solvate, or prodrug thereof, $R^1$ and $R^2$ are identical or different, and each is independently selected from the group consisting of hydrogen and alkyl; wherein the alkyl is unsubstituted or substituted with one or more, preferably one to five, and sometimes more preferably one to three, hydroxy.

In another embodiment, in the compound of formula (I), or a tautomer, or a pharmaceutically acceptable salt, solvate, or prodrug thereof, $R^3$, $R^4$, $R^5$ or $R^6$ are each hydrogen.

In another embodiment, in the compound of formula (I), or a tautomer, or a pharmaceutically acceptable salt, solvate, or prodrug thereof, $R^8$ at each occurrence is independently selected from the group consisting of hydrogen and alkyl.

Exemplary compounds of the present invention include, but are not limited to the following:

| Example No. | Structure and Name |
|---|---|
| 1 | 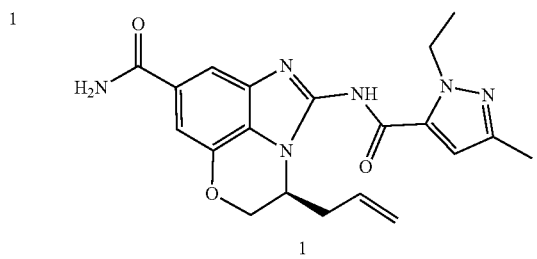<br>(S)-3-allyl-2-(1-ethyl-3-methyl-1H-pyrazole-5-carboxamido)-3,4-dihydro-5-oxa-1,2a-diazaacenaphthylene-7-carboxamide 1 |
| 2 | 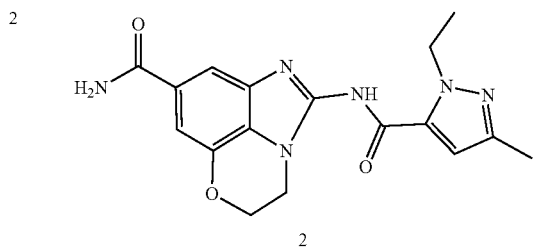<br>2-(1-ethyl-3-methyl-1H-pyrazole-5-carboxamido)-3,4-dihydro-5-oxa-1,2a-diazaacenaphthylene-7-carboxamide 2 |
| 3 | 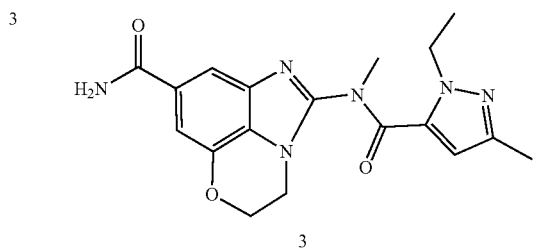<br>2-(1-ethyl-N,3-dimethyl-1H-pyrazole-5-carboxamido)-3,4-dihydro-5-oxa-1,2a-diazaacenaphthylene-7-carboxamide 3 |

| Example No. | Structure and Name |
|---|---|
| 4 | 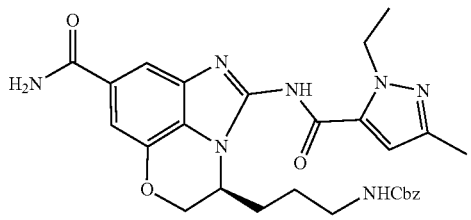
(S)-benzyl(3-(7-carbamoyl-2-(1-ethyl-3-methyl-1H-pyrazole-5-carboxamido)-3,4-dihydro-5-oxa-1,2a-diazaacenaphthylen-3-yl)propyl)carbamate 4 |
| 5 | 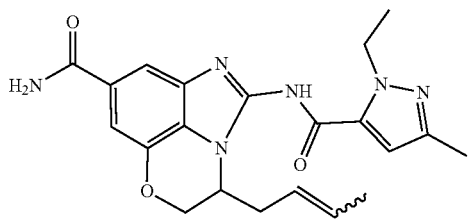
3-(but-2-en-1-yl)-2-(1-ethyl-3-methyl-1H-pyrazole-5-carboxamido)-3,4-dihydro-5-oxa-1,2a-diazaacenaphthylene-7-carboxamide 5 |
| | 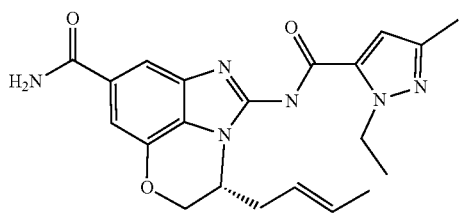
(R,E)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-1 |
| | 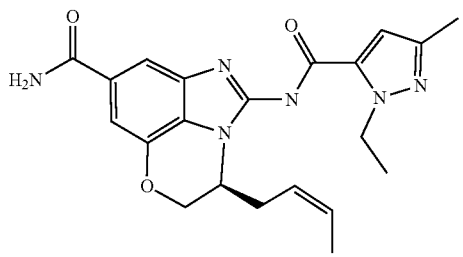
(S,Z)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-2 |

| Example No. | Structure and Name |
|---|---|
| | 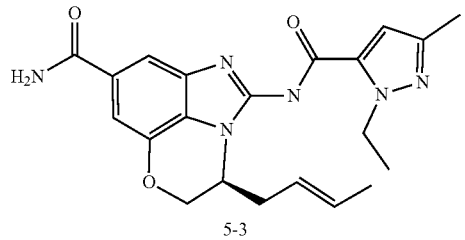 [SMILES: C/C=C/C[C@H]1COc2cc(C(N)=O)cc3nc(NC(=O)c4cc(C)nn4CC)n1c23]
5-3

(S,E)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-3 |
| 6 | 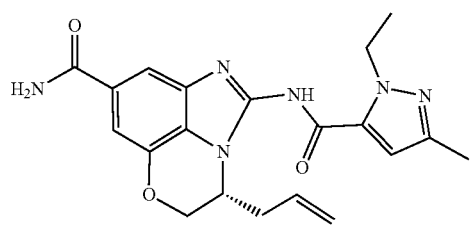
6

(R)-3-allyl-2-(1-ethyl-3-methyl-1H-pyrazole-5-carboxamido)-3,4-dihydro-5-oxa-1,2a-diazaacenaphthylene-7-carboxamide 6 |
| 7 | 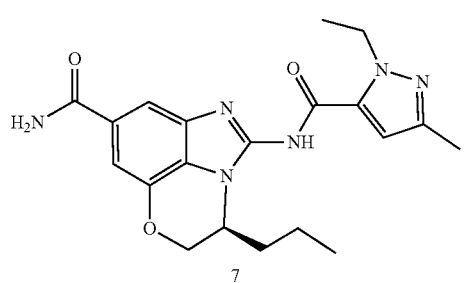 [SMILES: CCC[C@H]1COc2cc(C(N)=O)cc3nc(NC(=O)c4cc(C)nn4CC)n1c23]
7

(S)-2-(1-ethyl-3-methyl-1H-pyrazole-5-carboxamido)-3-propyl-3,4-dihydro-5-oxa-1,2a-diazaacenaphthylene-7-carboxamide 7 |
| 8 | 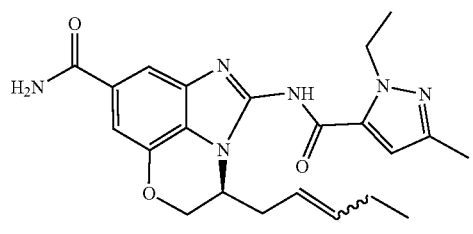
8

(S)-2-(1-ethyl-3-methyl-1H-pyrazole-5-carboxamido)-3-(pent-2-en-1-yl)-3,4-dihydro-5-oxa-1,2a-diazaacenaphthylene-7-carboxamide 8 |

-continued

| Example No. | Structure and Name |
|---|---|
| 9 | 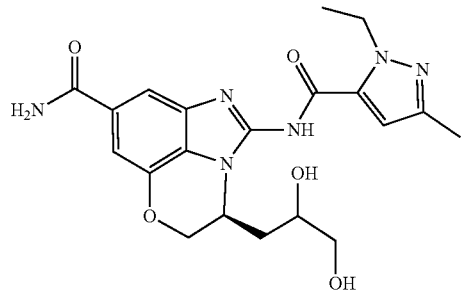

9

(3S)-3-(2,3-dihydroxypropyl0-2-(1-ethyl-3-methyl-1H-pyrazole-5-carboxamido)-3,4-dihydro-5-oxa-1,2a-diazaacenaphthylene-7-carboxamide 9 |
| 10 | 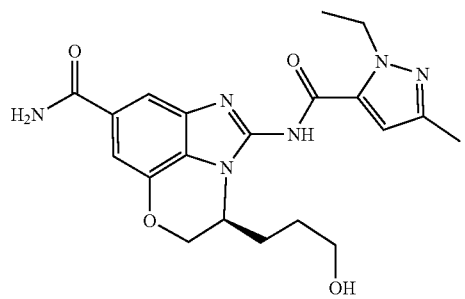

10

(S)-2-(1-ethyl-3-methyl-1H-pyrazole-5-carboxamido)-3-(3-hydroxypropyl)-3,4-dihydro-5-oxa-1,2a-diazaacenaphthylene-7-carboxamide 10 |
| 11 | 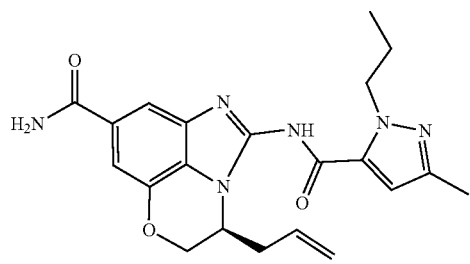

11

(S)-3-allyl-2-(3-methyl-1-propyl-1H-pyrazole-5-carboxamido)-3,4-dihydro-5-oxa-1,2a-diazaacenaphthylene-7-carboxamide 11 |
| 12 | 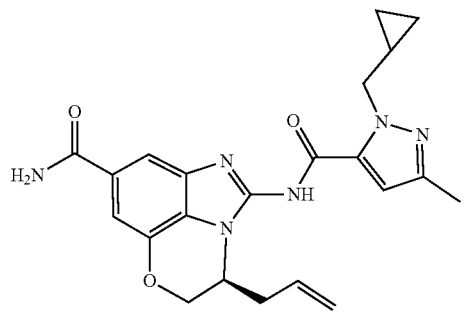

12

(S)-3-allyl-2-(1-(cyclopropylmethyl)-3-methyl-1H-pyrazole-5-carboxamido)-3,4-dihydro-5-oxa-1,2a-diazaacenaphthylene-7-carboxamide 12 |

| Example No. | Structure and Name |
|---|---|
| 13 | 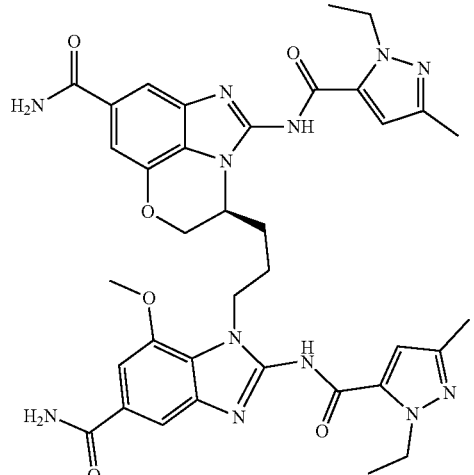

13

(S)-3-(3-(5-carbamoyl-2-(1-ethyl-3-methyl-1H-pyrazole-5-carboxamido)-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 13 |
| 14 | 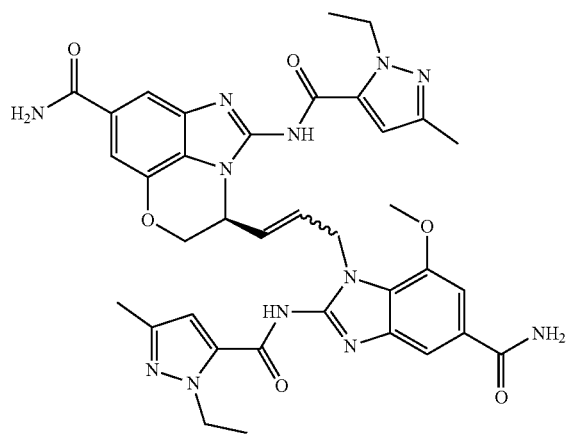

14

(S)-3-(3-(5-carbamoyl-2-(1-ethyl-3-methyl-1H-pyrazole-5-carboxamido)-7-methoxy-1H-benzo[d]imidazol-1-yl)prop-1-en-1-yl)-2-(1-ethyl-3-methyl-1H-pyrazole-5-carboxamido)-3,4-dihydro-5-oxa-1,2a-diazaacenaphthylene-7-carboxamide 14 |

| Example No. | Structure and Name |
|---|---|
| 15 | 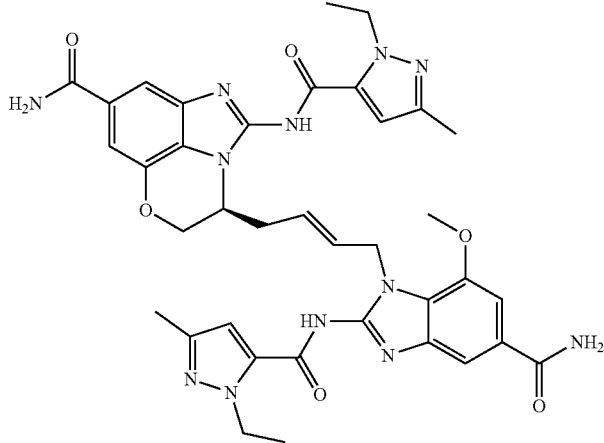

(S,E)-3-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-3,4-dihydro-5-oxa-1,2a-diazaacenaphthylene-7-carboxamide 15 |
| 16 | 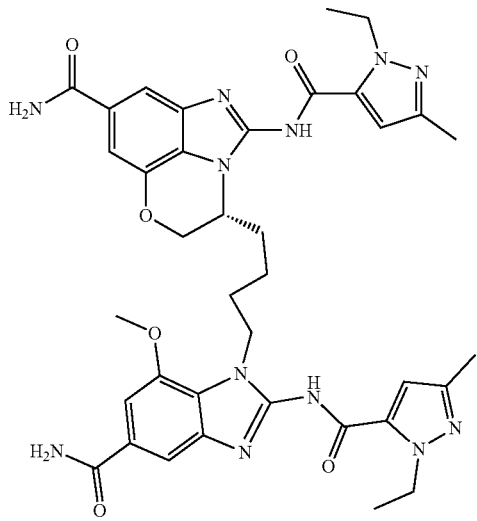

(R)-3-(4-(5-carbamoyl-2-(1-ethyl-3-methyl-1H-pyrazole-5-carboxamido)-7-methoxy-1H-benzo[d]imidazol-1-yl)butyl)-2-(1-ethyl-3-methyl-1H-pyrazole-5-carboxamido)-3,4-dihydro-5-oxa-1,2a-diazaacenaphthylene-7-carboxamide 16 |

| Example No. | Structure and Name |
|---|---|
| 17 | 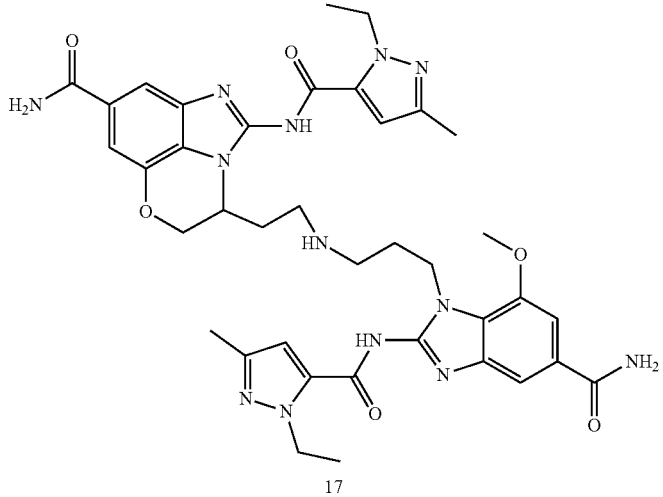 [SMILES: CCn1nc(C)cc1C(=O)Nc1nc2cc(C(N)=O)cc(OC)c2n1CCCNCCC1COc2cc(C(N)=O)cc3nc(NC(=O)c4cc(C)nn4CC)n1c23]

3-(2-((3-(5-carbamoyl-2-(1-ethyl-3-methyl-1H-pyrazole-5-carboxamido)-7-methoxy-1H-benzo[d]imidazol-1-yl)propyl)amino)ethyl)-2-(1-ethyl-3-methyl-1H-pyrazole-5-carboxamido)-3,4-dihydro-5-oxa-1,2a-diazaacenaphthylene-7-carboxamide 17 |
| 18 | 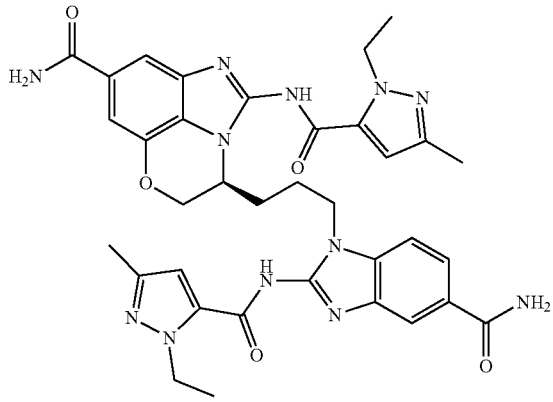

(S)-3-(3-(5-carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 18 |

| Example No. | Structure and Name |
|---|---|
| 19 | 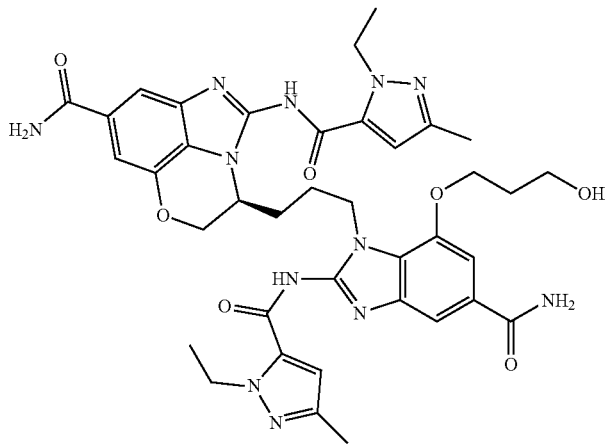<br>(S)-3-(3-(5-carbamoyl-2-(1-ethyl-3-methyl-1H-pyrazole-5-carboxamido)-7-(3-hydroxypropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 19 |
| 20 | 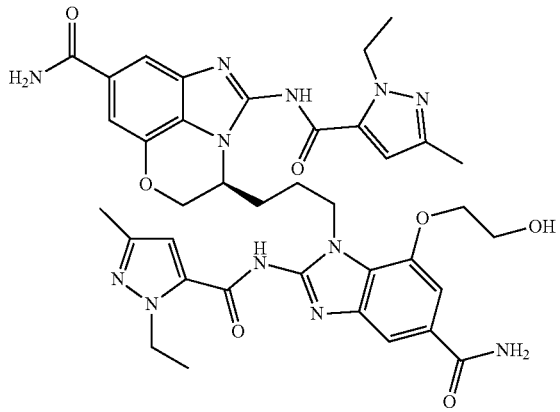<br>(S)-3-(3-(5-carbamoyl-2-(1-ethyl-3-methyl-1H-pyrazole-5-carboxamido)-7-(2-hydroxyethoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 20 |

-continued

| Example No. | Structure and Name |
|---|---|
| 21 | 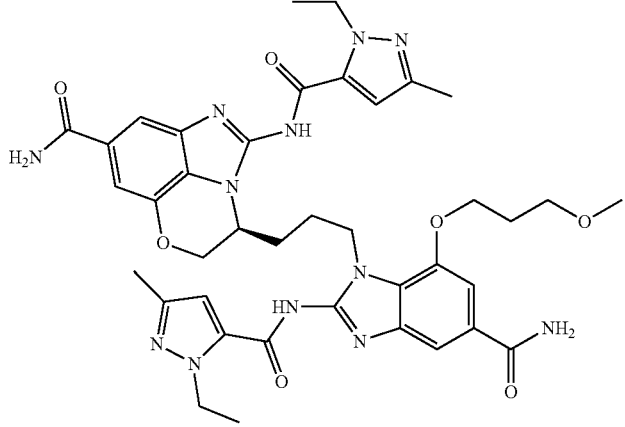

21

(S)-3-(3-(5-carbamoyl-2-(1-ethyl-3-methyl-1H-pyrazole-5-carboxamido)-7-(3-methoxypropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 21 |
| 22 | 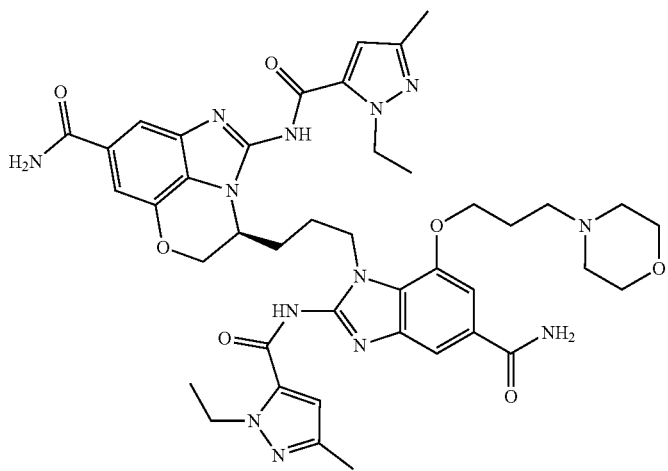

22

(S)-3-(3-(5-carbamoyl-2-(1-ethyl-3-methyl-1H-pyrazole-5-carboxamido)-7-(3-morpholinopropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 22 |

-continued

| Example No. | Structure and Name |
|---|---|
| 23 | 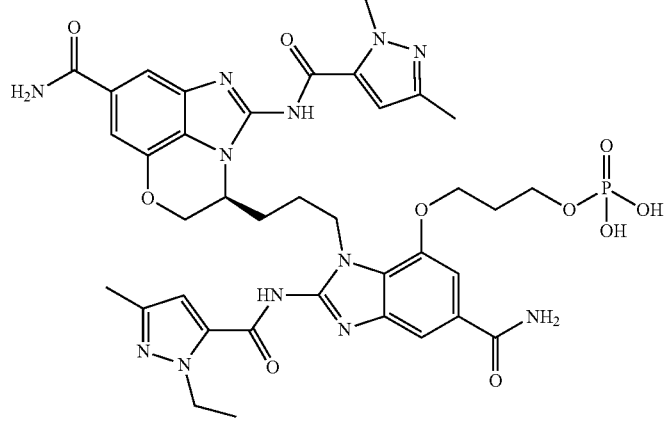
23

(S)-3-45-carbamoyl-1-(3-(7-carbamoyl-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-1H-benzo[d]imidazol-7-yl)oxy)propyl dihydrogen phosphate 23 |
| 24 | 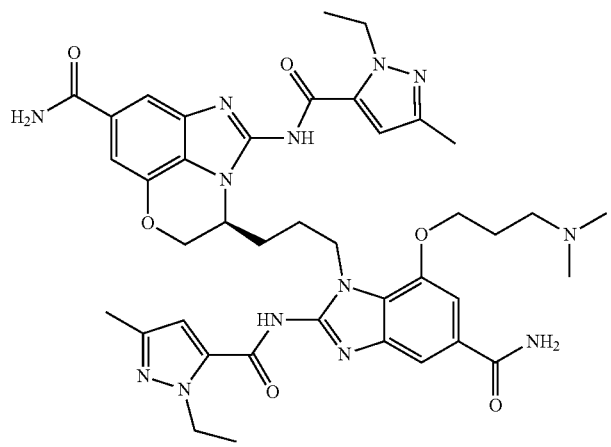
24

(S)-3-(3-(5-carbamoyl-7-(3-(dimethylamino)propoxy)-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 24 |

| Example No. | Structure and Name |
|---|---|
| 25 | 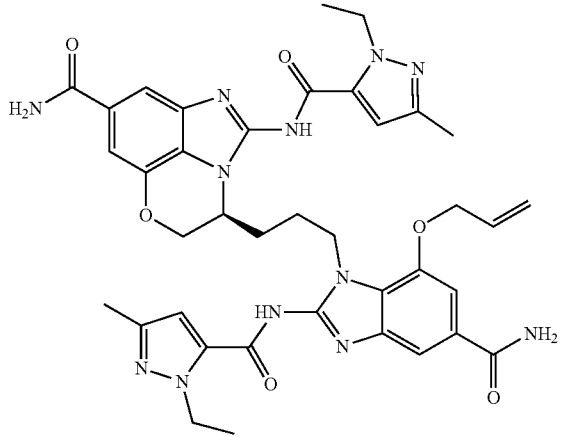

25

(S)-3-(3-(7-(allyloxy)-5-carbamoyl-2-(1-ethyl-3-methyl-1H-pyrazole-5-carboxamido)-1H-benzoyl)propyl)-2-(1-ethyl-3-methyl-1H-pyrazole-5-carboxamido)-3,4-dihydro-5-oxa-1,2a-diazaacenaphthylene-7-carboxamide 25 |
| 26 | 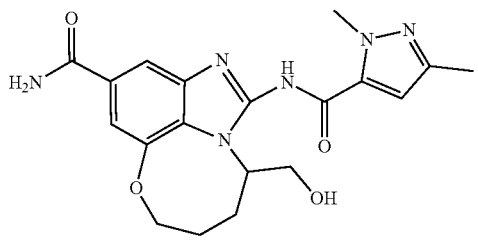

26

1-(1-ethyl-3-methyl-1H-pyrazole-5-carboxamido)-10-(hydroxymethyl)-7,8,9,10-tetrahydro-6-oxa-2,10a-diazacycloocta[cd]indene-4-carboxamide 26 |
| 27 | 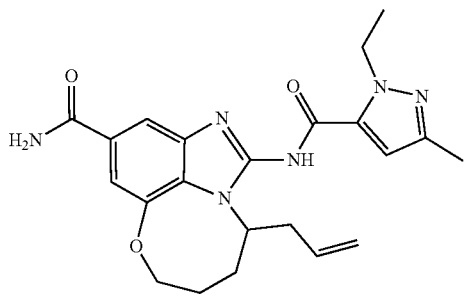

27

10-allyl-1-(1-ethyl-3-methyl-1H-pyrazole-5-carboxamido)-7,8,9,10-tetrahydro-6-oxa-2,10a-diazacycloocta[cd]indene-4-carboxamide 27 |

| Example No. | Structure and Name |
|---|---|
| 28 | 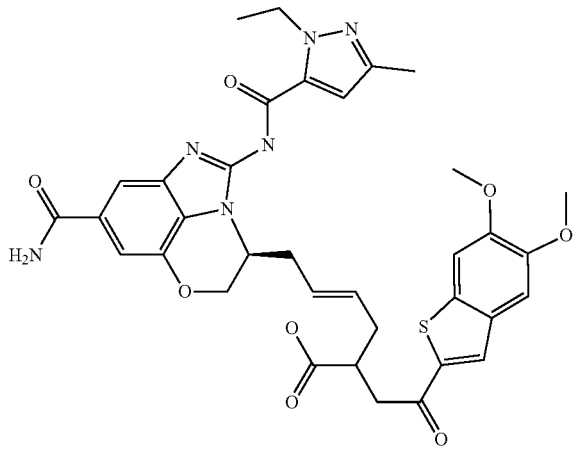

(E)-6-((S)-7-carbamoyl-2-(1-ethyl-3-methyl-1H-pyrazole-5-carboxamido)-3,4-dihydro-5-oxa-1,2a-diazaacenaphthylen-3-yl)-2-(2-(5,6-dimethoxybenzo[b]thiopen-2-yl)-2-oxoethyl)hex-4-enoic acid 28 |
| 29 | 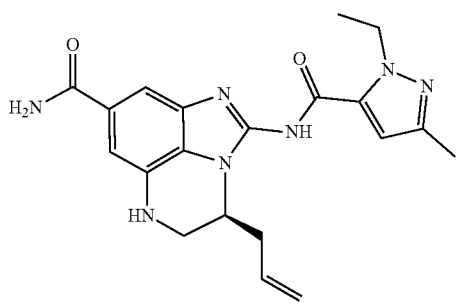

(S)-4-allyl-2-(1-ethyl-3-methyl-1H-pyrazole-5-carboxamido)-5,6-dihydro-4H-imidazo[1,5,4-de]quinoxaline-8-carboxamide 29 |
| 30 | 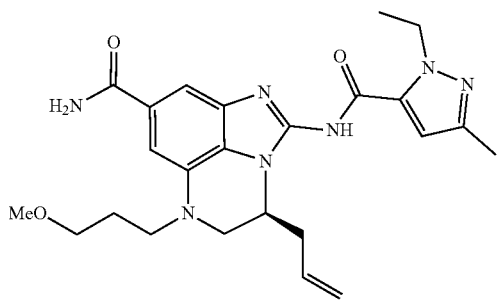

(S)-4-allyl-2-(1-ethyl-3-methyl-1H-pyrazole-5-carboxamido)-6-(3-methoxypropyl)-5,6-dihydro-4H-imidazo[1,5,4-de]quinoxaline-8-carboxamide 30 |

| Example No. | Structure and Name |
|---|---|
| 31 | 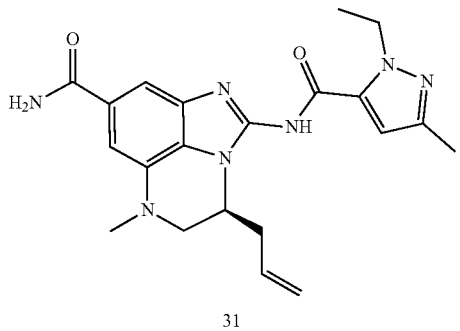 [SMILES: C=CC[C@H]1CN(C)c2cc(C(N)=O)cc3nc(NC(=O)c4cc(C)nn4CC)n1c23]<br>(S)-4-allyl-2-(1-ethyl-3-methyl-1H-pyrazole-5-carboxamido)-6-methyl-5,6-dihydro-4H-imidazo[1,5,4-de]quinoxaline-8-carboxamide 31 | or a tautomer, racemate, enantiomer, diastereomer, or mixture thereof, or a pharmaceutically acceptable salt, solvate, or prodrug thereof.

In another aspect, this invention provides a compound of formula (IA), or a tautomer thereof, used as an intermediate for preparing a compound of formula (I):

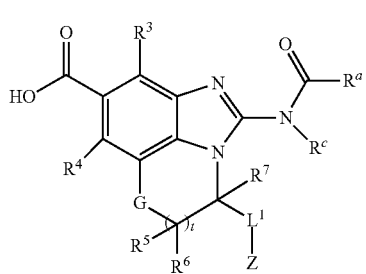

wherein:

$R^a$ is selected from the group consisting of alkyl, alkenyl, alkynyl, haloalkyl, and hydroxyalkyl, wherein the alkyl, alkenyl or alkynyl is unsubstituted or substituted with one or more, preferably one to five, and sometimes more preferably one to three, substituents selected from the group consisting of halogen, alkyl, alkoxy, haloalkyl, amino, nitro, cyano, hydroxy, hydroxyalkyl, carboxylic acid, cycloalkyl, heterocyclyl, aryl and heteroaryl;

or $R^a$ is

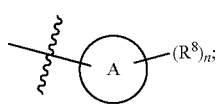

ring A is selected from the group consisting of cycloalkyl, heterocyclyl, aryl and heteroaryl;

G is O or $NR^b$;

$R^b$ is selected from the group consisting of hydrogen, alkyl, alkoxy, alkoxyalkyl and haloalkyl;

$R^c$ is selected from the group consisting of hydrogen, alkyl, haloalkyl, alkenyl and alkynyl;

$R^3$ and $R^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$R^5$, $R^6$ and $R^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$L^1$ is selected from the group consisting of alkylene, alkenylene, NH, O, —$(CH_2)_s$NH—, —$(CH_2)_s$NH$(CH_2)_r$—, $S(O)_m$, C(O), —C(O)NH—, —NHC(O)— or —HNC(O)NH—, wherein the alkylene or alkenylene is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, oxo, —C(O)$OR^{18}$, $R^{19}$, cycloalkyl, heterocyclyl, aryl and heteroaryl;

or $L^1$ is absent;

Z is selected from the group consisting of —C(O)O-benzyl, Butyloxy carbonyl, hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, —$NR^9R^{10}$, oxo, —C(O)$OR^{18}$, $R^{19}$, cycloalkyl, heterocyclyl, aryl and heteroaryl;

or Z is selected from a formula (Za) or a tautomer

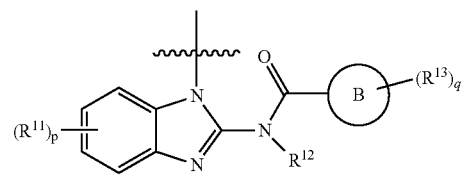

wherein, ring B is selected from the group consisting of cycloalkyl, heterocyclyl, aryl and heteroaryl;

R[8] each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

R[9] and R[10] are identical or different, and each is independently selected from the group consisting of hydrogen, alkyl, —C(O)O-benzyl, haloalkyl, cycloalkyl, heterocyclyl, aryl and heteroaryl;

R[11] each is identical or different, and each is independently selected from the group consisting of hydrogen, halogen, alkyl, alkoxy, haloalkyl, amino, nitro, hydroxy, hydroxyalkyl, cyano, —C(O)NR[14]R[15], cycloalkyl, heterocyclyl, aryl and heteroaryl; wherein the alkyl or alkoxy is unsubstituted or substituted with one or more, preferably one to five, and sometimes more preferably one to three, substituents selected from the group consisting of halogen, alkyl, alkoxy, alkenyl, alkynyl haloalkyl, amino, nitro, hydroxy, hydroxyalkyl, cyano, —O—P(O)(OH)$_2$, cycloalkyl, heterocyclyl and NR[16]R[17];

R[12] is selected from the group consisting of hydrogen, alkyl, alkenyl and alkynyl;

R[13] each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

R[14] and R[15] are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, hydroxy, cyano, nitro, alkyl, alkoxy, cycloalkyl, heterocyclyl, aryl and heteroaryl;

R[16] and R[17] are identical or different, and each is independently selected from hydrogen or alkyl;

or, R[16] and R[17] together with the nitrogen atom to which they are attached form a heterocyclyl, wherein the heterocyclyl contains one or two identical or different heteroatoms selected from the group consisting of N, O and S, and the heterocyclyl is optionally substituted by one or more, preferably one to five, and sometimes more preferably one to three, substituents selected from the group consisting of alkyl, alkoxy, halogen, amino, cyano, nitro, hydroxy and hydroxyalkyl;

R[18] is hydrogen or alkyl;

R[19] is cycloalkyl, heterocyclyl, aryl or heteroaryl, wherein the cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl and cyano;

n is 0, 1, 2, 3 or 4;
m is 0, 1 or 2;
s is integer of 1 to 6;
r is 1, 2, 3 or 4;
t is 1, 2, 3 or 4;
p is 0, 1, 2, 3 or 4; and
q is 0, 1, 2, 3 or 4.

In another aspect, this invention provides a compound of formula (IB), or a tautomer thereof, used as an intermediate for preparing a compound of formula (I):

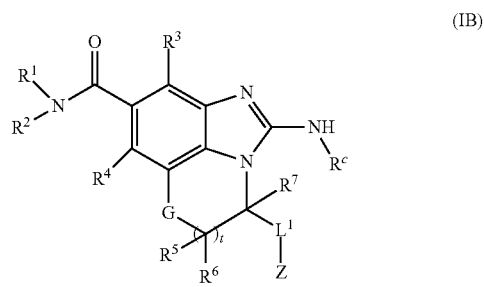

(IB)

wherein:

G is O or NR$^b$;

R$^b$ is selected from the group consisting of hydrogen, alkyl, alkoxy, alkoxyalkyl and haloalkyl;

R$^c$ is selected from the group consisting of hydrogen, alkyl, haloalkyl, alkenyl and alkynyl;

R[1] and R[2] are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, cyano, hydroxy, hydroxyalkyl, cycloalkyl, heterocyclyl, aryl and heteroaryl;

R[3] and R[4] are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

R[5], R[6] and R[7] are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

L[1] is selected from the group consisting of alkylene, alkenylene, NH, O, —(CH$_2$)$_s$NH—, —(CH$_2$)$_s$NH(CH$_2$)$_r$—, S(O)$_m$, C(O), —C(O)NH—, —NHC(O)— or —HNC(O)NH—, wherein the alkylene or alkenylene is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, oxo, —C(O)OR[18], R[19], cycloalkyl, heterocyclyl, aryl and heteroaryl;

or L[1] is absent;

Z is selected from the group consisting of —C(O)O-benzyl, Butyloxy carbonyl, hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, —NR$^9$R$^{10}$, oxo, —C(O)OR$^{18}$, R$^{19}$, cycloalkyl, heterocyclyl, aryl and heteroaryl;

or Z is selected from a formula (Za) or a tautomer:

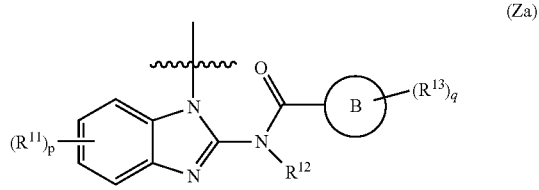

(Za)

wherein, ring B is selected from the group consisting of cycloalkyl, heterocyclyl, aryl and heteroaryl;

R$^9$ and R$^{10}$ are identical or different, and each is independently selected from the group consisting of hydrogen, alkyl, —C(O)O-benzyl, haloalkyl, cycloalkyl, heterocyclyl, aryl and heteroaryl;

R$^{11}$ each is identical or different, and each is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl; wherein the alkyl or alkoxy is unsubstituted or substituted with one or more, preferably one to five, and sometimes more preferably one to three, substituents selected from the group consisting of halogen, alkyl, alkoxy, alkenyl, alkynyl haloalkyl, amino, nitro, hydroxy, hydroxyalkyl, cyano, —O—P(O)(OH)$_2$, cycloalkyl, heterocyclyl and NR$^{16}$R$^{17}$;

R$^{12}$ is selected from the group consisting of hydrogen, alkyl, alkenyl and alkynyl;

R$^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

R$^{14}$ and R$^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, hydroxy, cyano, nitro, alkyl, alkoxy, cycloalkyl, heterocyclyl, aryl and heteroaryl;

R$^{16}$ and R$^{17}$ are identical or different, and each is independently selected from hydrogen or alkyl;

or, R$^{16}$ and R$^{17}$ together with the nitrogen atom to which they are attached form a heterocyclyl, wherein the heterocyclyl contains one or two identical or different heteroatoms selected from the group consisting of N, O and S, and the heterocyclyl is optionally substituted by one or more, preferably one to five, and sometimes more preferably one to three, substituents selected from the group consisting of alkyl, alkoxy, halogen, amino, cyano, nitro, hydroxy and hydroxyalkyl;

R$^{18}$ is hydrogen or alkyl;

R$^{19}$ is cycloalkyl, heterocyclyl, aryl or heteroaryl, wherein the cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl and cyano;

m is 0, 1 or 2;
s is integer of 1 to 6;
r is 1, 2, 3 or 4;
t is 1, 2, 3 or 4;
p is 0, 1, 2, 3 or 4; and
q is 0, 1, 2, 3 or 4.

In another aspect, this invention provides a compound of formula (IIIA), or a tautomer thereof, used as an intermediate for preparing a compound of formula (III):

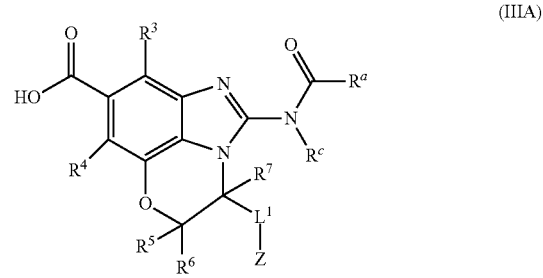

(IIIA)

wherein:

R$^a$ is selected from the group consisting of alkyl, alkenyl, alkynyl, haloalkyl, and hydroxyalkyl, wherein the alkyl, alkenyl or alkynyl is unsubstituted or substituted with one or more, preferably one to five, and sometimes more preferably one to three, substituents selected from the group consisting of halogen, alkyl, alkoxy, haloalkyl, amino, nitro, cyano, hydroxy, hydroxyalkyl, carboxylic acid, cycloalkyl, heterocyclyl, aryl and heteroaryl;

or R$^a$ is

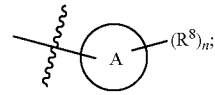

ring A is selected from the group consisting of cycloalkyl, heterocyclyl, aryl and heteroaryl;

R$^c$ is selected from the group consisting of hydrogen, alkyl, haloalkyl, alkenyl and alkynyl;

R$^3$ and R$^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

R$^5$, R$^6$ and R$^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

L$^1$ is selected from the group consisting of alkylene, alkenylene, NH, O, —(CH$_2$)$_s$NH—, S(O)$_m$, C(O), —C(O)NH—, —NHC(O)— or —HNC(O)NH—, wherein the alkylene or alkenylene is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

or $L^1$ is absent;

Z is selected from the group consisting of —C(O)O-benzyl, Butyloxy carbonyl, hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, —$NR^9R^{10}$, cycloalkyl, heterocyclyl, aryl and heteroaryl;

or Z is selected from a formula (Za):

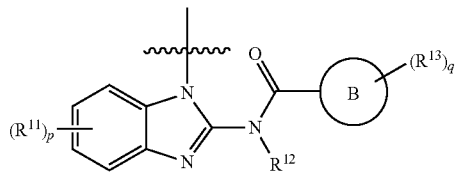

(Za)

wherein, ring B is selected from the group consisting of cycloalkyl, heterocyclyl, aryl and heteroaryl;

$R^8$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^9$ and $R^{10}$ are identical or different, and each is independently selected from the group consisting of hydrogen, alkyl, —C(O)O-benzyl, haloalkyl, cycloalkyl, heterocyclyl, aryl and heteroaryl;

$R^{11}$ each is identical or different, and each is independently selected from the group consisting of hydrogen, halogen, alkyl, alkoxy, haloalkyl, amino, nitro, hydroxy, hydroxyalkyl, cyano, —$C(O)NR^{14}R^{15}$, cycloalkyl, heterocyclyl, aryl and heteroaryl;

$R^{12}$ is selected from the group consisting of hydrogen, alkyl, alkenyl and alkynyl;

$R^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^{14}$ and $R^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, hydroxy, cyano, nitro, alkyl, alkoxy, cycloalkyl, heterocyclyl, aryl and heteroaryl;

n is 0, 1, 2, 3 or 4;
m is 0, 1 or 2;
s is integer of 1 to 6;
p is 0, 1, 2, 3 or 4; and
q is 0, 1, 2, 3 or 4.

In another aspect, this invention provides a compound of formula (IIIB), or a tautomer thereof, used as an intermediate for preparing a compound of formula (III):

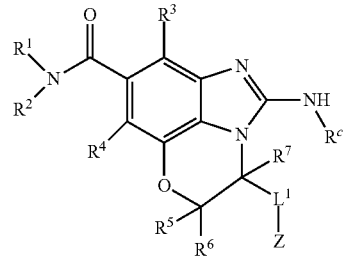

(IIIB)

wherein:

$R^c$ is selected from the group consisting of hydrogen, alkyl, haloalkyl, alkenyl and alkynyl;

$R^1$ and $R^2$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, cyano, hydroxy, hydroxyalkyl, cycloalkyl, heterocyclyl, aryl and heteroaryl;

$R^3$ and $R^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$R^5$, $R^6$ and $R^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$L^1$ is selected from the group consisting of alkylene, alkenylene, NH, O, —$(CH_2)_sNH$—, $S(O)_m$, C(O), —C(O)NH—, —NHC(O)— or —HNC(O)NH—, wherein the alkylene or alkenylene is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

or $L^1$ is absent;

Z is selected from the group consisting of —C(O)O-benzyl, Butyloxy carbonyl, hydrogen, halogen, alkyl, alkenyl, alkynyl alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, —NR⁹R¹⁰, cycloalkyl, heterocyclyl, aryl and heteroaryl;

or Z is selected from a formula (Za):

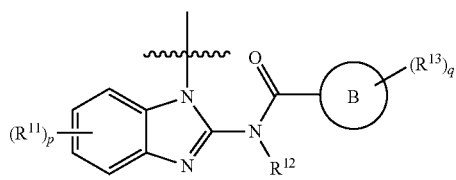

(Za)

wherein, ring B is selected from the group consisting of cycloalkyl, heterocyclyl, aryl and heteroaryl;

R⁹ and R¹⁰ are identical or different, and each is independently selected from the group consisting of hydrogen, alkyl, —C(O)O-benzyl, haloalkyl, cycloalkyl, heterocyclyl, aryl and heteroaryl;

R¹¹ each is identical or different, and each is independently selected from the group consisting of hydrogen, halogen, alkyl, alkoxy, haloalkyl, amino, nitro, hydroxy, hydroxyalkyl, cyano, —C(O)NR¹⁴R¹⁵, cycloalkyl, heterocyclyl, aryl and heteroaryl;

R¹² is selected from the group consisting of hydrogen, alkyl, alkenyl and alkynyl;

R¹³ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more, preferably one to five, and sometimes more preferably one to three, substituents selected from the group consisting of halogen, alkyl, alkoxy, haloalkyl, amino, nitro, hydroxy, hydroxyalkyl, cyano, cycloalkyl, heterocyclyl, aryl and heteroaryl;

R¹⁴ and R¹⁵ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more, preferably one to five, and sometimes more preferably one to three, substituents selected from the group consisting of halogen, hydroxy, cyano, nitro, alkyl, alkoxy, cycloalkyl, heterocyclyl, aryl and heteroaryl;

m is 0, 1 or 2;

s is integer of 1 to 6;

p is 0, 1, 2, 3 or 4; and q is 0, 1, 2, 3 or 4.

In another aspect, this invention provides a preparation process of a compound of formula (I), or a tautomer, or a pharmaceutically acceptable salt, solvate, or prodrug thereof, comprising a step of:

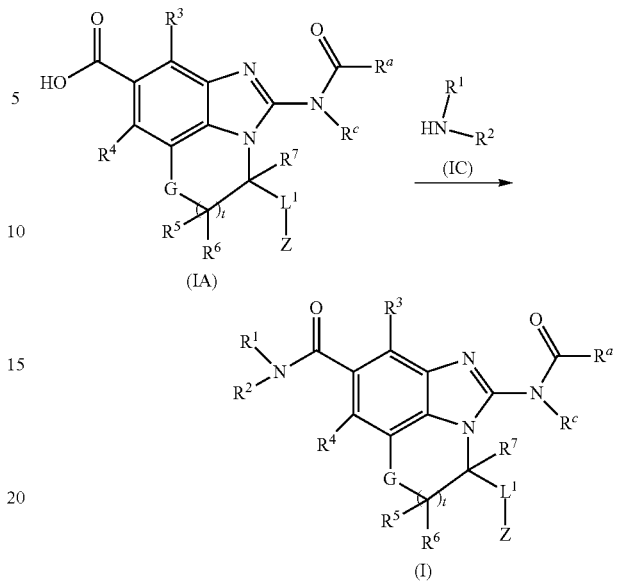

reacting a compound of formula with a compound of formula (IC) to obtain the compound of formula (I);

wherein G, t, Rᵃ, Rᶜ, R¹ to R⁷, L¹ and Z are each as defined in formula (I).

In another aspect, this invention provides a preparation process of a compound of formula (I), or a tautomer, or a pharmaceutically acceptable salt, solvate, or prodrug thereof, comprising a step of:

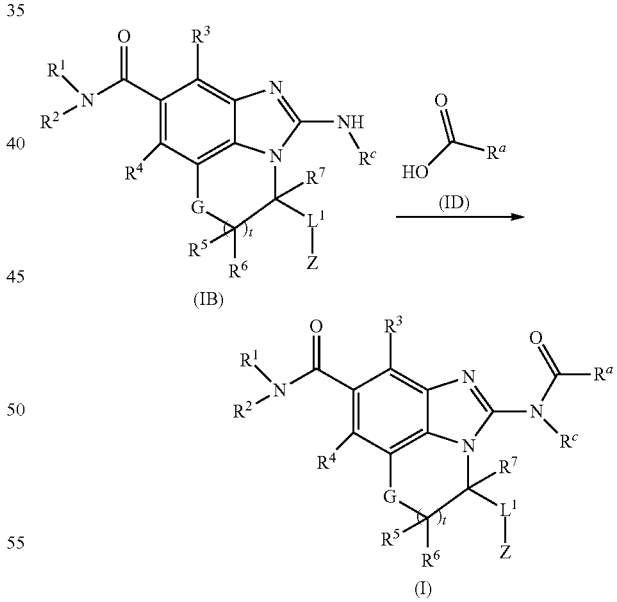

reacting a compound of formula (IB) with a compound of formula (ID) to obtain the compound of formula (I);

wherein G, t, Rᵃ, Rᶜ, R¹ to R⁷, L¹ and Z are each as defined in formula (I).

In another aspect, this invention provides a preparation process of a compound of formula (III), or a tautomer, or a pharmaceutically acceptable salt, solvate, or prodrug thereof, the preparation process comprising the steps of:

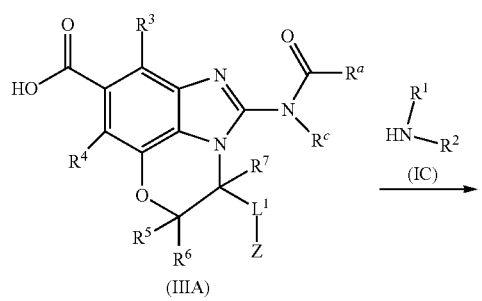

(IIIA)

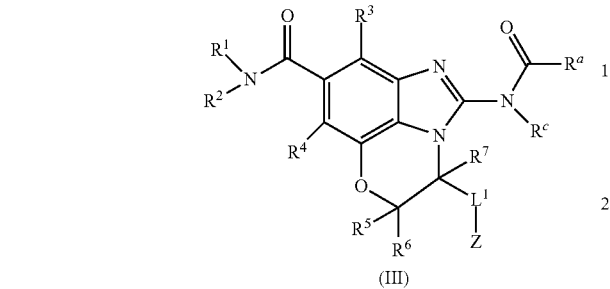

(III)

reacting a compound of formula (IIIA) with a compound of formula (IC) to obtain the compound of formula (III);

wherein $R^a$, $R^c$, $R^1$ to $R^7$ and Z are each as defined in formula (I).

In another aspect, this invention provides a method of preparing a compound of formula (III), or a tautomer, or a pharmaceutically acceptable salt, solvate, or prodrug thereof, the method comprising the steps of:

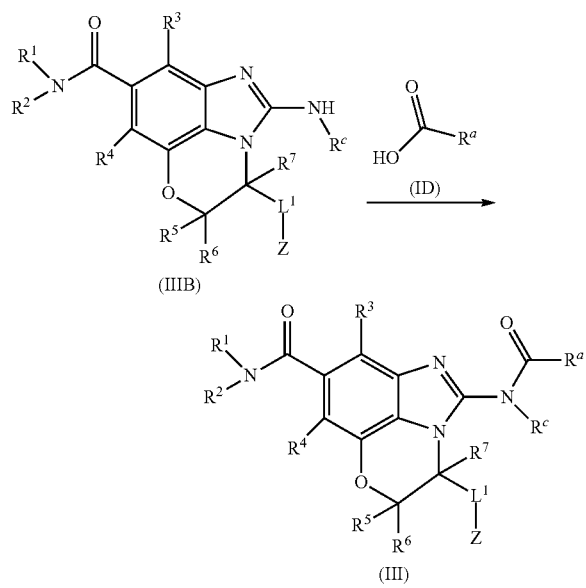

reacting a compound of formula (IIIB) with a compound of formula (ID) to obtain the compound of formula (III), preferably under an alkaline condition;

wherein $R^a$, $R^c$, $R^1$ to $R^7$ and Z are each as defined in formula (III).

The present invention also provides a pharmaceutical composition, comprising a therapeutically effective amount of a compound of formula (I), or a tautomer, or a pharmaceutically acceptable salt, solvate, or prodrug thereof, together with one or more pharmaceutically acceptable carriers, diluents or excipients.

The present invention also relates to use of a compound of formula (I), or a tautomer, a pharmaceutically acceptable salt, solvate, prodrug, or a pharmaceutical composition thereof, in the preparation of a medicament for use as a STING agonist.

The present invention also relates to use of a compound of formula (I), or a tautomer, a pharmaceutically acceptable salt, solvate, or prodrug thereof, or a pharmaceutical composition thereof, in the preparation of a medicament for the treatment of a STING-mediated disease or disorder, wherein the disease or disorder is selected from a cancer, a pre-cancerous syndrome and viral infections, preferably a cancer and a pre-cancerous syndrome.

In other words, the present invention relates to a method for stimulating STING, comprising a step of administering to a subject in need thereof a therapeutically effective amount of a compound of formula (I), or a tautomer, a pharmaceutically acceptable salt, solvate, prodrug, or a pharmaceutical composition thereof.

The present invention relates to a method for treating a STING-mediated disease or disorder, comprising a step of administering to a subject in need thereof a therapeutically effective amount of a compound of formula (I), or a tautomer, a pharmaceutically acceptable salt, solvate, prodrug, or a pharmaceutical composition thereof; wherein the disease or disorder is selected from a cancer, a pre-cancerous syndrome and viral infections, preferably a cancer and a pre-cancerous syndrome.

The compositions of this invention can be formulated by conventional methods using one or more pharmaceutically acceptable carriers. Thus, the active compounds of this invention can be formulated as various dosage forms for oral, buccal, intranasal, parenteral (e.g., intravenous, intramuscular or subcutaneous), rectal administration, inhalation or insufflation administration. The compounds of this invention can also be formulated as sustained release dosage forms.

The compositions can be in the form of a tablet, troche, lozenge, aqueous or oily suspension, dispersible powder or granule, emulsion, hard or soft capsule, or syrup or elixir. Oral compositions can be prepared according to any known method in the art for the preparation of pharmaceutical compositions. Such compositions can contain one or more additives selected from the group consisting of sweeteners, flavoring agents, colorants and preservatives, in order to provide a pleasing and palatable pharmaceutical preparation. Tablets contain the active ingredient and nontoxic pharmaceutically acceptable excipients suitable for the manufacture of tablets. These excipients can be inert excipients, granulating agents, disintegrating agents, and lubricants. The tablet can be uncoated or coated by means of a known technique to mask the taste of the drug or delay the disintegration and absorption of the drug in the gastrointestinal tract, thereby providing sustained release over an extended period. For example, water soluble taste masking materials can be used.

Oral formulations can also be provided as soft gelatin capsules in which the active ingredient is mixed with an inert solid diluent, or the active ingredient is mixed with a water soluble carrier.

An aqueous suspension contains the active ingredient in admixture with excipients suitable for the manufacture of an aqueous suspension. Such excipients are suspending agents, dispersants or humectants, and can be naturally occurring phospholipids. The aqueous suspension can also contain one or more preservatives, one or more colorants, one or more flavoring agents, and one or more sweeteners.

An oil suspension can be formulated by suspending the active ingredient in a vegetable oil, or in a mineral oil. The oil suspension can contain a thickener. The aforementioned sweeteners and flavoring agents can be added to provide a palatable preparation. These compositions can be preserved by adding an antioxidant.

The active ingredient and the dispersants or wetting agents, suspending agent or one or more preservatives can be prepared as a dispersible powder or granule suitable for the preparation of an aqueous suspension by adding water. Suitable dispersants or wetting agents and suspending agents are exemplified by those already mentioned above. Additional excipients, such as sweeteners, flavoring agents and colorants, can also be added. These compositions can be preserved by adding an antioxidant such as ascorbic acid.

The present pharmaceutical composition can also be in the form of an oil-in-water emulsion. The oil phase can be a vegetable oil, or a mineral oil, or mixture thereof. Suitable emulsifying agents can be naturally occurring phospholipids. Sweeteners can be used. Such formulations can also contain moderators, preservatives, colorants and antioxidants.

The pharmaceutical composition can be in the form of a sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. The injectable solution or microemulsion can be introduced into an individual's bloodstream by local bolus injection. Alternatively, it can be advantageous to administer the solution or microemulsion in such a way as to maintain a constant circulating concentration of the present compound. In order to maintain such a constant concentration, a continuous intravenous delivery device can be utilized. An example of such a device is Deltec CADD-PLUS™ 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable preparation can also be a sterile injectable solution or suspension prepared in a nontoxic parenterally acceptable diluent or solvent. Moreover, sterile fixed oils can easily be used as a solvent or suspending medium, and fatty acids can also be used to prepare injections.

The present compound can be administered in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

For buccal administration, the compositions can be formulated as tablets or lozenges by conventional means.

For intranasal administration or administration by inhalation, the active compounds of the present invention are conveniently delivered in the form of a solution or suspension released from a pump spray container that is squeezed or pumped by the patient, or as an aerosol spray released from a pressurized container or nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. The pressurized container or nebulizer can contain a solution or suspension of the active compound. Capsules or cartridges (for example, made from gelatin) for use in an inhaler or insufflator can be formulated containing a powder mix of the present invention and a suitable powder base such as lactose or starch.

It is well known to those skilled in the art that the dosage of a drug depends on a variety of factors, including but not limited to, the following factors: activity of the specific compound, age, weight, general health, behavior, diet of the patient, administration time, administration route, excretion rate, drug combination and the like. In addition, the best treatment, such as treatment mode, daily dose of the compound of formula (I) or the type of pharmaceutically acceptable salt, solvate, or prodrug thereof can be verified by traditional therapeutic regimens.

Any terms in the present application, unless specifically defined, will take the ordinary meanings as understood by a person of ordinary skill in the art.

As used herein, the singular forms "a", "an", and "the" include plural reference unless the context clearly dictates otherwise.

Unless otherwise stated, the terms used in the specification and claims have the meanings described below.

"Alkyl" refers to a saturated aliphatic hydrocarbon group including $C_1$-$C_{20}$ straight chain and branched chain groups. Preferably an alkyl group is an alkyl having 1 to 12, sometimes preferably 1 to 8, sometimes more preferably 1 to 6, and sometimes most preferably 1 to 4, carbon atoms. Representative examples include, but are not limited to, methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. More preferably an alkyl group is a lower alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, preferably the substituent group(s) is one or more, preferably one to five, and sometimes more preferably one to three, groups independently selected from the group consisting of alkyl, halogen, alkoxy, alkenyl, alkynyl, alkylsulfo, alkylamino, thiol, hydroxy, nitro, cyano, amino, cycloalkyl, heterocyclic alkyl, aryl, heteroaryl, cycloalkoxyl, heterocylic, cycloalkylthio, heterocyclic alkylthio, oxo group and —NR$^9$R$^{10}$.

"Alkenyl" refers to an alkyl defined as above that has at least two carbon atoms and at least one carbon-carbon double bond, for example, vinyl, 1-propenyl, 2-propenyl, 1-, 2-, or 3-butenyl, etc. preferably C$_{2-20}$ alkenyl, more preferably C$_{2-12}$ alkenyl, sometimes more preferably C$_{2-8}$ alkenyl, and most preferably C$_{2-6}$ alkenyl. The alkenyl group can be substituted or unsubstituted. When substituted, the substituent group(s) is preferably one or more, preferably one to five, and sometimes more preferably one to three, group(s) independently selected from the group consisting of alkyl, halogen, alkoxy, alkenyl, alkynyl, alkylsulfo, alkylamino, thiol, hydroxy, nitro, cyano, amino, cycloalkyl, heterocyclic alkyl, aryl, heteroaryl, cycloalkoxyl, heterocylic, cycloalkylthio, heterocyclic alkylthio, oxo group and —NR$^9$R$^{10}$.

"Alkynyl" refers to an alkyl defined as above that has at least two carbon atoms and at least one carbon-carbon triple bond, for example, ethynyl, 1-propynyl, 2-propynyl, 1-, 2-, or 3-butynyl etc., preferably C$_{2-20}$ alkynyl, more preferably C$_{2-12}$ alkynyl, sometimes more preferably C$_{2-8}$ alkynyl, and most preferably C$_{2-6}$ alkynyl. The alkynyl group can be substituted or unsubstituted. When substituted, the substituent group(s) is preferably one or more, preferably one to five, and sometimes more preferably one to three, substituent(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocyclic alkylthio and —NR$^9$R$^{10}$.

"Alkylene" refers to a saturated linear or branched aliphatic hydrocarbon group, wherein having 2 residues derived by removing two hydrogen atoms from the same carbon atom of the parent alkane or two different carbon atoms. The straight or branched chain group containing 1 to 20 carbon atoms, preferably has 1 to 12 carbon atoms, more preferably 1 to 8 carbons, more preferably 1 to 6 carbon atoms, and sometimes most preferably 1 to 4 carbon atoms. Non-limiting examples of alkylene groups include, but are not limited to, methylene (—CH$_2$—), 1,1-ethylene (—CH(CH$_3$)—), 1,2-ethylene (—CH$_2$CH$_2$)—, 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylidene (—CH$_2$CH$_2$CH$_2$CH$_2$—) etc. The alkylene group can be substituted or unsubstituted. When substituted, the substituent group(s) is preferably one or more, preferably one to five, and sometimes more preferably one to three, substituent(s) independently selected from the group consisting of selected from alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocylic alkoxyl, cycloalkylthio, heterocyclic alkylthio and —NR$^9$R$^{10}$.

"Alkenylene" refers to an alkylene defined as above that has at least two carbon atoms and at least one carbon-carbon double bond, preferably C$_{2-20}$ alkenylene, more preferably C$_{2-12}$ alkenylene, sometimes more preferably C$_{2-8}$ alkenylene, and most preferably C$_{2-6}$ alkenylene. Non-limiting examples of alkenylene groups include, but are not limited to, —CH═CH—, —CH═CHCH$_2$—, —CH═CHCH$_2$CH$_2$—, —CH$_2$CH═CHCH$_2$— etc. The alkenylene group can be substituted or unsubstituted. When substituted, the substituent group(s) is preferably one or more, preferably one to five, and sometimes more preferably one to three, substituent(s) independently selected from the group consisting of selected from alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocylic alkylthio and —NR$^9$R$^{10}$.

"Cycloalkyl" refers to a saturated and/or partially unsaturated monocyclic or polycyclic hydrocarbon group having 3 to 20 carbon atoms, preferably 3 to 12 carbon atoms, more preferably 3 to 10 carbon atoms, and most preferably 3 to 8 carbon atoms or 3 to 6 carbon atoms. Representative examples of monocyclic cycloalkyls include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes a cycloalkyl having a spiro ring, fused ring or bridged ring.

"Spiro Cycloalkyl" refers to a 5 to 20 membered polycyclic group with rings connected through one common carbon atom (called a spiro atom), wherein one or more rings can contain one or more double bonds, but none of the rings has a completely conjugated pi-electron system. Preferably a spiro cycloalkyl is 6 to 14 membered, and more preferably 7 to 10 membered. According to the number of common spiro atoms, a spiro cycloalkyl is divided into mono-spiro cycloalkyl, di-spiro cycloalkyl, or poly-spiro cycloalkyl, and preferably refers to a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Representative examples of spiro cycloalkyl include, but are not limited to the following groups:

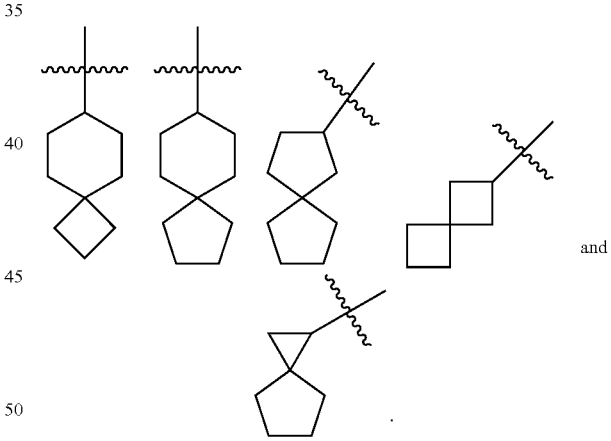

"Fused Cycloalky" refers to a 5 to 20 membered polycyclic hydrocarbon group, wherein each ring in the system shares an adjacent pair of carbon atoms with another ring, wherein one or more rings can contain one or more double bonds, but none of the rings has a completely conjugated pi-electron system. Preferably, a fused cycloalkyl group is 6 to 14 membered, more preferably 7 to 10 membered. According to the number of membered rings, fused cycloalkyl is divided into bicyclic, tricyclic, tetracyclic or polycyclic fused cycloalkyl, and preferably refers to a bicyclic or tricyclic fused cycloalkyl, more preferably 5-membered/5-membered, or 5-membered/6-membered bicyclic fused cycloalkyl. Representative examples of fused cycloalkyls include, but are not limited to, the following groups:

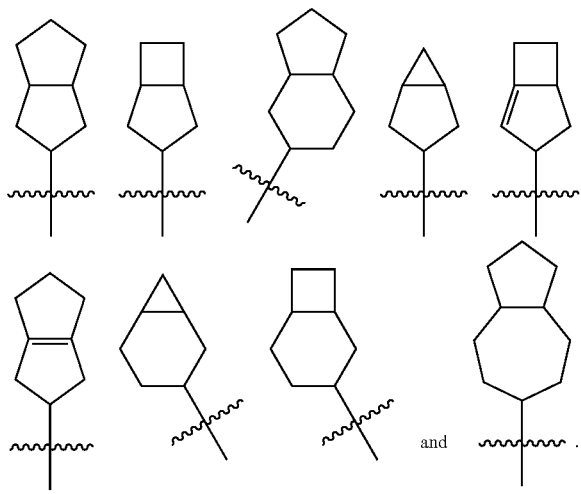

"Bridged Cycloalkyl" refers to a 5 to 20 membered polycyclic hydrocarbon group, wherein every two rings in the system share two disconnected carbon atoms. The rings can have one or more double bonds, but have no completely conjugated pi-electron system. Preferably, a bridged cycloalkyl is 6 to 14 membered, and more preferably 7 to 10 membered. According to the number of membered rings, bridged cycloalkyl is divided into bicyclic, tricyclic, tetracyclic or polycyclic bridged cycloalkyl, and preferably refers to a bicyclic, tricyclic or tetracyclic bridged cycloalkyl, more preferably a bicyclic or tricyclic bridged cycloalkyl. Representative examples of bridged cycloalkyls include, but are not limited to, the following groups:

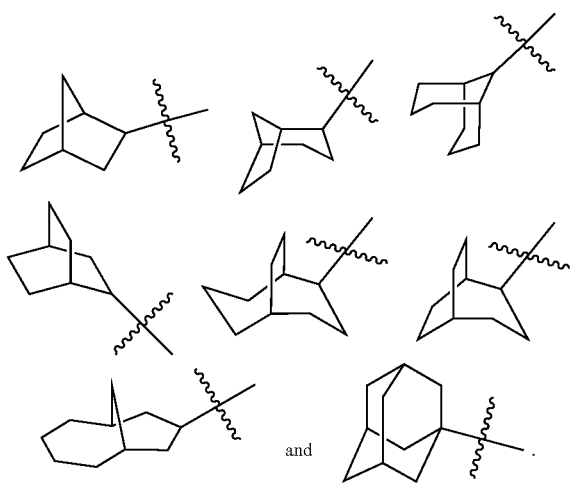

The cycloalkyl can be fused to the ring of an aryl, heteroaryl or heterocyclic alkyl, wherein the ring bound to the parent structure is cycloalkyl. Representative examples include, but are not limited to indanylacetic, tetrahydronaphthalene, benzocycloheptyl and so on. The cycloalkyl is optionally substituted or unsubstituted. When substituted, the substituent group(s) is preferably one or more, preferably one to five, and sometimes more preferably one to three, substituents independently selected from the group consisting of alkyl, halogen, alkoxy, alkenyl, alkynyl, alkylsulfo, alkylamino, thiol, hydroxy, nitro, cyano, amino, cycloalkyl, heterocyclic alkyl, aryl, heteroaryl, cycloalkoxyl, heterocylic, cycloalkylthio, heterocylic alkylthio, oxo group and —NR$^9$R$^{10}$.

"Heterocyclyl" refers to a 3 to 20 membered saturated and/or partially unsaturated monocyclic or polycyclic hydrocarbon group having one or more heteroatoms selected from the group consisting of N, O, and S(O)$_m$ (wherein m is 0, 1, or 2) as ring atoms, but excluding —O—O—, —O—S— or —S—S— in the ring, the remaining ring atoms being C. Preferably, heterocyclyl is a 3 to 12 membered having 1 to 4 heteroatoms; more preferably a 3 to 10 membered having 1 to 3 heteroatoms; most preferably a 5 to 6 membered having 1 to 2 heteroatoms. Representative examples of monocyclic heterocyclyls include, but are not limited to, pyrrolidyl, piperidyl, piperazinyl, morpholinyl, sulfo-morpholinyl, homopiperazinyl, and so on. Polycyclic heterocyclyl includes the heterocyclyl having a spiro ring, fused ring or bridged ring.

"Spiro heterocyclyl" refers to a 5 to 20 membered polycyclic heterocyclyl with rings connected through one common carbon atom (called a spiro atom), wherein said rings have one or more heteroatoms selected from the group consisting of N, O, and S(O)$_m$ (wherein m is 0, 1 or 2) as ring atoms, the remaining ring atoms being C, wherein one or more rings can contain one or more double bonds, but none of the rings has a completely conjugated pi-electron system. Preferably a spiro heterocyclyl is 6 to 14 membered, and more preferably 7 to 10 membered. According to the number of common spiro atoms, spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, more preferably 4-membered/4-membered, 4-membered/5-membered, 4-membered/6-membered, 5-membered/5-membered, or 5-membered/6-membered mono-spiro heterocyclyl. Representative examples of spiro heterocyclyl include, but are not limited to the following groups:

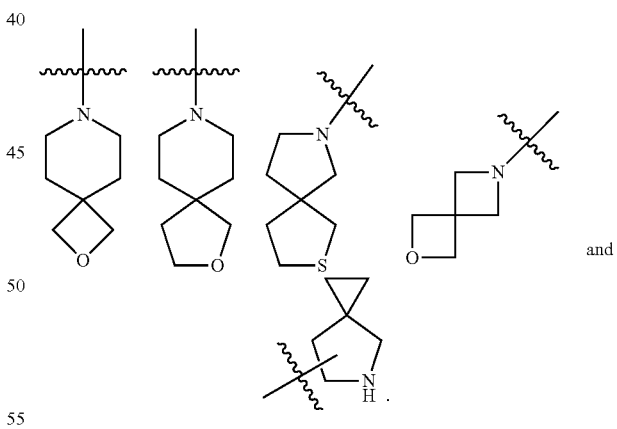

"Fused Heterocyclyl" refers to a 5 to 20 membered polycyclic heterocyclyl group, wherein each ring in the system shares an adjacent pair of carbon atoms with the other ring, wherein one or more rings can contain one or more double bonds, but none of the rings has a completely conjugated pi-electron system, and wherein said rings have one or more heteroatoms selected from the group consisting of N, O, and S(O)$_p$ (wherein p is 0, 1, or 2) as ring atoms, the remaining ring atoms being C. Preferably a fused heterocyclyl is 6 to 14 membered, and more preferably 7 to 10 membered. According to the number of membered rings, fused heterocyclyl is divided into bicyclic, tricyclic, tetracyclic or polycyclic fused heterocyclyl, preferably refers to bicyclic or tricyclic fused heterocyclyl, more preferably 5-membered/5-membered, or 5-membered/6-membered bicyclic fused heterocyclyl. Representative examples of fused heterocyclyl include, but are not limited to, the following groups:

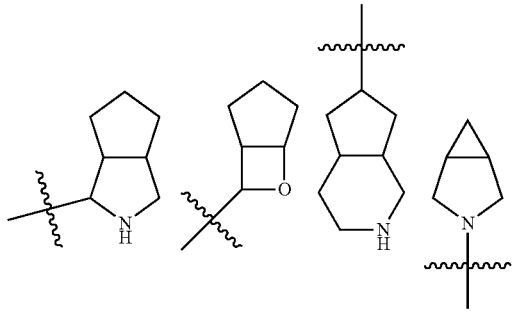

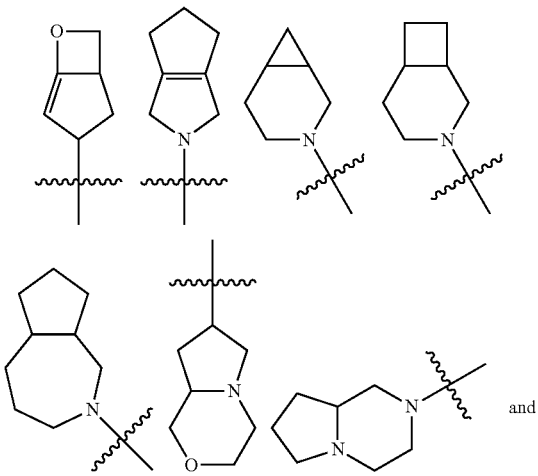

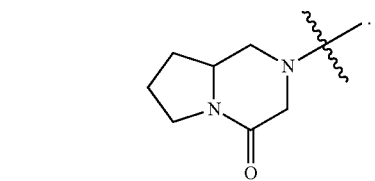

"Bridged Heterocyclyl" refers to a 5 to 14 membered polycyclic heterocyclic alkyl group, wherein every two rings in the system share two disconnected atoms, the rings can have one or more double bonds, but have no completely conjugated pi-electron system, and the rings have one or more heteroatoms selected from the group consisting of N, O, and $S(O)_m$ (wherein m is 0, 1, or 2) as ring atoms, the remaining ring atoms being C. Preferably a bridged heterocyclyl is 6 to 14 membered, and more preferably 7 to 10 membered. According to the number of membered rings, bridged heterocyclyl is divided into bicyclic, tricyclic, tetracyclic or polycyclic bridged heterocyclyl, and preferably refers to bicyclic, tricyclic or tetracyclic bridged heterocyclyl, more preferably bicyclic or tricyclic bridged heterocyclyl. Representative examples of bridged heterocyclyl include, but are not limited to, the following groups:

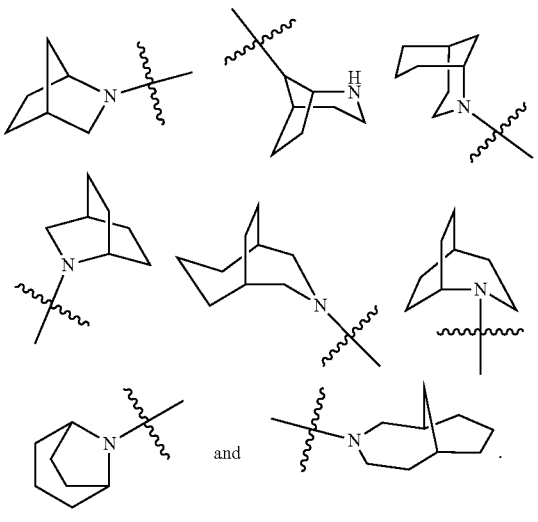

The ring of said heterocyclyl can be fused to the ring of an aryl, heteroaryl or cycloalkyl, wherein the ring bound to the parent structure is heterocyclyl. Representative examples include, but are not limited to the following groups:

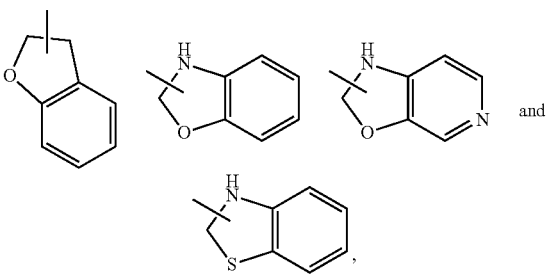

etc.

The heterocyclyl is optionally substituted or unsubstituted. When substituted, the substituent group(s) is preferably one or more, preferably one to five, and sometimes more preferably one to three, substituent(s) independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocylic alkoxyl, cycloalkylthio, heterocylic alkylthio and $-NR^9R^{10}$.

"Aryl" refers to a 6 to 14 membered all-carbon monocyclic ring or a polycyclic fused ring (a "fused" ring system means that each ring in the system shares an adjacent pair of carbon atoms with another ring in the system) group, and has a completely conjugated pi-electron system. Preferably aryl is 6 to 10 membered, such as phenyl and naphthyl, most preferably phenyl. The aryl can be fused to the ring of heteroaryl, heterocyclyl or cycloalkyl, wherein the ring bound to parent structure is aryl. Representative examples include, but are not limited to, the following groups:

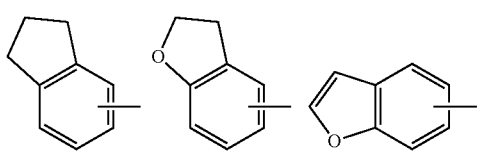

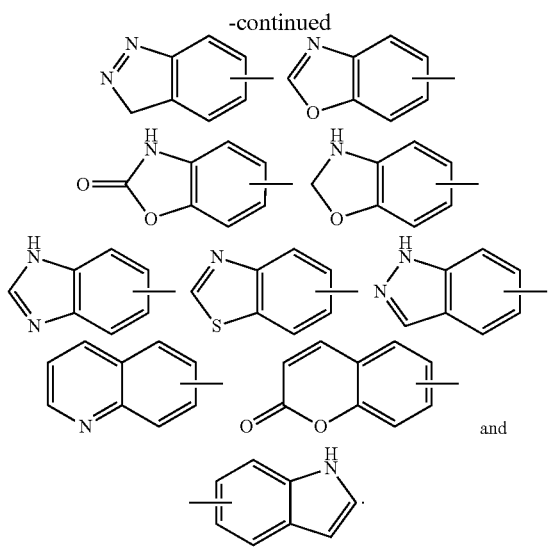

The aryl group can be substituted or unsubstituted. When substituted, the substituent group(s) is preferably one or more, preferably one to five, and sometimes more preferably one to three, substituents independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocyclic alkoxyl, cycloalkylthio, heterocylic alkylthio and —NR$^9$R$^{10}$.

"Heteroaryl" refers to an aryl system having 1 to 4 heteroatoms selected from the group consisting of O, S and N as ring atoms and having 5 to 14 annular atoms. Preferably a heteroaryl is 5- to 10-membered, more preferably 5- or 6-membered, for example, thiadiazolyl, pyrazolyl, oxazolyl, oxadiazolyl, imidazolyl, triazolyl, thiazolyl, furyl, thienyl, pyridyl, pyrrolyl, N-alkyl pyrrolyl, pyrimidinyl, pyrazinyl, imidazolyl, tetrazolyl, and the like. The heteroaryl can be fused with the ring of an aryl, heterocyclyl or cycloalkyl, wherein the ring bound to parent structure is heteroaryl. Representative examples include, but are not limited to, the following groups:

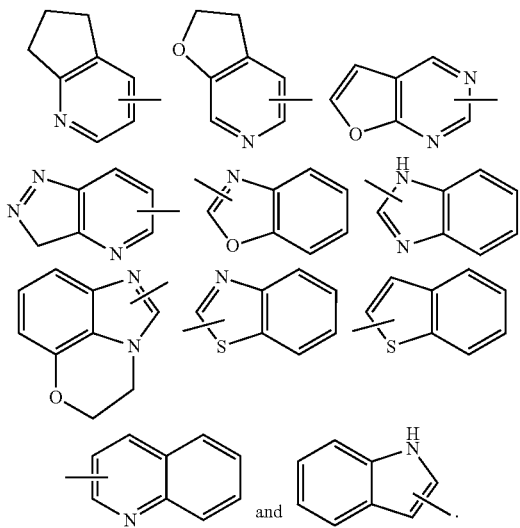

The heteroaryl group can be substituted or unsubstituted. When substituted, the substituent group(s) is preferably one or more, preferably one to five, and sometimes more preferably one to three, substituents independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocylic alkoxyl, cycloalkylthio, heterocylic alkylthio and —NR$^9$R$^{10}$.

"Alkoxy" refers to both an —O-(alkyl) and an —O-(unsubstituted cycloalkyl) group, wherein the alkyl is defined as above. Representative examples include, but are not limited to, methoxy, ethoxy, propoxy, butoxy, cyclopropyloxy, cyclobutyloxy, cyclopentyloxy, cyclohexyloxy, and the like. The alkoxyl can be substituted or unsubstituted. When substituted, the substituent is preferably one or more, preferably one to five, and sometimes more preferably one to three, substituents independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxyl, heterocylic alkoxyl, cycloalkylthio, heterocylic alkylthio and —NR$^9$R$^{10}$.

"Bond" refers to a covalent bond using a sign of "—".

"Hydroxyalkyl" refers to an alkyl group substituted by a hydroxy group, wherein alkyl is as defined above.

"Alkoxyalkyl" refers to an alkyl group substituted by an alkoxyl group, wherein alkyl is as defined above.

"Hydroxy" refers to an —OH group.

"Halogen" refers to fluoro, chloro, bromo or iodo atoms.

"Amino" refers to a —NH$_2$ group.

"Cyano" refers to a —CN group.

"Nitro" refers to a —NO$_2$ group.

"Oxo group" refers to a =O group.

"Carboxyl" refers to a —C(O)OH group.

"Alkoxycarbonyl" refers to a —C(O)O(alkyl) or (cycloalkyl) group, wherein the alkyl and cycloalkyl are defined as above.

"Optional" or "optionally" means that the event or circumstance described subsequently can, but need not, occur, and the description includes the instances in which the event or circumstance may or may not occur. For example, "the heterocyclic group optionally substituted by an alkyl" means that an alkyl group can be, but need not be, present, and the description includes the case of the heterocyclic group being substituted with an alkyl and the heterocyclic group being not substituted with an alkyl. In any "optional" substituents referred to or indicated herein, an alkyl or moiety is preferably C$_{1-6}$ alkyl, sometimes more preferably C$_{1-4}$ alkyl, and sometimes even more preferably methyl or ethyl; an alkenyl or moiety is preferably C$_{2-6}$ alkenyl, sometimes more preferably C$_{2-4}$ alkenyl, and sometimes even more preferably vinyl; an alkynyl or moiety is preferably C$_{2-6}$ alkynyl, sometimes more preferably C$_{2-4}$ alkynyl, and sometimes even more preferably ethynyl; an aryl or moiety is preferably C$_{6-10}$ aryl, and sometimes more preferably phenyl; a heteroaryl or moiety is preferably 5- to 10-membered heteroaryl, and sometimes more preferably 5- to 6-membered heteroaryl; a heterocyclyl or moiety is preferably 5- to 10-membered heterocyclyl, and sometimes more preferably 5- to 6-membered heterocyclyl; and a cycloalkyl or moiety is preferably C$_{3-8}$ cycloalkyl, and sometimes more preferably C$_{2-3}$ cycloalkyl.

"Substituted" refers to one or more hydrogen atoms in the group, preferably up to 5, more preferably 1 to 3 hydrogen atoms, independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxyl group having free hydrogen and carbon atoms having unsaturated bonds (such as olefinic) may be unstable.

A "pharmaceutical composition" refers to a mixture of one or more of the compounds described in the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient and thus displaying biological activity.

"Pharmaceutically acceptable salts" refer to salts of the compounds of the invention, such salts being safe and effective when used in a mammal and have corresponding biological activity. The salts can be prepared during the final isolation and purification of the compounds or separately by reacting a suitable nitrogen atom with a suitable acid. Acids commonly employed to form pharmaceutically acceptable salts include inorganic acids such as hydrochloric acid, hydrobromic acid, hydroiodic acid, sulfuric acid, phosphoric acid, hydrogen bisulfide as well as organic acids, such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, acetic acid, and related inorganic and organic acids.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include, but are not limited to, lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, and N-methylmorpholine.

As a person skilled in the art would understand, the compounds of formula (I) or Pharmaceutically acceptable salts thereof disclosed herein may exist in prodrug or solvate forms, which are all encompassed by the present invention.

The term "solvate," as used herein, means a physical association of a compound of this invention with one or more, preferably one to three, solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. Exemplary solvates include, but are not limited to, hydrates, ethanolates, methanolates, and isopropanolates. Methods of solvation are generally known in the art. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "subject" or "patient" includes both human and other mammals, especially domestic animals, for example, dogs, cats, horses, or the like. A "patient" is preferably a human.

The term "treating" refers to: (i) inhibiting the disease, disorder, or condition, i.e., arresting its development; and (ii) relieving the disease, disorder, or condition, i.e., causing regression of the disease, disorder, and/or condition. In addition, the compounds of present invention may be used for their prophylactic effects in preventing a disease, disorder or condition from occurring in a subject that may be predisposed to the disease, disorder, and/or condition but has not yet been diagnosed as having it.

Synthetic Schemes

To prepare the compounds disclosed herein, the present invention provides, but is not limited to, the following technical solutions:

(1) A preparation process of a compound of formula (I) of the invention or a pharmaceutically acceptable salt, solvate, or prodrug thereof, comprising the following steps of:

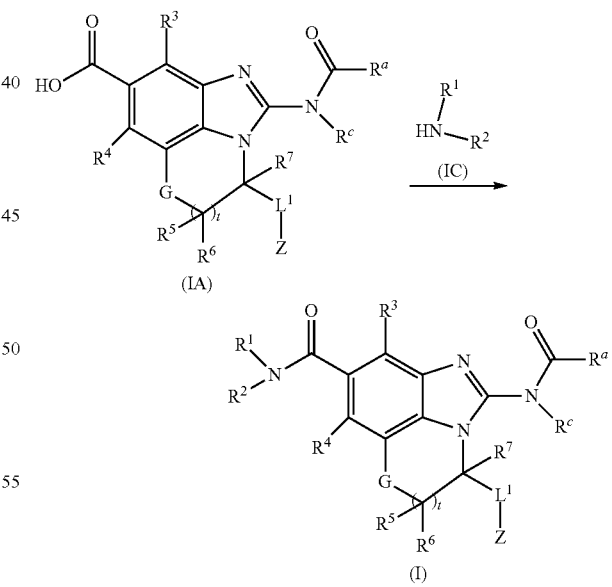

reacting a compound of formula (IA) with a compound of formula (IC) to obtain the compound of formula (I); wherein G, t, $R^a$, $R^e$, $R^1$ to $R^7$, $L^1$ and Z are each as defined in formula (I).

(2) A preparation process of a compound of formula (I) of the invention or a pharmaceutically acceptable salt, solvate, or prodrug thereof, comprising the following steps of:

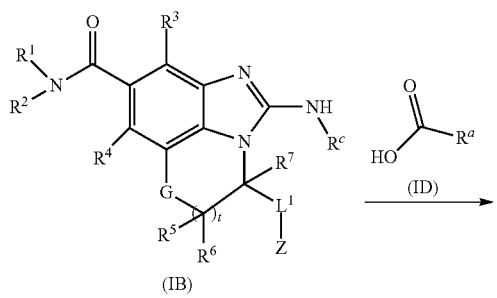
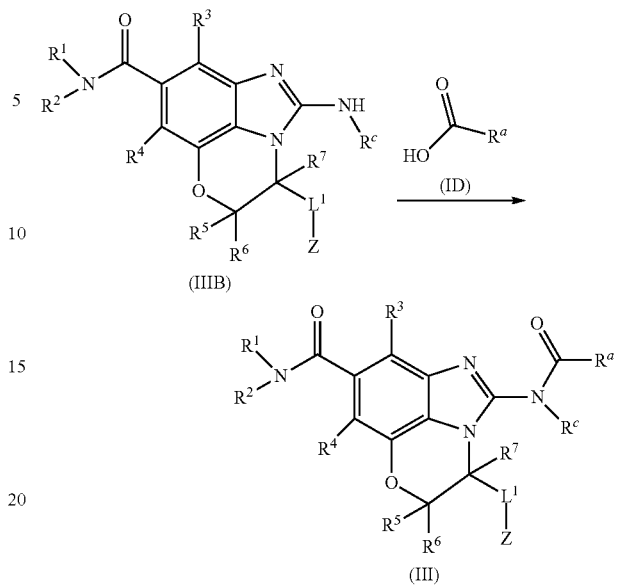

reacting a compound of formula (IB) with a compound of formula (ID) to obtain the compound of formula (I);

wherein G, t, $R^a$, $R^c$, $R^1$ to $R^7$, $L^1$ and Z are each as defined in formula (I).

(3) A preparation process of a compound of formula (III) of the invention or a pharmaceutically acceptable salt, solvate, or prodrug thereof, comprising the following steps of:

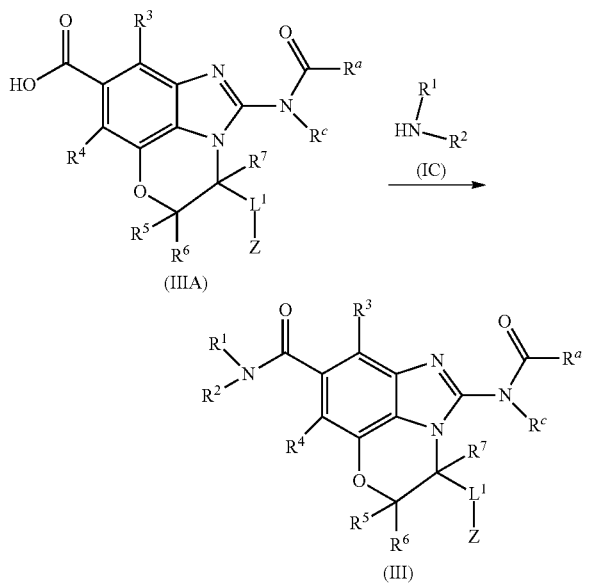

reacting a compound of formula (IIIA) with a compound of formula (IC) to obtain the compound of formula (III);

wherein $R^a$, $R^c$, $R^1$ to $R^7$, $L^1$ and Z are each as defined in formula (I).

(4) A preparation process of a compound or a salt of formula (III) of the invention, comprising the following steps of:

reacting a compound of formula (IIIB) with a compound of formula (ID) to obtain the compound of formula (III);

wherein $R^a$, $R^c$, $R^1$ to $R^7$, $L^1$ and Z are each as defined in formula (I).

The reaction The reaction of technical solutions (1) to (4) is preferably in solvent, wherein solvent used herein includes, but is not limited to, acetic acid, methanol, ethanol, toluene, tetrahydrofuran, dichloromethane, dimethylsulfoxide, 1,4-dioxane, water, N,N-dimethylformamide and the mixture thereof.

EXAMPLES

The following examples serve to illustrate the invention, but the examples should not be considered as limiting the scope of the invention. If specific conditions for the experimental method are not specified in the examples of the present invention, they are generally in accordance with conventional conditions or recommended conditions of the raw materials and the product manufacturer. The reagents without a specific source indicated are commercially available, conventional reagents.

The structure of each compound was identified by nuclear magnetic resonance (NMR) and/or mass spectrometry (MS). NMR chemical shifts (δ) were given in 10-6 (ppm). NMR was determined by a Bruker AVANCE-400 machine. The solvents were deuterated-dimethyl sulfoxide (DMSO-$d_6$), deuterated-chloroform (CDCl$_3$) and deuterated-methanol (CD$_3$OD), with tetramethylsilane (TMS) as an internal standard.

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

Chiral High performance liquid chromatography (HPLC) is determined on LC-10A vp (Shimadzu) or SFC-analytical (Berger Instruments Inc.)

MS is determined by a SHIMADZU (ESI) liquid chromatography-mass spectrometer (manufacturer: Shimadzu, type: LC-20AD, LCMS-2020).

The average rates of kinase inhibition, and the $IC_{50}$ values were determined by Microplate reader (BMG company, Germany).

The thin-layer silica gel plates used in thin-layer chromatography were Yantai Huanghai HSGF254 or Qingdao GF254 silica gel plate. The dimension of the plates used in TLC was 0.15 mm to 0.2 mm, and the dimension of the plates used in thin-layer chromatography for product purification was 0.4 mm to 0.5 mm.

Column chromatography generally used Yantai Huanghai 200 to 300 mesh or ISCO 230 to 400 mesh silica gel as carrier.

The known starting material of the invention can be prepared by the conventional synthesis method in the prior art, or can be purchased from ABCR GmbH & Co. KG, Acros Organics, Aldrich Chemical Company, Accela ChemBio Inc or Dari chemical Company, etc.

Unless otherwise stated in the examples, the following reactions were placed under argon atmosphere or nitrogen atmosphere.

The term "argon atmosphere" or "nitrogen atmosphere" means that a reaction flask was equipped with a balloon having 1 L of argon or nitrogen.

The term "hydrogen atmosphere" means that a reaction flask was equipped with a balloon having 1 L of hydrogen.

High pressure hydrogenation reactions were performed with a Parr 3916EKX hydrogenation apparatus and clear blue QL-500 hydrogen generator or HC2-SS hydrogenation apparatus.

In hydrogenation reactions, the reaction system was generally vacuumed and filled with hydrogen, and the above operation was repeated three times.

Microwave reactions were performed with a CEM Discover-S 908860 microwave reactor.

Unless otherwise stated in the examples, the solution used in following reactions refers to an aqueous solution.

Unless otherwise stated in the examples, the reaction temperature in the following reactions was room temperature.

Room temperature was the most proper reaction temperature, which was 20° C. to 30° C.

The reaction process is monitored by thin layer chromatography (TLC), and the developing solvent system includes: A: dichloromethane and methanol, B: hexane and ethyl acetate. The ratio of the volume of the solvent can be adjusted according to the polarity of the compounds. The elution system for purification of the compounds by column chromatography, thin layer chromatography and CombiFlash flash rapid preparation instrument includes: A: dichloromethane and methanol, B: hexane and ethyl acetate. The ratio of the volume of the solvent can be adjusted according to the polarity of the compounds, and sometimes a small amount of basic reagent such as ammonia or acidic reagent such as acetic acid can be added.

Final compounds are purified by Shimadzu (LC-20AD, SPD20A) Prepative HPLC (Phenomenex Gemini-NX 5 uM C18 21.2×100 mm column) with water/MeOH or water/$CH_3CN$ elution systems with optional additives, such as HCOOH and TFA.

The following abbreviations are used:
TEA is triethylamine,
HATU is 1-[Bis(dimethylamino)methylene]-1H-1,2,3-triazolo[4,5-b]pyridinium 3-oxide hexafluorophosphate
HBTU is O-(Benzotriazol-1-yl)-N,N,N',N'-tetramethyluronium hexafluorophosphate,
Cbz is —C(O)O-benzyl,
DCM is dichloromathene,
DMF is N,N-dimethylformamide,
DMSO is dimethyl sulfoxide,
DEAD is diethyl azodiformate,
EtOAc is ethyl acetate,
Prep HPLC is Prepative High performance liquid chromatography.
NMR is proton nuclear magnetic resonance, and
MS is mass spectroscopy with (+) referring to the positive mode which generally gives a M+1 (or M+H) absorption where M=the molecular mass.
TBDPSCl is tert-Butyl(chloro)diphenylsilane
DIPEA is N,N-Diisopropylethylamine
H-G II: Hoveyda-Grubbs Catalyst 2nd Generation Example 1

(S)-3-allyl-2-(1-ethyl-3-methyl-1H-pyrazole-5-carboxamido)-3,4-dihydro-5-oxa-1,2a-diazaacenaphthylene-7-carboxamide 1

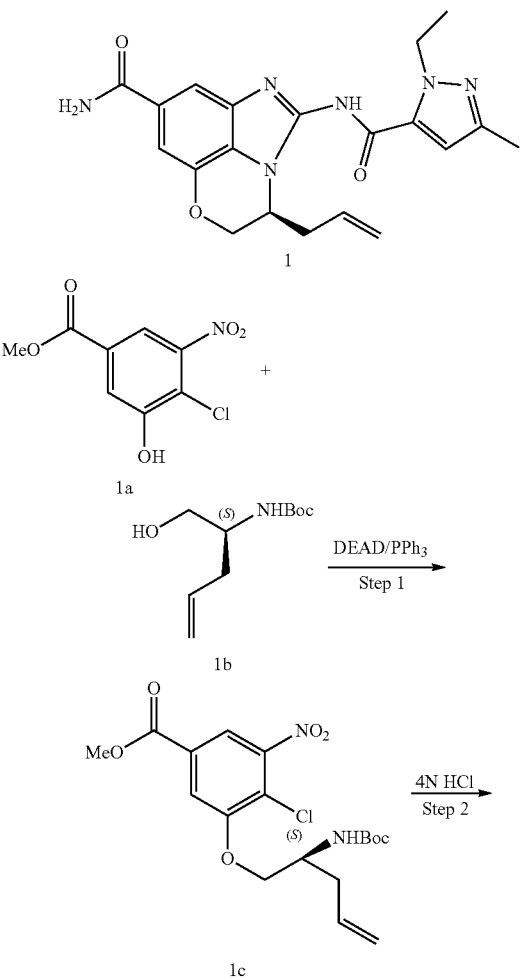

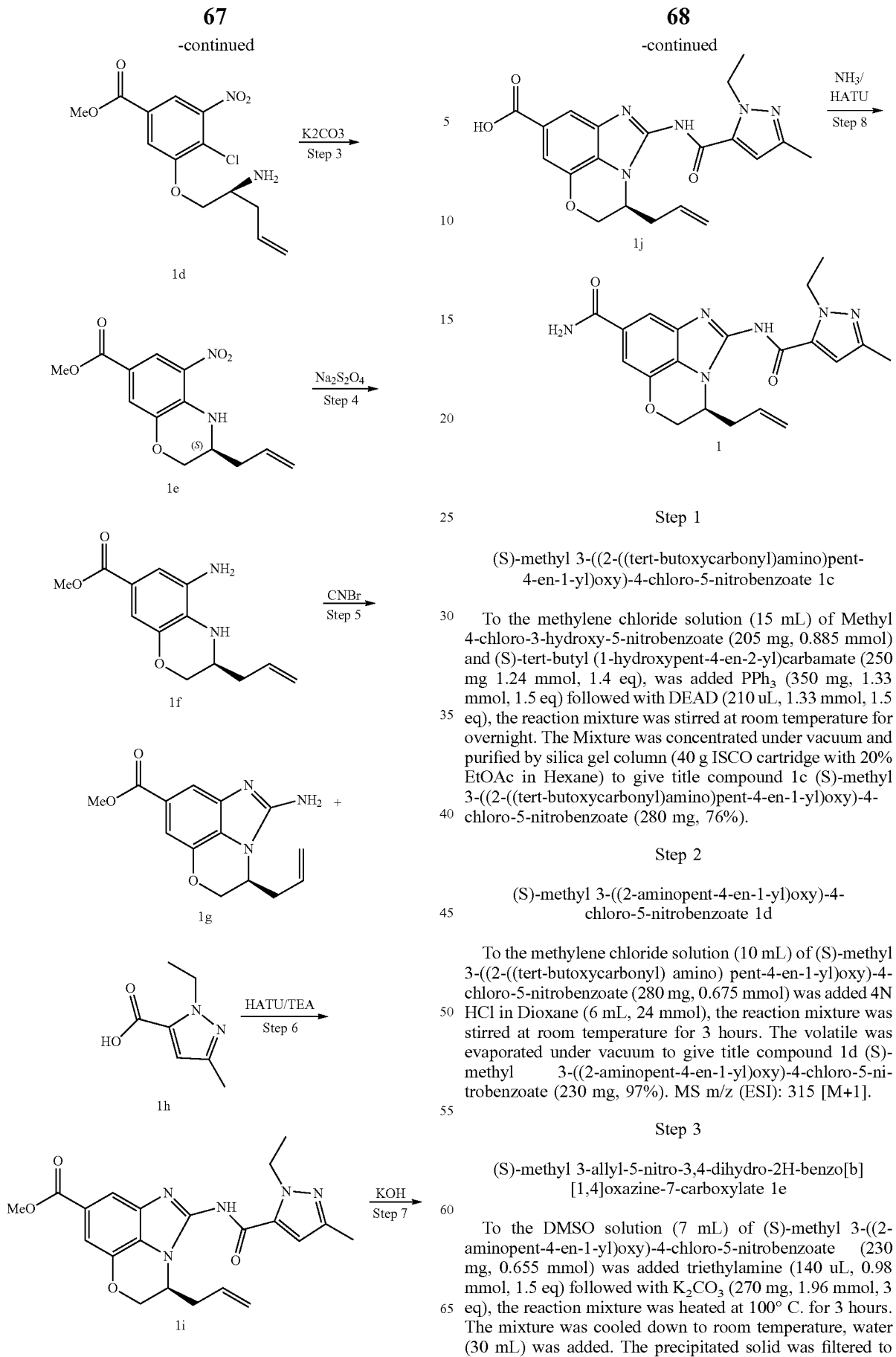

Step 1

(S)-methyl 3-((2-((tert-butoxycarbonyl)amino)pent-4-en-1-yl)oxy)-4-chloro-5-nitrobenzoate 1c To the methylene chloride solution (15 mL) of Methyl 4-chloro-3-hydroxy-5-nitrobenzoate (205 mg, 0.885 mmol) and (S)-tert-butyl (1-hydroxypent-4-en-2-yl)carbamate (250 mg 1.24 mmol, 1.4 eq), was added $PPh_3$ (350 mg, 1.33 mmol, 1.5 eq) followed with DEAD (210 uL, 1.33 mmol, 1.5 eq), the reaction mixture was stirred at room temperature for overnight. The Mixture was concentrated under vacuum and purified by silica gel column (40 g ISCO cartridge with 20% EtOAc in Hexane) to give title compound 1c (S)-methyl 3-((2-((tert-butoxycarbonyl)amino)pent-4-en-1-yl)oxy)-4-chloro-5-nitrobenzoate (280 mg, 76%).

Step 2

(S)-methyl 3-((2-aminopent-4-en-1-yl)oxy)-4-chloro-5-nitrobenzoate 1d

To the methylene chloride solution (10 mL) of (S)-methyl 3-((2-((tert-butoxycarbonyl) amino) pent-4-en-1-yl)oxy)-4-chloro-5-nitrobenzoate (280 mg, 0.675 mmol) was added 4N HCl in Dioxane (6 mL, 24 mmol), the reaction mixture was stirred at room temperature for 3 hours. The volatile was evaporated under vacuum to give title compound 1d (S)-methyl 3-((2-aminopent-4-en-1-yl)oxy)-4-chloro-5-nitrobenzoate (230 mg, 97%). MS m/z (ESI): 315 [M+1].

Step 3

(S)-methyl 3-allyl-5-nitro-3,4-dihydro-2H-benzo[b][1,4]oxazine-7-carboxylate 1e

To the DMSO solution (7 mL) of (S)-methyl 3-((2-aminopent-4-en-1-yl)oxy)-4-chloro-5-nitrobenzoate (230 mg, 0.655 mmol) was added triethylamine (140 uL, 0.98 mmol, 1.5 eq) followed with $K_2CO_3$ (270 mg, 1.96 mmol, 3 eq), the reaction mixture was heated at 100° C. for 3 hours. The mixture was cooled down to room temperature, water (30 mL) was added. The precipitated solid was filtered to give title compound 1e (S)-methyl 3-allyl-5-nitro-3,4-dihydro-2H-benzo[b][1,4]oxazine-7-carboxylate (120 mg, 66%). MS m/z (ESI): 279 [M+1].

Step 4

(S)-methyl 3-allyl-5-amino-3,4-dihydro-2H-benzo[b][1,4]oxazine-7-carboxylate 1f

To the MeOH solution (15 mL) of (S)-methyl 3-allyl-5-nitro-3,4-dihydro-2H-benzo[b][1,4]oxazine-7-carboxylate (120 mg, 0.431 mmol) was added $Na_2S_2O_4$ (751 mg, 4.31 mmol, 10 eq) in 5 mL water, followed with conc. $NH_4OH$ (0.78 mL, 10.8 mmol), the reaction mixture was stirred at room temperature for 1 hour. The mixture was diluted with water (20 mL), extracted with EtOAc (30 mL×3). Organic layer was combined, washed with brine (20 mL×1), dried over $Na_2SO_4$, filtered and the filtrated was concentrated under vacuum to give crude title compound 1f (S)-methyl 3-allyl-5-amino-3,4-dihydro-2H-benzo[b][1,4]oxazine-7-carboxylate (118 mg, 100%), which was used in the next step without further purification.

MS m/z (ESI): 249 [M+1].

Step 5

(S)-methyl 3-allyl-2-amino-3,4-dihydro-5-oxa-1,2a-diazaacenaphthylene-7-carboxylate 1g To the MeOH solution (20 mL) of (S)-methyl 3-allyl-5-amino-3,4-dihydro-2H-benzo[b][1,4]oxazine-7-carboxylate (120 mg, 0.475 mmol) was added BrCN (76 mg, 0.713 mmol, 2 eq), the reaction mixture was stirred at room temperature for overnight. The mixture was concentrated under vacuum to give crude title compound 1g (S)-methyl 3-allyl-2-amino-3,4-dihydro-5-oxa-1,2a-diazaacenaphthylene-7-carboxylate (160 mg, 95%), which was used in the next step without further purification. MS m/z (ESI): 274 [M+1].

Step 6

(S)-methyl 3-allyl-2-(1-ethyl-3-methyl-1H-pyrazole-5-carboxamido)-3,4-dihydro-5-oxa-1,2a-diazaacenaphthylene-7-carboxylate 1i To the DCM (~15 mL) and DMF (3 mL) solution of (S)-methyl 3-allyl-2-amino-3,4-dihydro-5-oxa-1,2a-diazaacenaphthylene-7-carboxylate (160 mg, 0.463 mmol) was added 1-ethyl-3-methyl-1H-pyrazole-5-carboxylic acid (107 mg, 0.694 mmol, 1.5 eq), HATU (264 mg, 0.694 mmol, 1.5 eq) and TEA (325 uL, 2.32 mmol, 5 eq) the reaction mixture was stirred at room temperature for overnight. LC-Mass showed ~25% SM exist, another 0.5 eq (36 mg, 0.232 mmol) (S)-methyl 3-allyl-2-amino-3,4-dihydro-5-oxa-1,2a-diazaacenaphthylene-7-carboxylate, HATU (88 mg, 0.232 mmol) was added and the mixture was stirred at room temperature for overnight. The mixture was diluted with DCM (30 mL), washed with water (10 mL×1), dried over $Na_2SO_4$, filtered and the filtrated was concentrated under vacuum. The residue was purified by silica gel column (24 g ISCO cartridge with 10% EtOH and 30% EtOAc in Hexane) to give title compound 1i (S)-methyl 3-allyl-2-(1-ethyl-3-methyl-1H-pyrazole-5-carboxamido)-3,4-dihydro-5-oxa-1,2a-diazaacenaphthylene-7-carboxylate (150 mg, 80%).

MS m/z (ESI): 410 [M+1].

Step 7

(S)-3-allyl-2-(1-ethyl-3-methyl-1H-pyrazole-5-carboxamido)-3,4-dihydro-5-oxa-1,2a-diazaacenaphthylene-7-carboxylic acid 1j To the MeOH solution (1.5 mL) of (S)-methyl 3-allyl-2-(1-ethyl-3-methyl-1H-pyrazole-5-carboxamido)-3,4-dihydro-5-oxa-1,2a-diazaacenaphthylene-7-carboxylate (10 mg, 0.024 mmol) was added 5N KOH aqueous solution (1.5 mL, 7.5 mmol, 30 eq), the reaction mixture was stirred at room temperature for overnight. The mixture was acidified by 6N HCl to pH<5, diluted with water (10 mL), extracted with EtOAc (10 mL×3). Organic layer was combined, washed with brine (10 mL×1), dried over $Na_2SO_4$, filtered and the filtrate was concentrated under vacuum to give crude title compound 1j (S)-3-allyl-2-(1-ethyl-3-methyl-1H-pyrazole-5-carboxamido)-3,4-dihydro-5-oxa-1,2a-diazaacenaphthylene-7-carboxylic acid (12 mg, 100%), which was used in the next step without further purification.

MS m/z (ESI): 396 [M+1].

Step 8

(S)-3-allyl-2-(1-ethyl-3-methyl-1H-pyrazole-5-carboxamido)-3,4-dihydro-5-oxa-1,2a-diazaacenaphthylene-7-carboxamide 1

To the DMF (1 mL) solution of (S)-3-allyl-2-(1-ethyl-3-methyl-1H-pyrazole-5-carboxamido)-3,4-dihydro-5-oxa-1,2a-diazaacenaphthylene-7-carboxylic acid (12 mg, 0.024 mmol) was added 7N ammonia in MeOH (50 uL, 0.35 mmol, 12 eq), HATU (17.3 mg, 0.046 mmol, 1.5 eq) and TEA (12.6 uL, 0.09 mmol, 3 eq) the reaction mixture was stirred at room temperature for 2 hr. The mixture was purified by reverse phase HPLC, eluated with $AcCN/H_2O/HCOOH$ to give title compound 1 (S)-3-allyl-2-(1-ethyl-3-methyl-1H-pyrazole-5-carboxamido)-3,4-dihydro-5-oxa-1,2a-diazaacenaphthylene-7-carboxamide (2.2 mg, 23%).

MS m/z (ESI): 395 [M+1].

Example 2

2-(1-ethyl-3-methyl-1H-pyrazole-5-carboxamido)-3,4-dihydro-5-oxa-1,2a-diazaacenaphthylene-7-carboxamide 2

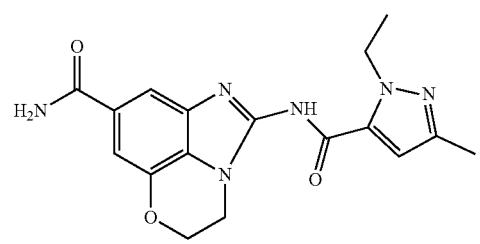

Examples 2 was prepared with the similar procedures as Example 1.

MS m/z (ESI): 355 [M+1].

Example 3
2-(1-ethyl-N,3-dimethyl-1H-pyrazole-5-carboxamido)-3,4-dihydro-5-oxa-1,2a-diazaacenaphthylene-7-carboxamide 3
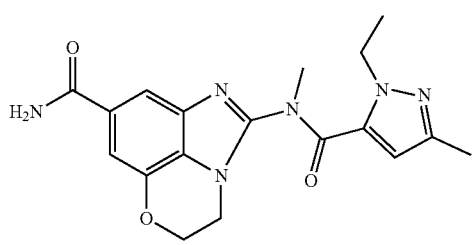
Examples 3 was prepared with the similar procedures as Example 1.
MS m/z (ESI): 369 [M+1].
Example 4
(S)-benzyl (3-(7-carbamoyl-2-(1-ethyl-3-methyl-1H-pyrazole-5-carboxamido)-3,4-dihydro-5-oxa-1,2a-diazaacenaphthylen-3-yl)propyl)carbamate 4
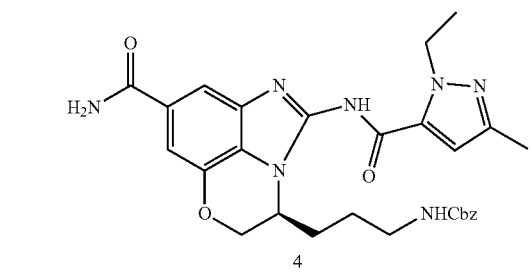
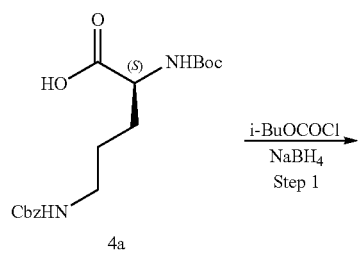
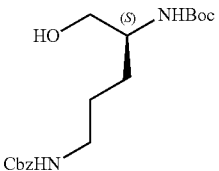
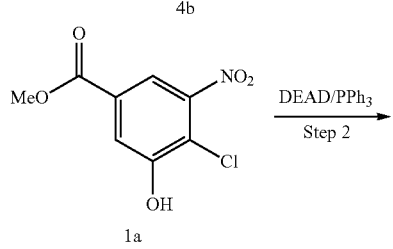
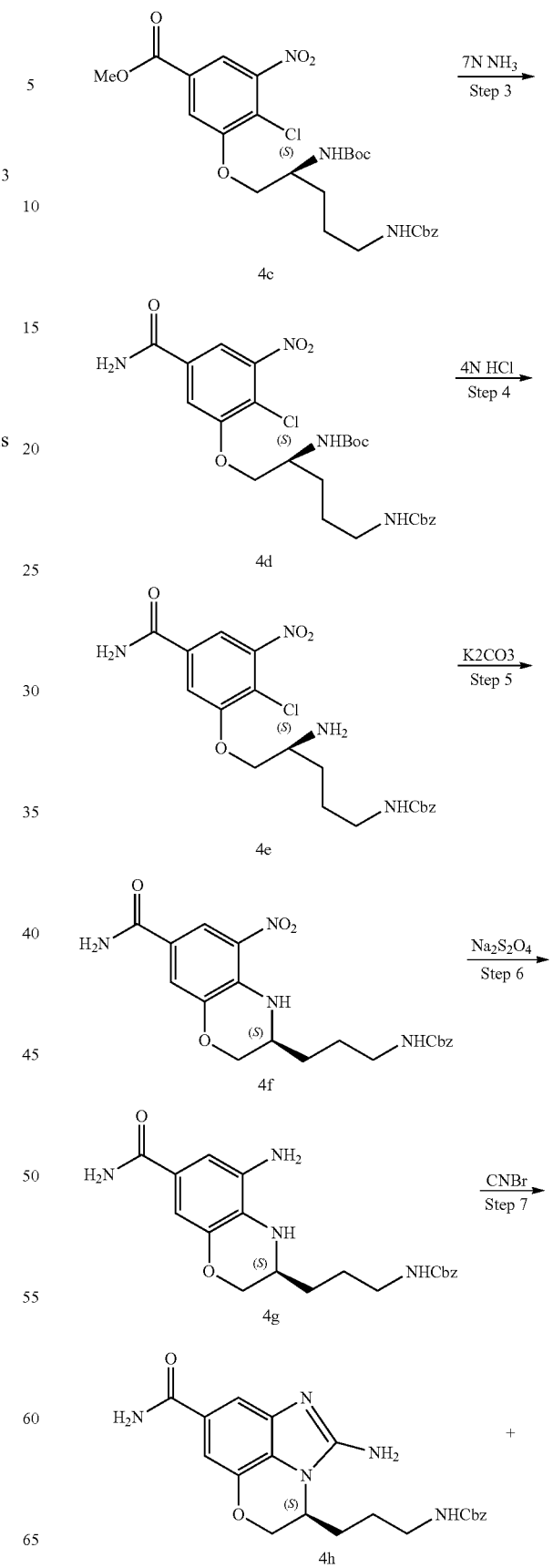

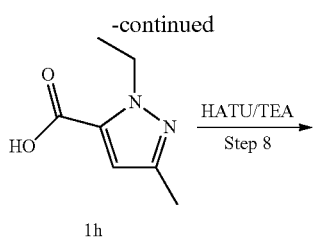

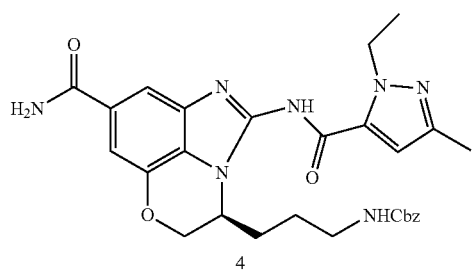

Step 1

(S)-benzyl tert-butyl (5-hydroxypentane-1,4-diyl)dicarbamate 4b

To the THF (15 mL) solution of Boc-Orn-Z—OH (0.935 g, 2.55 mmol) at 0° C. ice-water bath, was added Triethylamine (395 uL, 2.81 mmol, 1.1 eq), followed with i-BuO-COCl (380 uL, 2.81 mmol, 1.1 eq). The mixture was stirred at 0° C. for 10 min, then NaBH$_4$ (290 mg, 7.66 mmol, 3 eq) in 2 mL MeOH was added at 0° C. The mixture was stirred at 0° C. for 30 min. The Mixture was diluted with water (50 mL), extracted with EtOAc (30 mL×3). Organic layer was combined, washed with 2N NaOH (20 mL×1), brine (20 mL×1), dried over Na$_2$SO$_4$, filtered and the filtrate was concentrated under vacuum to give crude title compound 4b (S)-benzyl tert-butyl (5-hydroxypentane-1,4-diyl)dicarbamate, which was used in the next step without further purification.

Step 2

(S)-methyl 3-((5-(((benzyloxy)carbonyl)amino)-2-((tert-butoxycarbonyl) amino)pentyl)oxy)-4-chloro-5-nitrobenzoate 4c To the methylene chloride solution (25 mL) of Methyl 4-chloro-3-hydroxy-5-nitrobenzoate (205 mg, 1.68 mmol) and (S)-benzyl tert-butyl (5-hydroxypentane-1,4-diyl)dicarbamate (888 mg 2.52 mmol, 1.5 eq), was added PPh$_3$ (660 mg, 2.52 mmol, 1.5 eq) followed with DEAD (397 uL, 2.52 mmol, 1.5 eq), the reaction mixture was stirred at room temperature for overnight. The mixture was diluted with 20 mL DCM, washed with 0.5 N NaOH aqueous solution (15 mL×1) to remove unreacted phenol, followed by washing with brine (20 mL×1), dried over Na$_2$SO$_4$, filtered and the filtrate was concentrated under vacuum. The residue was purified by silica gel column (40 g ISCO cartridge with 30% EtOAc in Hexane) to give title compound 4c (S)-methyl 3-((5-(((benzyloxy)carbonyl)amino)-2-((tert-butoxycarbonyl)amino)pentyl)oxy)-4-chloro-5-nitrobenzoate (740 mg, 78%). MS m/z (ESI): 566 [M+1].

Step 3

(S)-benzyl tert-butyl (5-(5-carbamoyl-2-chloro-3-nitrophenoxy)pentane-1,4-diyl)dicarbamate 4d To the sealed tube charged with (S)-methyl 3-((5-(((benzyloxy)carbonyl)amino)-2-((tert-butoxycarbonyl)amino)pentyl)oxy)-4-chloro-5-nitrobenzoate (140 mg, 0.247 mmol), was added 7N Ammonia in MeOH (10 mL, 70 mmol). The reaction mixture was heated at 60° C. for 3 hr, another 5 mL 7N Ammonia in MeOH was added and heated at 60° C. for 1.5 hr, then additional 3 mL 7N NH$_3$ in MeOH was then added and heated at 60° C. for overnight. LC-Mass showed reaction done. The volatile was evaporated under vacuum to give title compound (S)-benzyl tert-butyl (5-(5-carbamoyl-2-chloro-3-nitrophenoxy)pentane-1,4-diyl)dicarbamate 4d, which was used in the next step without further purification. (140 mg, 100%). MS m/z (ESI): 551 [M+1].

Step 4

(S)-benzyl (4-amino-5-(5-carbamoyl-2-chloro-3-nitrophenoxy)pentyl)carbamate 4e

To the methylene chloride solution (~5 mL) of (S)-benzyl tert-butyl (5-(5-carbamoyl-2-chloro-3-nitrophenoxy)pentane-1,4-diyl)dicarbamate (140 mg, 0.254 mmol) was added 4N HCl in Dioxane (6 mL, 24 mmol), the reaction mixture was stirred at room temperature for 1 hour. The volatile was evaporated under vacuum to give title compound 4e (S)-benzyl (4-amino-5-(5-carbamoyl-2-chloro-3-nitrophenoxy)pentyl)carbamate (140 mg, 100%), which was used in the next step without further purification. MS m/z (ESI): 451 [M+1].

Step 5

(S)-benzyl (3-(7-carbamoyl-5-nitro-3,4-dihydro-2H-benzo[b][1,4]oxazin-3-yl) propyl) carbamate 4f To the DMSO solution (~3 mL) of (S)-benzyl (4-amino-5-(5-carbamoyl-2-chloro-3-nitrophenoxy)pentyl)carbamate (140 mg, 0.254 mmol) was added Triethylamine (72 uL, 0.508 mmol, 2 eq) followed with K$_2$CO$_3$ (105 mg, 0.762 mmol, 3 eq), the reaction mixture was heated at 120° C. for 2 hours. The Mixture was cooled down to room temperature, water (~10 mL) was added, mixture was extracted with DCM (10 mL×2), EtOAc (10 mL×2), Organic layer was combined, dried over Na$_2$SO$_4$, filtered and the filtrate was concentrated under vacuum. The residue was purified by silica gel column (12 g ISCO cartridge, eluted with 15% EtOH and 45% EtOAc in Hexane) to give title compound 4f (S)-benzyl (3-(7-carbamoyl-5-nitro-3,4-dihydro-2H-benzo[b][1,4]oxazin-3-yl)propyl)carbamate (84 mg, 80%). MS m/z (ESI): 415 [M+1].

Step 6

(S)-benzyl (3-(5-amino-7-carbamoyl-3,4-dihydro-2H-benzo[b][1,4]oxazin-3-yl)propyl)carbamate 4g To the MeOH solution (~3 mL) of (S)-benzyl (3-(7-carbamoyl-5-nitro-3,4-dihydro-2H-benzo[b][1,4]oxazin-3-yl)propyl)carbamate (84 mg, 0.2 mmol) was added $Na_2S_2O_4$ (350 mg, 2.0 mmol, 10 eq) in 1 mL water, followed with conc. $NH_4OH$ (0.5 mL, 7 mmol), the reaction mixture was stirred at room temperature for 1 hour. The Mixture was diluted with water (10 mL), extracted with EtOAc (10 mL×3). Organic layer was combined, washed with brine (10 mL×1), dried over $Na_2SO_4$, filtered and the filtrated was concentrated under vacuum to give crude title compound 4g (S)-benzyl (3-(5-amino-7-carbamoyl-3,4-dihydro-2H-benzo[b][1,4]oxazin-3-yl)propyl)carbamate (35 mg, 45%), which was used in the next step without further purification. MS m/z (ESI): 385 [M+1].

Step 7

(S)-benzyl (3-(2-amino-7-carbamoyl-3,4-dihydro-5-oxa-1,2a-diazaacenaphthylen-3-yl) propyl)carbamate 4h To the MeOH solution (5 mL) of (S)-benzyl (3-(5-amino-7-carbamoyl-3,4-dihydro-2H-benzo[b][1,4]oxazin-3-yl) propyl)carbamate (35 mg, 0.09 mmol) was added BrCN (60 mg, 0.18 mmol, 6 eq), the reaction mixture was stirred at room temperature for overnight. The Mixture was concentrated under vacuum to give crude title compound 4h (S)-benzyl (3-(2-amino-7-carbamoyl-3,4-dihydro-5-oxa-1,2a-diazaacenaphthylen-3-yl)propyl)carbamate (40 mg, 100%), which was used in the next step without further purification. MS m/z (ESI): 410 [M+1].

Step 8

(S)-benzyl (3-(7-carbamoyl-2-(1-ethyl-3-methyl-1H-pyrazole-5-carboxamido)-3,4-dihydro-5-oxa-1,2a-diazaacenaphthylen-3-yl)propyl)carbamate 4

To the DCM (3 mL) and DMF (1 mL) solution of (S)-benzyl (3-(2-amino-7-carbamoyl-3,4-dihydro-5-oxa-1,2a-diazaacenaphthylen-3-yl)propyl)carbamate (40 mg, 0.09 mmol) was added 1-ethyl-3-methyl-1H-pyrazole-5-carboxylic acid (21 mg, 0.136 mmol, 1.5 eq), HATU (52 mg, 0.136 mmol, 1.5 eq) and TEA (64 uL, 0.453 mmol, 5 eq) the reaction mixture was stirred at room temperature for 2 hr. LC-Mass showed major diamide. The mixture was diluted with DCM (20 mL), washed with water (10 mL×1), dried over $Na_2SO_4$, filtered and the filtrate was concentrated under vacuum. The residue was dissolved in 1 mL MeOH, added with 1.5 mL KOH aq. Solution, heated at 60° C. for 1 hr. LC-Mass showed desired product. The mixture was purified by reverse phase HPLC, eluated with AcCN/H2O/HCOOH to give title compound (S)-benzyl (3-(7-carbamoyl-2-(1-ethyl-3-methyl-1H-pyrazole-5-carboxamido)-3,4-dihydro-5-oxa-1,2a-diazaacenaphthylen-3-yl)propyl)carbamate 4 (20 mg, 40%). MS m/z (ESI): 546 [M+1].

Example 5

3-(but-2-en-1-yl)-2-(1-ethyl-3-methyl-1H-pyrazole-5-carboxamido)-3,4-dihydro-5-oxa-1,2a-diazaacenaphthylene-7-carboxamide 5

(R,E)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-1

(S,Z)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-2

(S,E)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-3

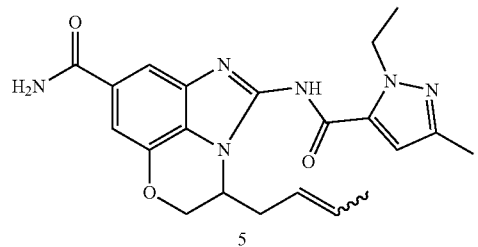

5

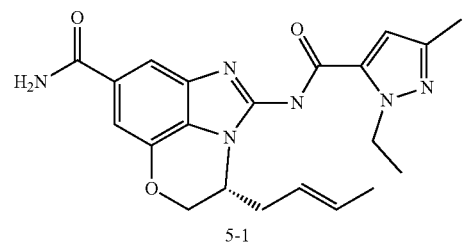

5-1

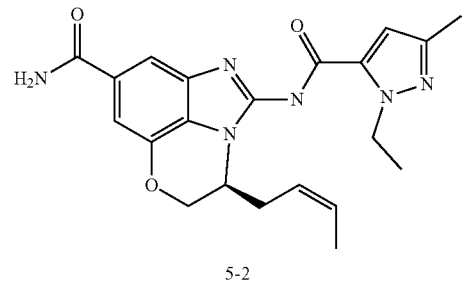

5-2

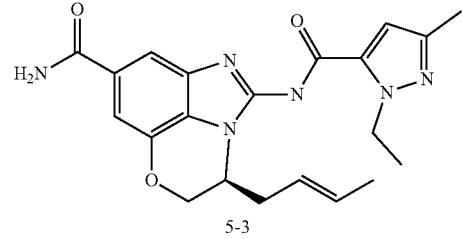

5-3

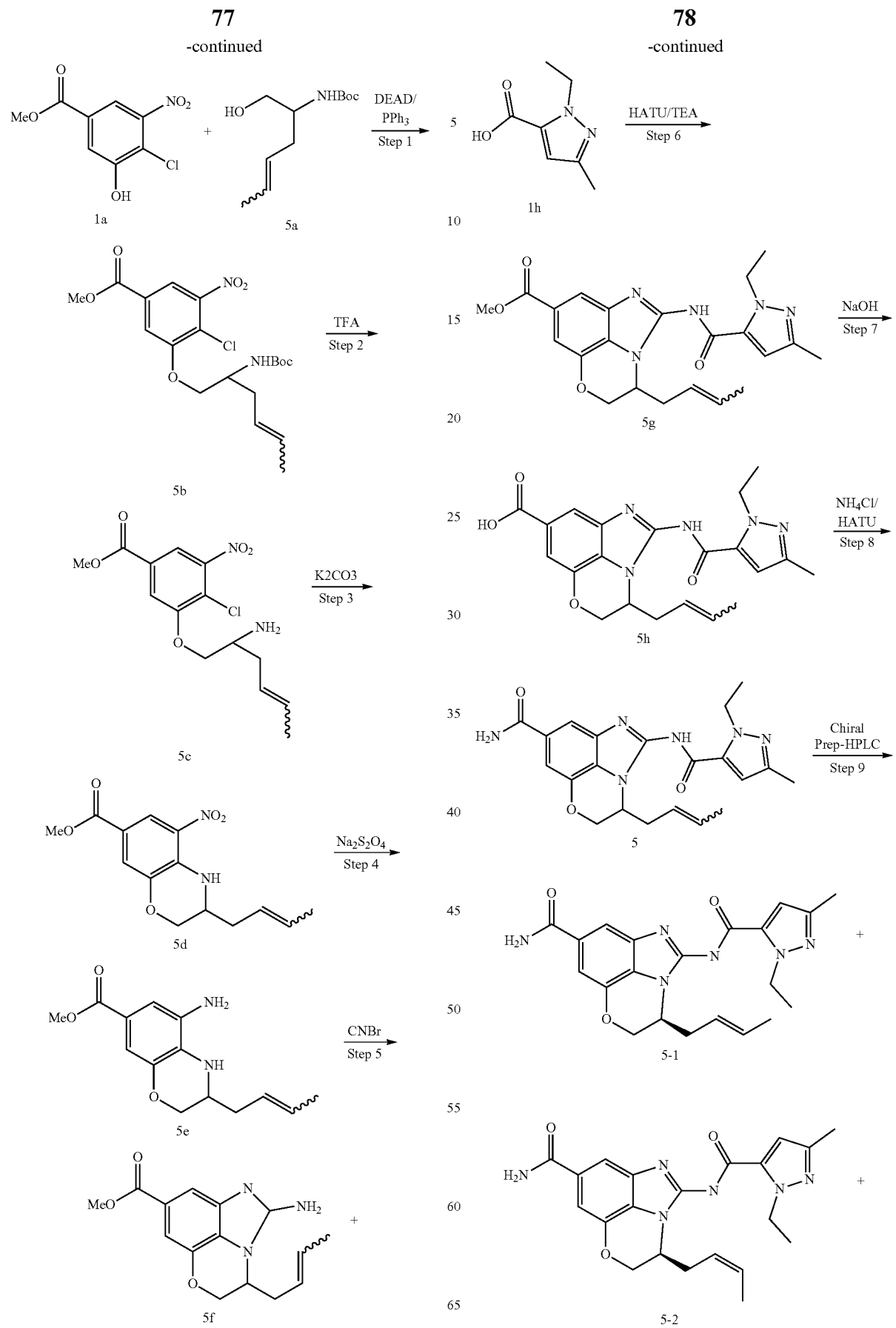

-continued

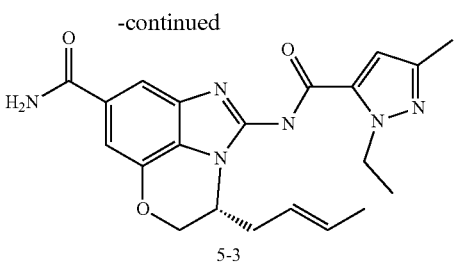

5-3

Step 1

Methyl 3-((2-((tert-butoxycarbonyl)amino)hex-4-en-1-yl)oxy)-4-chloro-5-nitrobenzoate 5b To the tetrahydrofuran solution (40 mL) of Methyl 4-chloro-3-hydroxy-5-nitrobenzoate 1a (689 mg, 2.98 mmol) and PPh$_3$ (1.09 g, 4.18 mmol, 1.4 eq) under nitrogen atmosphere at room temperature was added DEAD (0.70 mL, 4.47 mmol, 1.5 eq). The resulting solution was stirred at room temperature for 1 hour before addition of tert-butyl (1-hydroxyhex-4-en-2-yl)carbamate 5a (900 mg, 4.18 mmol, 1.4 eq). The reaction mixture was stirred overnight at room temperature. The mixture was concentrated under vacuum and purified by silica gel column (80 g ISCO cartridge with 0-50% EtOAc in Hexanes) to give title compound 5b methyl 3-((2-((tert-butoxycarbonyl)amino)hex-4-en-1-yl)oxy)-4-chloro-5-nitrobenzoate (1.21 g, 94%).

Step 2

Methyl 3-((2-aminohex-4-en-1-yl)oxy)-4-chloro-5-nitrobenzoate 5c

To the methylene chloride solution (30 mL) of methyl 3-((2-((tert-butoxycarbonyl)amino)hex-4-en-1-yl)oxy)-4-chloro-5-nitrobenzoate 5b (1.21 g, 2.82 mmol) was added trifluoroacetic acid (3 mL), the reaction mixture was stirred at room temperature for 3 hours. The volatile was evaporated under vacuum to give title compound methyl 3-((2-aminohex-4-en-1-yl)oxy)-4-chloro-5-nitrobenzoate 5c. The crude was used for next step without further purification. MS m/z (ESI): 329 [M+1].

Step 3

Methyl 3-(but-2-en-1-yl)-5-nitro-3,4-dihydro-2H-benzo[b][1,4]oxazine-7-carboxylate 5d To the dimethylformamide solution (20 mL) of methyl 3-((2-aminohex-4-en-1-yl)oxy)-4-chloro-5-nitrobenzoate 5c (Crude, 2.80 mmol) was added triethylamine (0.62 mL, 4.47 mmol, 1.6 eq) followed with K$_2$CO$_3$ (822 mg, 5.96 mmol, 2.2 eq). The reaction mixture was heated at 100° C. for 3 hours. The mixture was cooled down to room temperature. The mixture was concentrated under vacuum and purified by silica gel column (80 g ISCO cartridge with 0-100% EtOAc in Hexane) to give title compound methyl 3-(but-2-en-1-yl)-5-nitro-3,4-dihydro-2H-benzo[b][1,4]oxazine-7-carboxylate 5d (780 mg, 94%, two steps). MS m/z (ESI): 293 [M+1].

Step 4

Methyl 5-amino-3-(but-2-en-1-yl)-3,4-dihydro-2H-benzo[b][1,4]oxazine-7-carboxylate 5e To the MeOH solution (50 mL) of Methyl 3-(but-2-en-1-yl)-5-nitro-3,4-dihydro-2H-benzo[b][1,4]oxazine-7-carboxylate 5d (940 mg, 3.22 mmol) was added Na$_2$S$_2$O$_4$ (5.6 g, 32.2 mmol, 10 eq) in 25 mL water, followed with conc. NH$_4$OH (3.2 mL, 80.47 mmol, 25 eq). The reaction mixture was stirred at room temperature for 2 hours. The mixture was diluted with brine (50 mL), extracted with EtOAc (50 mL×3). The organic layer was combined, dried over Na$_2$SO$_4$ and filtered. The solvent was concentrated under vacuum to give methyl 5-amino-3-(but-2-en-1-yl)-3,4-dihydro-2H-benzo[b][1,4]oxazine-7-carboxylate 5e, which was used in the next step without further purification. MS m/z (ESI): 263 [M+1].

Step 5

Methyl 2-amino-3-(but-2-en-1-yl)-3,4-dihydro-5-oxa-1,2a-diazaacenaphthylene-7-carboxylate 5f To the MeOH solution (20 mL) of Methyl 5-amino-3-(but-2-en-1-yl)-3,4-dihydro-2H-benzo[b][1,4]oxazine-7-carboxylate 5e (Crude, 3.22 mmol) was added BrCN (852 mg, 8.05 mmol, 2.5 eq). The reaction mixture was stirred overnight at room temperature. The mixture was concentrated under vacuum to give crude title compound methyl 2-amino-3-(but-2-en-1-yl)-3,4-dihydro-5-oxa-1,2a-diazaacenaphthylene-7-carboxylate 5f. The crude was used in the next step without further purification. MS m/z (ESI): 288 [M+1].

Step 6

Methyl 3-(but-2-en-1-yl)-2-(1-ethyl-3-methyl-1H-pyrazole-5-carboxamido)-3,4-dihydro-5-oxa-1,2a-diazaacenaphthylene-7-carboxylate 5g To the DMF (20 mL) solution of methyl 2-amino-3-(but-2-en-1-yl)-3,4-dihydro-5-oxa-1,2a-diazaacenaphthylene-7-carboxylate 5f (Crude, 3.22 mmol) was added 1-ethyl-3-methyl-1H-pyrazole-5-carboxylic acid (744 mg, 4.83 mmol, 1.5 eq), HATU (1.84 g, 4.83 mmol, 1.5 eq) and TEA (2.24 mL, 3.01 mmol, 5 eq). The reaction mixture was stirred at room temperature for overnight. The mixture was diluted with EtOAc (50 mL), washed with brine (50 mL×3), dried over Na$_2$SO$_4$ and filtered. The organic solvent was concentrated under vacuum and the residue was purified by silica gel column (80 g ISCO cartridge with 0-80% EtOAc in Hexane) to give title compound methyl 3-(but-2-en-1-yl)-2-(1-ethyl-3-methyl-1H-pyrazole-5-carboxamido)-3,4-dihydro-5-oxa-1,2a-diazaacenaphthylene-7-carboxylate 5g (966 mg, 70%, three steps). MS m/z (ESI): 424 [M+1].

Step 7

3-(but-2-en-1-yl)-2-(1-ethyl-3-methyl-1H-pyrazole-5-carboxamido)-3,4-dihydro-5-oxa-1,2a-diazaacenaphthylene-7-carboxylic acid 5h To the MeOH solution (15 mL) of methyl 3-(but-2-en-1-yl)-2-(1-ethyl-3-methyl-1H-pyrazole-5-carboxamido)-3,4- dihydro-5-oxa-1,2a-diazaacenaphthylene-7-carboxylate 5g (725 mg) was added Sat NaOH aqueous solution (6 mL). The reaction mixture was stirred at room temperature for overnight. The mixture was acidified by TFA at 0° C., and then purified by prep-HPLC, The mixture was acidified by TFA at 0° C., and then purified by prep-HPLC, eluated with AcCN/H$_2$O/TFA to give title compound 3-(but-2-en-1-yl)-2-(1-ethyl-3-methyl-1H-pyrazole-5-carboxamido)-3,4-dihydro-5-oxa-1,2a-diazaacenaphthylene-7-carboxylic acid 5h (349 mg, 50%). MS m/z (ESI): 410 [M+1].

Step 8

3-(but-2-en-1-yl)-2-(1-ethyl-3-methyl-1H-pyrazole-5-carboxamido)-3,4-dihydro-5-oxa-1,2a-diazaacenaphthylene-7-carboxamide 5

To the DMF (15 mL) solution of 3-(but-2-en-1-yl)-2-(1-ethyl-3-methyl-1H-pyrazole-5-carboxamido)-3,4-dihydro-5-oxa-1,2a-diazaacenaphthylene-7-carboxylic acid 5h (349 mg, 0.85 mmol) was added NH$_4$Cl (1.1 g), HATU (650 mg, 1.72 mmol, 2 eq) and TEA (0.36, 1.72 mmol, 3 eq). The reaction mixture was stirred at room temperature for 2 hrs. The mixture was acidified by TFA at 0° C., and then purified by prep-HPLC, eluated with AcCN/H$_2$O/TFA to give title compound 3-(but-2-en-1-yl)-2-(1-ethyl-3-methyl-1H-pyrazole-5-carboxamido)-3,4-dihydro-5-oxa-1,2a-diazaacenaphthylene-7-carboxamide 5 (183 mg, 53%). MS m/z (ESI): 409 [M+1]. 1H NMR (400 MHz, MeOD): δ 7.59 (s, 1H), 7.33 (s, 1H), 6.71 (s, 1H), 5.57-5.45 (m, 2H), 4.86-4.66 (m, 4H), 4.32-4.27 (m, 1H), 2.59-2.54 (m, 2H), 2.26 (s, 3H), 1.57 (d, J=6.0 Hz, 3H), 1.43 (t, J=7.2 Hz, 3H).

Step 9

(R,E)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-1

(S,Z)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-2

(S,E)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-3

The compound 5 was separated by Chiral Prep-HPLC chromatography to afford (R,E)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-1 (250 mg, off-white solid); (S,Z)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-2 (50 mg, off-white solid); (S,E)-3-(but-2-en-1-yl)-2-(1-ethyl-3-methyl-1H-pyrazole-5-carboxamido)-3,4-dihydro-5-oxa-1,2a-diazaacenaphthylene-7-carboxamide 5-3 (300 mg, off-white solid).

5-1: $^1$H NMR (400 MHz, MeOD): δ 7.60 (s, 1H), 7.33 (d, J=0.8 Hz, 1H), 6.71 (s, 1H), 5.61-5.43 (m, 2H), 4.86-4.66 (m, 4H), 4.32-4.25 (m, 1H), 2.60-2.56 (m, 2H), 2.26 (s, 3H), 1.57 (d, J=6.0 Hz, 3H), 1.44 (t, J=7.2 Hz, 3H).

HPLC: 99.676%@214 nm, 99.620%@254 nm.

Chiral HPLC: ee: 95.70%, Rt: 3.521 min.

MS m/z (ESI): 409.3 [M+H].

5-2: $^1$H NMR (400 MHz, MeOD): δ 7.60 (s, 1H), 7.34 (d, J=0.8 Hz, 1H), 6.71 (s, 1H), 5.62-5.58 (m, 2H), 4.70-4.63 (m, 4H), 4.30 (brd, J=10.0 Hz, 1H), 2.73-2.68 (m, 2H), 2.25 (s, 3H), 1.56 (d, J=6.0 Hz, 3H), 1.43 (t, J=7.2 Hz, 3H).

HPLC: 99.166%@214 nm, 99.139%@254 nm.

Chiral HPLC: ee: 100%, Rt: 7.538 min.

MS m/z (ESI): 409.3 [M+H].

5-3: $^1$H NMR (400 MHz, MeOD): δ 7.59 (s, 1H), 7.33 (d, J=0.8 Hz, 1H), 6.71 (s, 1H), 5.61-5.44 (m, 2H), 4.75-4.64 (m, 4H), 4.29 (dd, J=12.0 Hz, 2.8 Hz, 1H), 2.60-2.54 (m, 2H), 2.26 (s, 3H), 1.57 (d, J=6.0 Hz, 3H), 1.43 (t, J=7.2 Hz, 3H).

HPLC: 99.394%@214 nm, 99.600%@254 nm.

Chiral HPLC: ee: 100%, Rt: 9.942 min.

MS m/z (ESI): 409.3 [M+H].

Example 6

(R)-3-allyl-2-(1-ethyl-3-methyl-1H-pyrazole-5-carboxamido)-3,4-dihydro-5-oxa-1,2a-diazaacenaphthylene-7-carboxamide 6

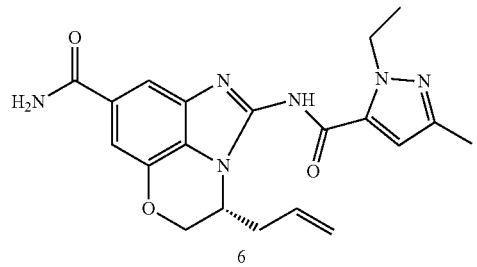

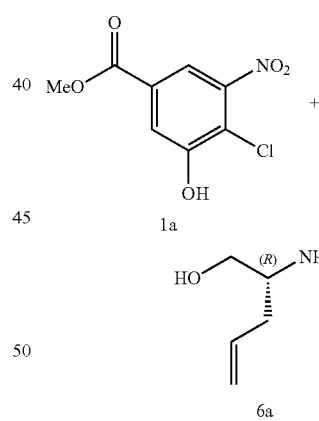

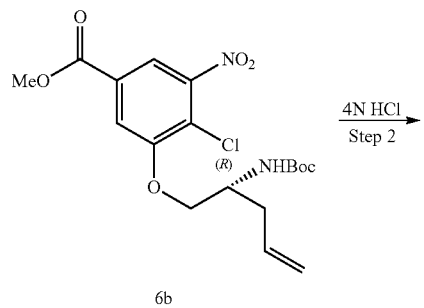

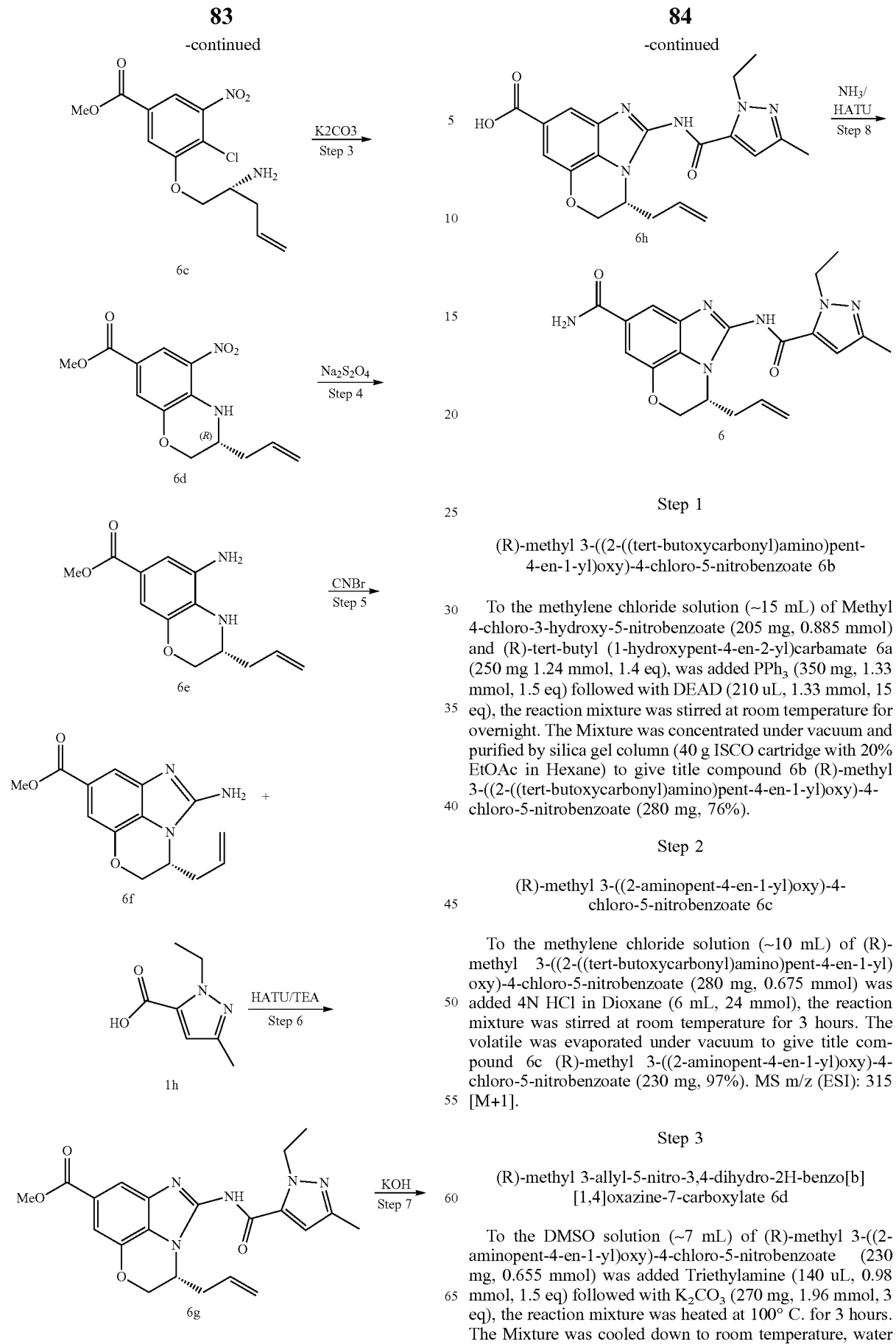

Step 1

(R)-methyl 3-((2-((tert-butoxycarbonyl)amino)pent-4-en-1-yl)oxy)-4-chloro-5-nitrobenzoate 6b To the methylene chloride solution (~15 mL) of Methyl 4-chloro-3-hydroxy-5-nitrobenzoate (205 mg, 0.885 mmol) and (R)-tert-butyl (1-hydroxypent-4-en-2-yl)carbamate 6a (250 mg 1.24 mmol, 1.4 eq), was added PPh$_3$ (350 mg, 1.33 mmol, 1.5 eq) followed with DEAD (210 uL, 1.33 mmol, 15 eq), the reaction mixture was stirred at room temperature for overnight. The Mixture was concentrated under vacuum and purified by silica gel column (40 g ISCO cartridge with 20% EtOAc in Hexane) to give title compound 6b (R)-methyl 3-((2-((tert-butoxycarbonyl)amino)pent-4-en-1-yl)oxy)-4-chloro-5-nitrobenzoate (280 mg, 76%).

Step 2

(R)-methyl 3-((2-aminopent-4-en-1-yl)oxy)-4-chloro-5-nitrobenzoate 6c

To the methylene chloride solution (~10 mL) of (R)-methyl 3-((2-((tert-butoxycarbonyl)amino)pent-4-en-1-yl)oxy)-4-chloro-5-nitrobenzoate (280 mg, 0.675 mmol) was added 4N HCl in Dioxane (6 mL, 24 mmol), the reaction mixture was stirred at room temperature for 3 hours. The volatile was evaporated under vacuum to give title compound 6c (R)-methyl 3-((2-aminopent-4-en-1-yl)oxy)-4-chloro-5-nitrobenzoate (230 mg, 97%). MS m/z (ESI): 315 [M+1].

Step 3

(R)-methyl 3-allyl-5-nitro-3,4-dihydro-2H-benzo[b][1,4]oxazine-7-carboxylate 6d

To the DMSO solution (~7 mL) of (R)-methyl 3-((2-aminopent-4-en-1-yl)oxy)-4-chloro-5-nitrobenzoate (230 mg, 0.655 mmol) was added Triethylamine (140 uL, 0.98 mmol, 1.5 eq) followed with K$_2$CO$_3$ (270 mg, 1.96 mmol, 3 eq), the reaction mixture was heated at 100° C. for 3 hours. The Mixture was cooled down to room temperature, water (~30 mL) was added. The precipitated solid was filtered to give title compound 6d (R)-methyl 3-allyl-5-nitro-3,4-dihydro-2H-benzo[b][1,4]oxazine-7-carboxylate (120 mg, 66%). MS m/z (ESI): 279 [M+1].

Step 4

(R)-methyl 3-allyl-5-amino-3,4-dihydro-2H-benzo[b][1,4]oxazine-7-carboxylate 6e

To the MeOH solution (~15 mL) of (R)-methyl 3-allyl-5-nitro-3,4-dihydro-2H-benzo[b][1,4]oxazine-7-carboxylate (120 mg, 0.431 mmol) was added $Na_2S_2O_4$ (751 mg, 4.31 mmol, 10 eq) in 5 mL water, followed with conc. $NH_4OH$ (0.78 mL, 10.8 mmol), the reaction mixture was stirred at room temperature for 1 hour. The Mixture was diluted with water (20 mL), extracted with EtOAc (30 mL×3). Organic layer was combined, washed with brine (20 mL×1), dried over $Na_2SO_4$, filtered and the filtrated was concentrated under vacuum to give crude title compound 6e (R)-methyl 3-allyl-5-amino-3,4-dihydro-2H-benzo[b][1,4]oxazine-7-carboxylate (118 mg, 100%), which was used in the next step without further purification. MS m/z (ESI): 249 [M+1].

Step 5

(R)-methyl 3-allyl-2-amino-3,4-dihydro-5-oxa-1,2a-diazaacenaphthylene-7-carboxylate 6f To the MeOH solution (~20 mL) of (R)-methyl 3-allyl-5-amino-3,4-dihydro-2H-benzo[b][1,4]oxazine-7-carboxylate (120 mg, 0.475 mmol) was added BrCN (76 mg, 0.713 mmol, 2 eq), the reaction mixture was stirred at room temperature for overnight. The Mixture was concentrated under vacuum to give crude title compound 6f (R)-methyl 3-allyl-2-amino-3,4-dihydro-5-oxa-1,2a-diazaacenaphthylene-7-carboxylate (160 mg, 95%), which was used in the next step without further purification. MS m/z (ESI): 274 [M+1].

Step 6

(R)-methyl 3-allyl-2-(1-ethyl-3-methyl-1H-pyrazole-5-carboxamido)-3,4-dihydro-5-oxa-1,2a-diazaacenaphthylene-7-carboxylate 6g To the DCM (~15 mL) and DMF (~3 mL) solution of (R)-methyl 3-allyl-2-amino-3,4-dihydro-5-oxa-1,2a-diazaacenaphthylene-7-carboxylate (160 mg, 0.463 mmol) was added 1-ethyl-3-methyl-1H-pyrazole-5-carboxylic acid (107 mg, 0.694 mmol, 1.5 eq), HATU (264 mg, 0.694 mmol, 1.5 eq) and TEA (325 uL, 2.32 mmol, 5 eq) the reaction mixture was stirred at room temperature for overnight. LC-Mass showed ~25% SM exist, another 0.5 eq (36 mg, 0.232 mmol) (R)-methyl 3-allyl-2-amino-3,4-dihydro-5-oxa-1,2a-diazaacenaphthylene-7-carboxylate, HATU (88 mg, 0.232 mmol) was added and the mixture was stirred at room temperature for overnight. The Mixture was diluted with DCM (30 mL), washed with water (10 mL×1), dried over $Na_2SO_4$, filtered and the filtrated was concentrated under vacuum. The residue was purified by silica gel column (24 g ISCO cartridge with 10% EtOH and 30% EtOAc in Hexane) to give title compound 6g (R)-methyl 3-allyl-2-(1-ethyl-3-methyl-1H-pyrazole-5-carboxamido)-3,4-dihydro-5-oxa-1,2a-diazaacenaphthylene-7-carboxylate (150 mg, 80%). MS m/z (ESI): 410 [M+1].

Step 7

(R)-3-allyl-2-(1-ethyl-3-methyl-1H-pyrazole-5-carboxamido)-3,4-dihydro-5-oxa-1,2a-diazaacenaphthylene-7-carboxylic acid 6h To the MeOH solution (~1.5 mL) of (R)-methyl 3-allyl-2-(1-ethyl-3-methyl-1H-pyrazole-5-carboxamido)-3,4-dihydro-5-oxa-1,2a-diazaacenaphthylene-7-carboxylate (10 mg, 0.024 mmol) was added 5N KOH aqueous solution (1.5 mL, 7.5 mmol, 30 eq), the reaction mixture was stirred at room temperature for overnight. The Mixture was acidified by 6N HCl to pH<5, diluted with water (10 mL), extracted with EtOAc (10 mL×3). Organic layer was combined, washed with brine (10 mL×1), dried over $Na_2SO_4$, filtered and the filtrated was concentrated under vacuum to give crude title compound 6h (R)-3-allyl-2-(1-ethyl-3-methyl-1H-pyrazole-5-carboxamido)-3,4-dihydro-5-oxa-1,2a-diazaacenaphthylene-7-carboxylic acid (12 mg, 100%), which was used in the next step without further purification. MS m/z (ESI): 396 [M+1].

Step 8

(R)-3-allyl-2-(1-ethyl-3-methyl-1H-pyrazole-5-carboxamido)-3,4-dihydro-5-oxa-1,2a-diazaacenaphthylene-7-carboxamide 6

To the DMF (~1 mL) solution of (R)-3-allyl-2-(1-ethyl-3-methyl-1H-pyrazole-5-carboxamido)-3,4-dihydro-5-oxa-1,2a-diazaacenaphthylene-7-carboxylic acid (12 mg, 0.024 mmol) was added 7N ammonia in MeOH (50 uL, 0.35 mmol, 12 eq), HATU (17.3 mg, 0.046 mmol, 1.5 eq) and TEA (12.6 uL, 0.09 mmol, 3 eq) the reaction mixture was stirred at room temperature for 2 hr. The mixture was purified by reverse phase HPLC, eluated with $AcCN/H_2O$/HCOOH to give title compound 6 (R)-3-allyl-2-(1-ethyl-3-methyl-1H-pyrazole-5-carboxamido)-3,4-dihydro-5-oxa-1,2a-diazaacenaphthylene-7-carboxamide (2.2 mg, 23%). MS m/z (ESI): 395 [M+1].

Example 7

(S)-2-(1-ethyl-3-methyl-1H-pyrazole-5-carboxamido)-3-propyl-3,4-dihydro-5-oxa-1,2a-diazaacenaphthylene-7-carboxamide 7

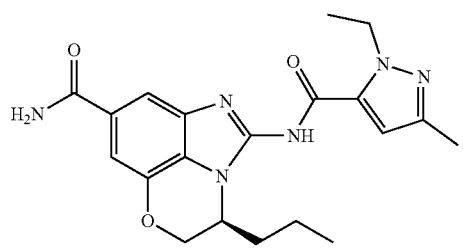

To the MeOH (~10 mL) solution of (S)-3-allyl-2-(1-ethyl-3-methyl-1H-pyrazole-5-carboxamido)-3,4-dihydro-5-oxa-1,2a-diazaacenaphthylene-7-carboxamide (Example 1, 4.8 mg, 0.037 mmol) was added Pd/C (1.5 mg, 20% W/W) and the mixture was hydrogenated under H₂ balloon for 2 hrs. The mixture was filtered through a celite pad. The filtrate was concentrated under vacuum to purified by reverse phase HPLC, eluated with MeOH/H₂O/HCOOH to give title compound (S)-2-(1-ethyl-3-methyl-1H-pyrazole-5-carboxamido)-3-propyl-3,4-dihydro-5-oxa-1,2a-diazaacenaphthylene-7-carboxamide (3.8 mg, 79%). MS m/z (ESI): 397 [M+1].

Example 8

(S)-2-(1-ethyl-3-methyl-1H-pyrazole-5-carboxamido)-3-(pent-2-en-1-yl)-3,4-dihydro-5-oxa-1,2a-diazaacenaphthylene-7-carboxamide 8

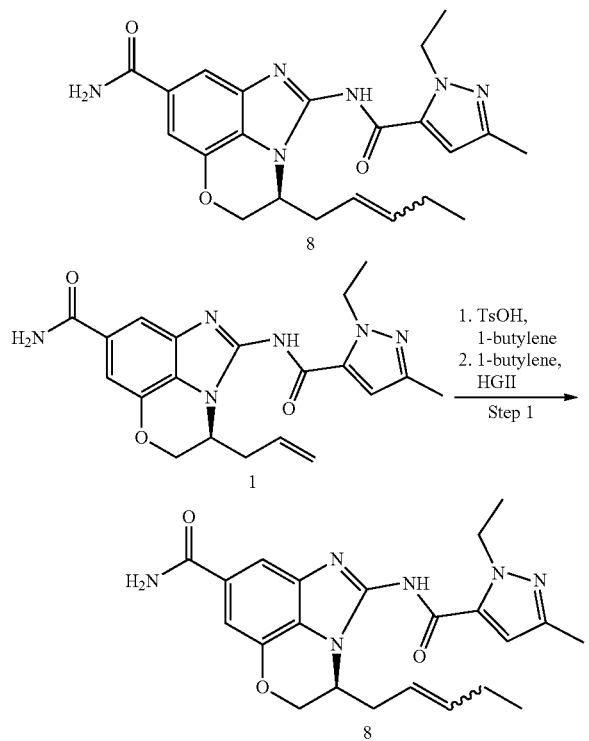

Step 1

(S)-2-(1-ethyl-3-methyl-1H-pyrazole-5-carboxamido)-3-(pent-2-en-1-yl)-3,4-dihydro-5-oxa-1,2a-diazaacenaphthylene-7-carboxamide 8

To a solution of (S)-3-allyl-2-(1-ethyl-3-methyl-1H-pyrazole-5-carboxamido)-3,4-dihydro-5-oxa-1,2a-diazaacenaphthylene-7-carboxamide 1 (10 mg, 0.025 mmol) and p-toluenesulfonic acid monohydrate (15 mg, 0.078 mmol) in MeOH (2 mL) was added 1-Butene (ca. 10% in Hexane) (3 mL). The resulting solution was stirred at room temperature for 15 min before concentrated under vacuum. removed solvents. The residue was dissolved in DCM (3 mL) and transferred to a sealed tube. Hoveyda-Grubbs 2nd Gen Catalyst (10 mg, 0.016 mmol, 0.64 eq) was added, and then the sealed tube was degassed with nitrogenation. After stirring at 40° C. for 2 hours, the mixture was cooled down and then the solvents were removed under vacuum. The mixture was purified by prep-HPLC, eluated with AcCN/H₂O/NH₄HCO₃ to give title compound (S)-2-(1-ethyl-3-methyl-1H-pyrazole-5-carboxamido)-3-(pent-2-en-1-yl)-3,4-dihydro-5-oxa-1,2a-diazaacenaphthylene-7-carboxamide 8 (2.7 mg, 25%). MS m/z (ESI): 423 [M+1]. 1H NMR (400 MHz, MeOD): δ 7.62 (s, 1H), 7.35 (s, 1H), 6.73 (s, 1H), 5.57-5.44 (m, 2H), 4.77-4.66 (m, 4H), 4.34-4.31 (m, 1H), 2.64-2.61 (m, 2H), 2.27 (s, 3H), 2.05-1.87 (m, 2H), 1.47 (d, J=7.1 Hz, 3H), 0.82 (t, J=7.4 Hz, 3H).

Example 9

(3S)-3-(2,3-dihydroxypropyl)-2-(1-ethyl-3-methyl-1H-pyrazole-5-carboxamido)-3,4-dihydro-5-oxa-1,2a-diazaacenaphthylene-7-carboxamide 9

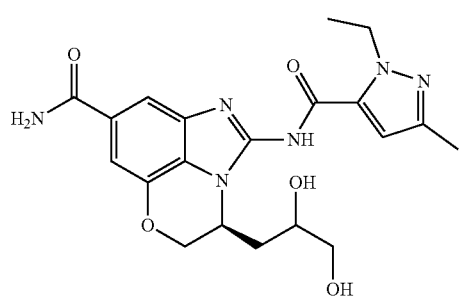

To a stirred solution of (S)-3-allyl-2-(1-ethyl-3-methyl-1H-pyrazole-5-carboxamido)-3,4-dihydro-5-oxa-1,2a-diazaacenaphthylene-7-carboxamide (Example 1, 5 mg, 0.012 mmol) in acetone 1 mL and H₂O (0.5 mL) was added N-methylmorpholine-N-oxide (0.14 mg, 0.9 mmol) and osmium tetroxide (0.05 mL, 4% in water, 0.01 mmol) at room temperature. The mixture was stirred at room temperature overnight. The mixture was quenched with saturated Na₂S₂O₃ (10 ml) and then extracted with EtOAc. The organic layer was dried, and then concentrated. The residue was purified by reverse phase HPLC, eluated with MeOH/H₂O/HCOOH give title compound (3S)-3-(2,3-dihydroxypropyl)-2-(1-ethyl-3-methyl-1H-pyrazole-5-carboxamido)-3,4-dihydro-5-oxa-1,2a-diazaacenaphthylene-7-carboxamide (3.8 mg, 70.1%). MS m/z (ESI): 428 [M+1].

Example 10

(S)-2-(1-ethyl-3-methyl-1H-pyrazole-5-carboxamido)-3-(3-hydroxypropyl)-3,4-dihydro-5-oxa-1,2a-diazaacenaphthylene-7-carboxamide 10

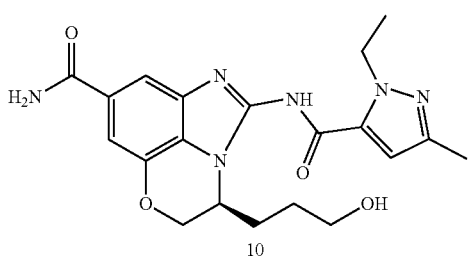

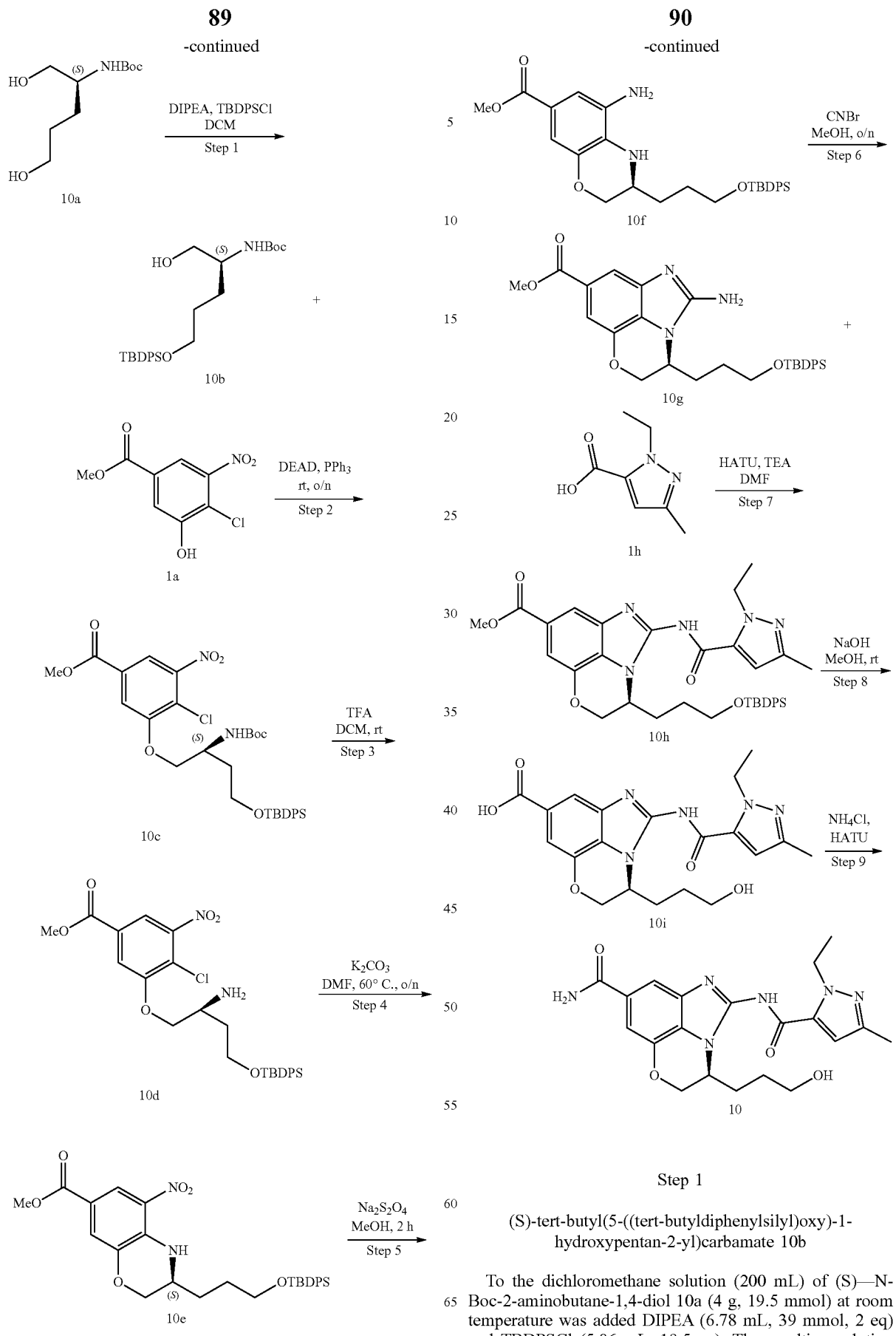
Step 1
(S)-tert-butyl(5-((tert-butyldiphenylsilyl)oxy)-1-hydroxypentan-2-yl)carbamate 10b
To the dichloromethane solution (200 mL) of (S)—N-Boc-2-aminobutane-1,4-diol 10a (4 g, 19.5 mmol) at room temperature was added DIPEA (6.78 mL, 39 mmol, 2 eq) and TBDPSCl (5.06 mL, 19.5 eq). The resulting solution was stirred at 45° C. for 60 hours. The mixture was concentrated under vacuum and purified by silica gel column (330 g ISCO cartridge with 1:4:10 acetone:ether:hexanes) to give title compound (S)-tert-butyl (1-((tert-butyldiphenylsilyl)oxy)-5-hydroxypentan-2-yl)carbamate 10b (higher $R_f$ on TLC, 1.7 g, 20%).

Step 2-Step 9 of Examples 10 was Prepared with the Similar Procedures as Example 5

In step 10, the mixture was purified by prep-HPLC, eluated with AcCN/H$_2$O/TFA to give title compound (S)-2-(1-ethyl-3-methyl-1H-pyrazole-5-carboxamido)-3-(3-hydroxypropyl)-3,4-dihydro-5-oxa-1,2a-diazaacenaphthylene-7-carboxamide 10. MS m/z (ESI): 413 [M+1].

Example 11

(S)-3-allyl-2-(3-methyl-1-propyl-1H-pyrazole-5-carboxamido)-3,4-dihydro-5-oxa-1,2a-diazaacenaphthylene-7-carboxamide 11

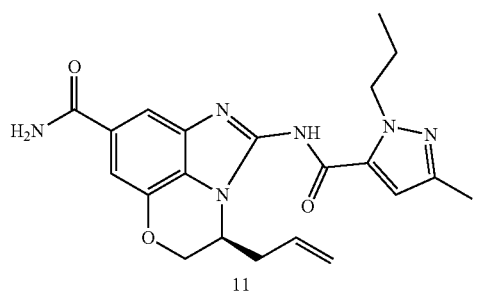

11

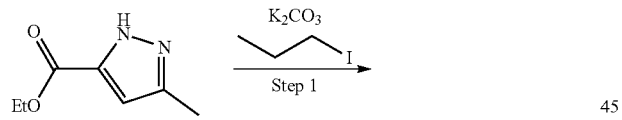

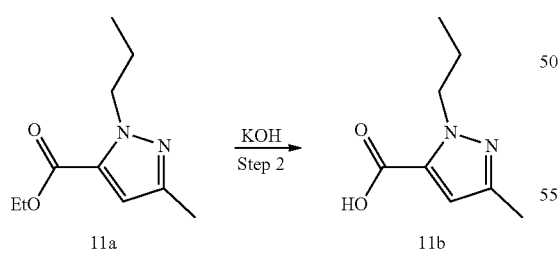

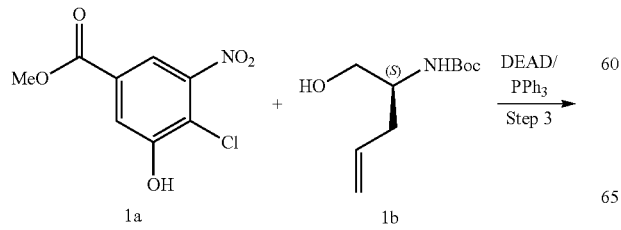

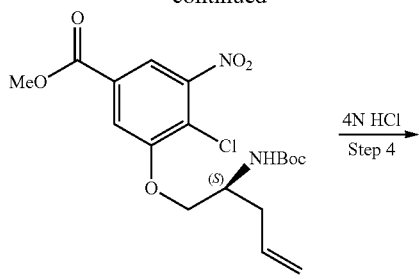

11c

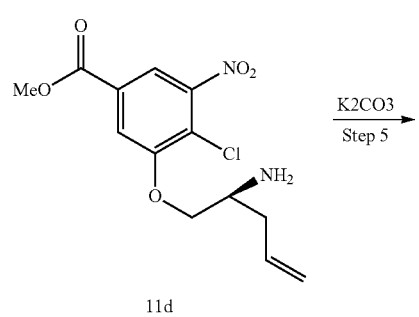

11d

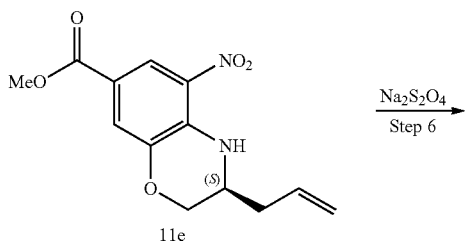

11e

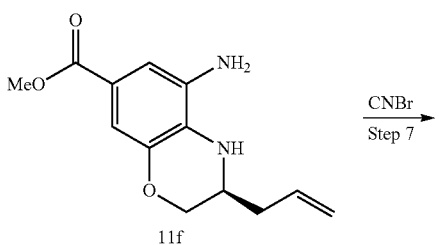

11f

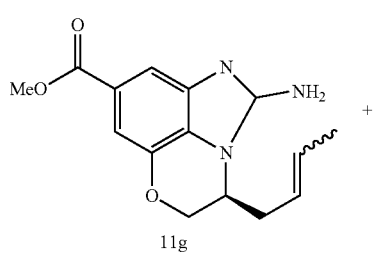

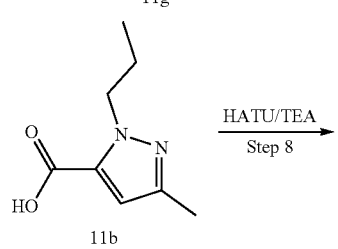

11b

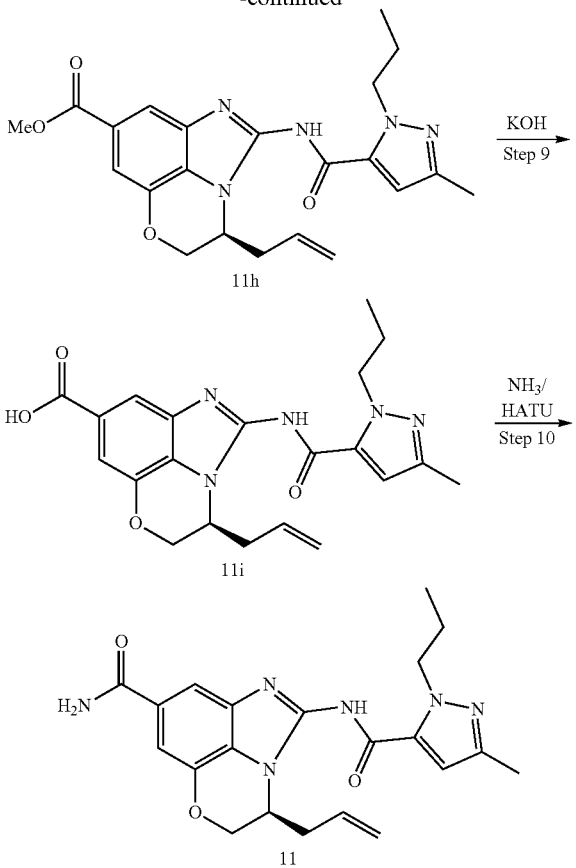

MeOH. Filtered and the filtrated was concentrated under vacuum to give crude title compound 1b 3-methyl-1-propyl-1H-pyrazole-5-carboxylic acid (85 mg, 100%), which was used in the next step without further purification. MS m/z (ESI): 169 [M+1].

Step 3

(S)-methyl 3-((2-((tert-butoxycarbonyl)amino)pent-4-en-1-yl)oxy)-4-chloro-5-nitrobenzoate 11c To the methylene chloride solution (~15 mL) of Methyl 4-chloro-3-hydroxy-5-nitrobenzoate 1a (205 mg, 0.885 mmol) and (S)-tert-butyl (1-hydroxypent-4-yn-2-yl)carbamate 1b (267 mg 1.32 mmol, 1.5 eq), was added $PPh_3$ (350 mg, 1.33 mmol, 1.5 eq) followed with DEAD (210 uL, 1.33 mmol, 1.5 eq), the reaction mixture was stirred at room temperature for overnight. The Mixture was concentrated under vacuum and purified by silica gel column (40 g ISCO cartridge with 20% EtOAc in Hexane) to give title compound 11c (S)-methyl 3-((2-((tert-butoxycarbonyl)amino)pent-4-en-1-yl)oxy)-4-chloro-5-nitrobenzoate (260 mg, 71%).

Step 4

(S)-methyl 3-((2-aminopent-4-en-1-yl)oxy)-4-chloro-5-nitrobenzoate 11d

To the methylene chloride solution (~10 mL) of (S)-methyl 3-((2-((tert-butoxycarbonyl)amino)pent-4-en-1-yl)oxy)-4-chloro-5-nitrobenzoate (260 mg, 0.631 mmol) was added 4N HCl in Dioxane (5 mL, 24 mmol), the reaction mixture was stirred at room temperature for 3 hours. The volatile was evaporated under vacuum to give title compound 11d (S)-methyl 3-((2-aminopent-4-en-1-yl)oxy)-4-chloro-5-nitrobenzoate (210 mg, 96%). MS m/z (ESI): 314 [M+1].

Step 1 ethyl 3-methyl-1-propyl-1H-pyrazole-5-carboxylate 11a

To the DMSO solution (~2 mL) of ethyl 3-methyl-1H-pyrazole-5-carboxylate (100 mg, 0.65 mmol) was added 1-iodopropane (165 mg, 1.0 mmol, 1.5 eq), Triethylamine (150 uL, 1.0 mmol, 1.5 eq) followed with $K_2CO_3$ (280 mg, 2.0 mmol, 3 eq), the reaction mixture was heated at 100° C. for 3 hours. The Mixture was cooled down to room temperature, water (~25 mL) was added. extracted with EtOAc (10 mL×3). Organic layer was combined, washed with brine (10 mL×1), dried over $Na_2SO_4$, filtered and the filtrated was concentrated under vacuum. The residue was purified by silica gel column (12 g ISCO cartridge with 40% EtOAc in Hexane) to give title compound 11a ethyl 3-methyl-1-propyl-1H-pyrazole-5-carboxylate (100 mg, 78%). MS m/z (ESI): 197 [M+1].

Step 5

(S)-methyl 3-allyl-5-nitro-3,4-dihydro-2H-benzo[b][1,4]oxazine-7-carboxylate 11e To the DMSO solution (~7 mL) of (S)-methyl 3-((2-aminopent-4-en-1-yl)oxy)-4-chloro-5-nitrobenzoate (210 mg, 0.617 mmol) was added Triethylamine (150 uL, 1.0 mmol, 1.5 eq) followed with $K_2CO_3$ (280 mg, 2.0 mmol, 3 eq), the reaction mixture was heated at 100° C. for 3 hours. The Mixture was cooled down to room temperature, water (~25 mL) was added. The precipitated solid was filtered to give title compound 11e (S)-methyl 3-allyl-5-nitro-3,4-dihydro-2H-benzo[b][1,4]oxazine-7-carboxylate (100 mg, 66%). MS m/z (ESI): 279 [M+1].

Step 2

3-methyl-1-propyl-1H-pyrazole-5-carboxylic acid 11b

To the MeOH solution (~5 mL) of ethyl 3-methyl-1-propyl-1H-pyrazole-5-carboxylate (100 mg, 0.51 mmol) was added 5N KOH aqueous solution (3 mL, 15 mmol, 30 eq), the reaction mixture was stirred at room temperature for overnight. The Mixture was acidified by 6N HCl to pH<5 and concentrated then dried over $Na_2SO_4$, redissolved in Step 6

(S)-methyl 3-allyl-5-amino-3,4-dihydro-2H-benzo[b][1,4]oxazine-7-carboxylate 11f To the MeOH solution (~15 mL) of (S)-methyl 3-allyl-5-nitro-3,4-dihydro-2H-benzo[b][1,4]oxazine-7-carboxylate (100 mg, 0.361 mmol) was added $Na_2S_2O_4$ (630 mg, 3.62 mmol, 10 eq) in 5 mL water, followed with conc. $NH_4OH$ (0.78 mL, 10.8 mmol), the reaction mixture was stirred at room temperature for 1 hour. The Mixture was diluted with water (20 mL), extracted with EtOAc (30 mL×3). Organic layer was combined, washed with brine (20 mL), dried over Na₂SO₄, filtered and the filtrated was concentrated under vacuum to give crude title compound 11f (S)-methyl 3-allyl-5-amino-3,4-dihydro-2H-benzo[b][1,4]oxazine-7-carboxylate (92 mg, 100%), which was used in the next step without further purification. MS m/z (ESI): 249 [M+1].

Step 7

(S)-methyl 3-allyl-2-amino-3,4-dihydro-5-oxa-1,2a-diazaacenaphthylene-7-carboxylate 11g To the MeOH solution (~20 mL) of (S)-methyl 3-allyl-5-amino-3,4-dihydro-2H-benzo[b][1,4]oxazine-7-carboxylate (92 mg, 0.365 mmol) was added BrCN (68 mg, 0.73 mmol, 2 eq), the reaction mixture was stirred at room temperature for overnight. The Mixture was concentrated under vacuum to give crude title compound 11g (S)-methyl 3-allyl-2-amino-3,4-dihydro-5-oxa-1,2a-diazaacenaphthylene-7-carboxylate (100 mg, 99%), which was used in the next step without further purification. MS m/z (ESI): 274 [M+1].

Step 8

(S)-methyl 3-allyl-2-(3-methyl-1-propyl-1H-pyrazole-5-carboxamido)-3,4-dihydro-5-oxa-1,2a-diazaacenaphthylene-7-carboxylate 11h To the DCM (~15 mL) and DMF (~3 mL) solution of (S)-methyl 3-allyl-2-amino-3,4-dihydro-5-oxa-1,2a-diazaacenaphthylene-7-carboxylate (100 mg, 0.365 mmol) was added 3-methyl-1-propyl-1H-pyrazole-5-carboxylic acid (85 mg, 0.51 mmol, 1.4 eq), HATU (205 mg, 0.54 mmol, 1.5 eq) and TEA (255 uL, 1.825 mmol, 5 eq) the reaction mixture was stirred at room temperature for overnight. The Mixture was diluted with DCM (30 mL), washed with water (10 mL), dried over Na₂SO₄, filtered and the filtrated was concentrated under vacuum. The residue was purified by silica gel column (24 g ISCO cartridge with 10% EtOH and 30% EtOAc in Hexane) to give title compound 11h (S)-methyl 3-allyl-2-(3-methyl-1-propyl-1H-pyrazole-5-carboxamido)-3,4-dihydro-5-oxa-1,2a-diazaacenaphthylene-7-carboxylate (110 mg, 73%). MS m/z (ESI): 424 [M+1].

Step 9

(S)-3-allyl-2-(3-methyl-1-propyl-1H-pyrazole-5-carboxamido)-3,4-dihydro-5-oxa-1,2a-diazaacenaphthylene-7-carboxylic acid 11i To the MeOH solution (~1.5 mL) of (S)-methyl 3-allyl-2-(3-methyl-1-propyl-1H-pyrazole-5-carboxamido)-3,4-dihydro-5-oxa-1,2a-diazaacenaphthylene-7-carboxylate (10 mg, 0.024 mmol) was added 5N KOH aqueous solution (1.5 mL, 7.5 mmol, 30 eq), the reaction mixture was stirred at room temperature for overnight. The Mixture was acidified by 6N HCl to pH<5, diluted with water (10 mL), extracted with EtOAc (10 mL×3). Organic layer was combined, washed with brine (10 mL), dried over Na₂SO₄, filtered and the filtrated was concentrated under vacuum to give crude title compound 11i (S)-3-allyl-2-(3-methyl-1-propyl-1H-pyrazole-5-carboxamido)-3,4-dihydro-5-oxa-1,2a-diazaacenaphthylene-7-carboxylic acid (12 mg, 100%), which was used in the next step without further purification. MS m/z (ESI): 410 [M+1].

Step 10

(S)-3-allyl-2-(3-methyl-1-propyl-1H-pyrazole-5-carboxamido)-3,4-dihydro-5-oxa-1,2a-diazaacenaphthylene-7-carboxamide 11

To the DMF (~1 mL) solution of (S)-3-allyl-2-(3-methyl-1-propyl-1H-pyrazole-5-carboxamido)-3,4-dihydro-5-oxa-1,2a-diazaacenaphthylene-7-carboxylic acid (12 mg, 0.024 mmol) was added NH₄Cl (50 uL, 0.35 mmol, 12 eq), HATU (17.3 mg, 0.046 mmol, 1.5 eq) and TEA (12.6 uL, 0.09 mmol, 3 eq) the reaction mixture was stirred at room temperature for 2 hr. The mixture was purified by reverse phase HPLC, eluated with AcCN/H₂O/HCOOH to give title compound 11 (S)-3-allyl-2-(3-methyl-1-propyl-1H-pyrazole-5-carboxamido)-3,4-dihydro-5-oxa-1,2a-diazaacenaphthylene-7-carboxamide (2.2 mg, 23%). MS m/z (ESI): 409 [M+1].

Example 12

(S)-3-allyl-2-(1-(cyclopropylmethyl)-3-methyl-1H-pyrazole-5-carboxamido)-3,4-dihydro-5-oxa-1,2a-diazaacenaphthylene-7-carboxamide 12

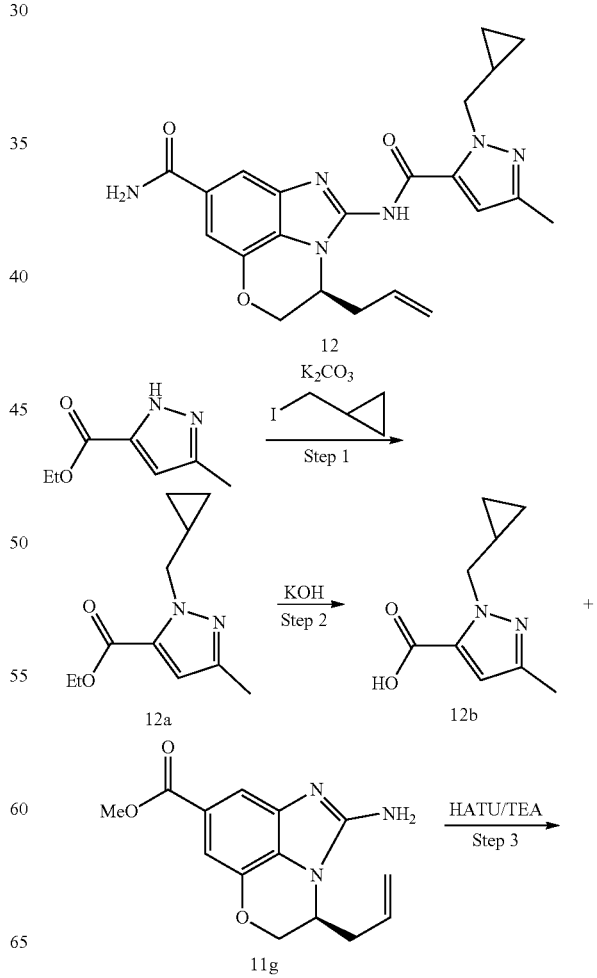

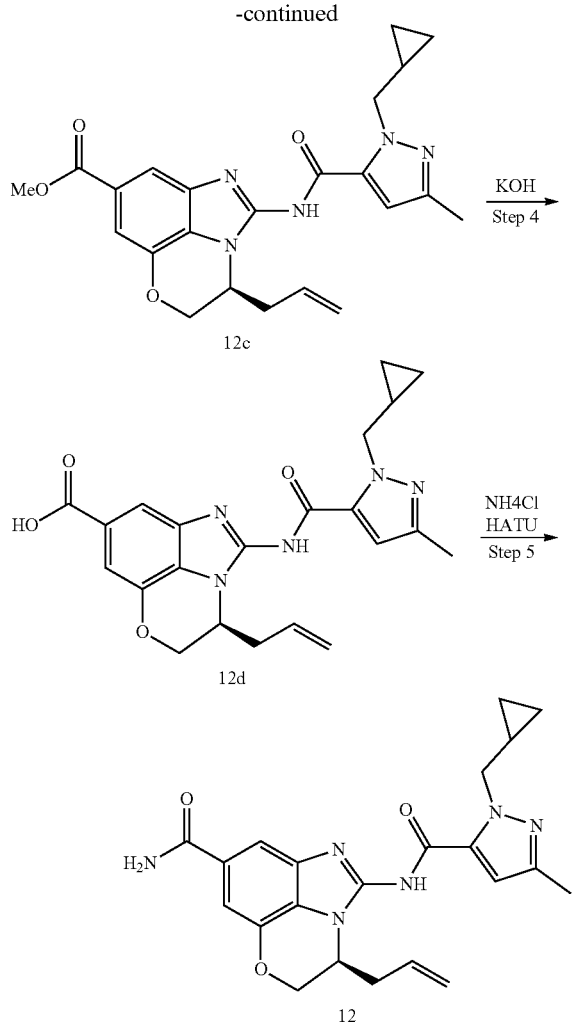

Step 1 ethyl 1-(cyclopropylmethyl)-3-methyl-1H-pyrazole-5-carboxylate 12a

To the DMSO solution (~2 mL) of ethyl 3-methyl-1H-pyrazole-5-carboxylate (200 mg, 1.3 mmol) was added (iodomethyl)cyclopropane (365 mg, 2 mmol, 1.5 eq), Triethylamine (300 uL, 2.0 mmol, 1.5 eq) followed with $K_2CO_3$ (560 mg, 4.0 mmol, 3 eq), the reaction mixture was heated at 100° C. for 3 hours. The Mixture was cooled down to room temperature, water (~25 mL) was added. extracted with EtOAc (10 mL×3). Organic layer was combined, washed with brine (10 mL×1), dried over $Na_2SO_4$, filtered and the filtrated was concentrated under vacuum. The residue was purified by silica gel column (12 g ISCO cartridge with 40% EtOAc in Hexane) to give title compound 12a ethyl 1-(cyclopropylmethyl)-3-methyl-1H-pyrazole-5-carboxylate (189 mg, 70%). MS m/z (ESI): 209 [M+1].

Step 2

1-(cyclopropylmethyl)-3-methyl-1H-pyrazole-5-carboxylic acid 12b

To the MeOH solution (~5 mL) of ethyl 1-(cyclopropylmethyl)-3-methyl-1H-pyrazole-5-carboxylate (189 mg, 0.91 mmol) was added 5N KOH aqueous solution (3 mL, 15 mmol, 17 eq), the reaction mixture was stirred at room temperature for overnight. The Mixture was acidified by 6N HCl to pH<5 and concentrated then dried over $Na_2SO_4$, and redissolved in MeOH. Filtered and the filtrated was concentrated under vacuum to give crude title compound 12b 1-(cyclopropylmethyl)-3-methyl-1H-pyrazole-5-carboxylic acid (163 mg, 100%), which was used in the next step without further purification. MS m/z (ESI): 181 [M+1].

Step 3

(S)-methyl 3-allyl-2-(1-(cyclopropylmethyl)-3-methyl-1H-pyrazole-5-carboxamido)-3,4-dihydro-5-oxa-1,2a-diazaacenaphthylene-7-carboxylate 12c To the DCM (~15 mL) and DMF (~3 mL) solution of (S)-methyl 3-allyl-2-amino-3,4-dihydro-5-oxa-1,2a-diazaacenaphthylene-7-carboxylate 11g (100 mg, 0.365 mmol) was added 1-(cyclopropylmethyl)-3-methyl-1H-pyrazole-5-carboxylic acid (85 mg, 0.51 mmol, 1.4 eq), HATU (205 mg, 0.54 mmol, 1.5 eq) and TEA (255 uL, 1.825 mmol, 5 eq) the reaction mixture was stirred at room temperature for overnight. The Mixture was diluted with DCM (30 mL), washed with water (10 mL), dried over $Na_2SO_4$, filtered and the filtrated was concentrated under vacuum. The residue was purified by silica gel column (24 g ISCO cartridge with 10% EtOH and 30% EtOAc in Hexane) to give title compound 12c (S)-methyl 3-allyl-2-(1-(cyclopropylmethyl)-3-methyl-1H-pyrazole-5-carboxamido)-3,4-dihydro-5-oxa-1,2a-diazaacenaphthylene-7-carboxylate (120 mg, 72%). MS m/z (ESI): 436 [M+1].

Step 4

(S)-3-allyl-2-(1-(cyclopropylmethyl)-3-methyl-1H-pyrazole-5-carboxamido)-3,4-dihydro-5-oxa-1,2a-diazaacenaphthylene-7-carboxylic acid 12d To the MeOH solution (~1.5 mL) of (S)-methyl 3-allyl-2-(1-(cyclopropylmethyl)-3-methyl-1H-pyrazole-5-carboxamido)-3,4-dihydro-5-oxa-1,2a-diazaacenaphthylene-7-carboxylate (20 mg, 0.024 mmol) was added 5N KOH aqueous solution (1.5 mL, 7.5 mmol, 30 eq), the reaction mixture was stirred at room temperature for overnight. The Mixture was acidified by 6N HCl to pH<5, diluted with water (10 mL), extracted with EtOAc (10 mL×3). Organic layer was combined, washed with brine (10 mL), dried over $Na_2SO_4$, filtered and the filtrated was concentrated under vacuum to give crude title compound 12d (S)-3-allyl-2-(1-(cyclopropylmethyl)-3-methyl-1H-pyrazole-5-carboxamido)-3,4-dihydro-5-oxa-1,2a-diazaacenaphthylene-7-carboxylic acid (18 mg, 90%), which was used in the next step without further purification. MS m/z (ESI): 422 [M+1].

Step 5

(S)-3-allyl-2-(1-(cyclopropylmethyl)-3-methyl-1H-pyrazole-5-carboxamido)-3,4-dihydro-5-oxa-1,2a-diazaacenaphthylene-7-carboxamide 12

To the DMF (~1 mL) solution of (S)-3-allyl-2-(1-(cyclopropylmethyl)-3-methyl-1H-pyrazole-5-carboxamido)-3,4-dihydro-5-oxa-1,2a-diazaacenaphthylene-7-carboxylic acid (18 mg, 0.042 mmol) was added $NH_4Cl$ (34 mg, 0.63 mmol, 15 eq), HATU (25.5 mg, 0.063 mmol, 1.5 eq) and TEA (31.5 uL, 0.14 mmol, 3 eq) the reaction mixture was stirred at room temperature for 2 hr. The mixture was purified by reverse phase HPLC, eluated with AcCN/H₂O/HCOOH to give title compound 12 (S)-3-allyl-2-(1-(cyclopropylmethyl)-3-methyl-1H-pyrazole-5-carboxamido)-3,4-dihydro-5-oxa-1,2a-diazaacenaphthylene-7-carboxamide (4.6 mg, 25%). MS m/z (ESI): 421 [M+1].

Example 13

(S)-3-(3-(5-carbamoyl-2-(1-ethyl-3-methyl-1H-pyrazole-5-carboxamido)-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 13

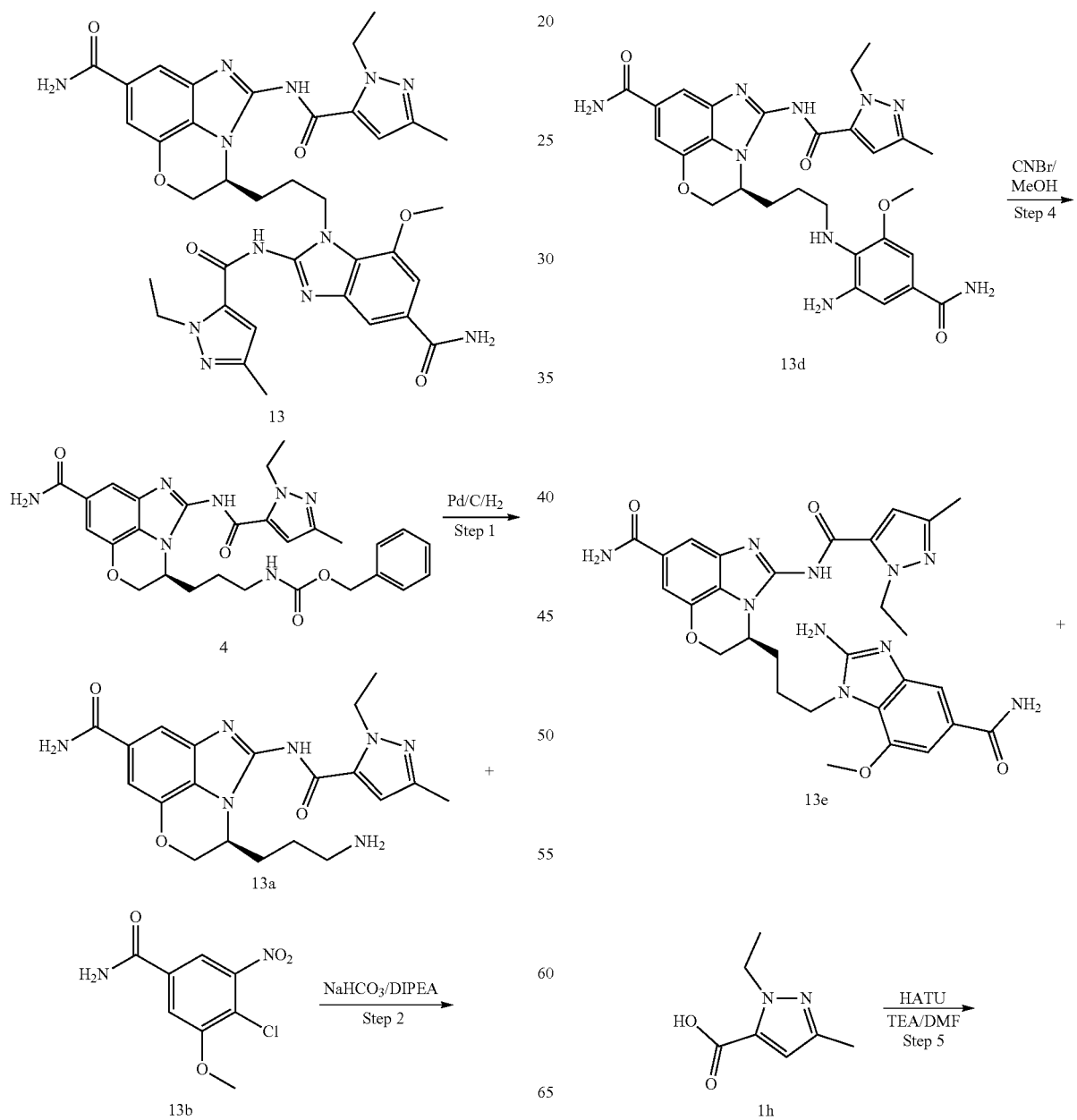

-continued

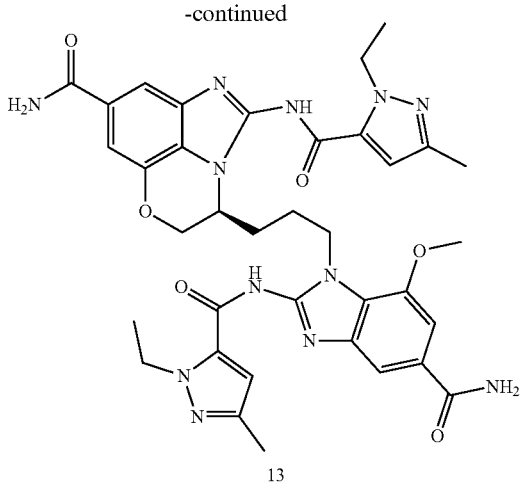

13

Step 1

(S)-3-(3-aminopropyl)-2-(1-ethyl-3-methyl-1H-pyrazole-5-carboxamido)-3,4-dihydro-5-oxa-1,2a-diazaacenaphthylene-7-carboxamide 13a To the MeOH (~10 mL) solution of (S)-benzyl (3-(7-carbamoyl-2-(1-ethyl-3-methyl-1H-pyrazole-5-carboxamido)-3,4-dihydro-5-oxa-1,2a-diazaacenaphthylen-3-yl)propyl)carbamate (Example 4.20 mg, 0.037 mmol) was added Pd/C (4 mg, 20% W/W) and the mixture was hydrogenated under $H_2$ balloon for 2 hrs. The mixture was filtered through a celite pad. The filtrate was concentrated under vacuum to give crude title compound 13a (S)-3-(3-aminopropyl)-2-(1-ethyl-3-methyl-1H-pyrazole-5-carboxamido)-3,4-dihydro-5-oxa-1,2a-diazaacenaphthylene-7-carboxamide (12 mg, 80%), which was used in the next step without further purification. MS m/z (ESI): 412 [M+1].

Step 2

(S)-3-(3-((4-carbamoyl-2-methoxy-6-nitrophenyl)amino)propyl)-2-(1-ethyl-3-methyl-1H-pyrazole-5-carboxamido)-3,4-dihydro-5-oxa-1,2a-diazaacenaphthylene-7-carboxamide 13c To the n-Butanol (~2 mL) solution of (S)-3-(3-aminopropyl)-2-(1-ethyl-3-methyl-1H-pyrazole-5-carboxamido)-3,4-dihydro-5-oxa-1,2a-diazaacenaphthylene-7-carboxamide (10 mg, 0.024 mmol) and 4-chloro-3-methoxy-5-nitrobenzamide (0.036 mmol, 1.5 eq) was added DIPEA (9.3 mg 0.072 mmol, 3 eq) the mixture was stirred at room temperature for 10 mins. Then was added $NaHCO_3$ (6 mg, 0.072 mmol, 3 eq) and heated to 120° C. for 12 hours. The mixture was filtered through a celite pad and washed with menthol. The filtrate was concentrated under vacuum. The residue was purified by silica gel column (12 g ISCO cartridge with 60% EtOAc, 30% EtOH in Hexane) to give title compound 13c (S)-3-(3-((4-carbamoyl-2-methoxy-6-nitrophenyl)amino)propyl)-2-(1-ethyl-3-methyl-1H-pyrazole-5-carboxamido)-3,4-dihydro-5-oxa-1,2a-diazaacenaphthylene-7-carboxamide (8.1 mg, 55%). MS m/z (ESI): 606 [M+1].

Step 3

(S)-3-(3-((2-amino-4-carbamoyl-6-methoxyphenyl)amino)propyl)-2-(1-ethyl-3-methyl-1H-pyrazole-5-carboxamido)-3,4-dihydro-5-oxa-1,2a-diazaacenaphthylene-7-carboxamide 13d To the MeOH (~10 mL) solution of (S)-3-(3-((4-carbamoyl-2-methoxy-6-nitrophenyl)amino)propyl)-2-(1-ethyl-3-methyl-1H-pyrazole-5-carboxamido)-3,4-dihydro-5-oxa-1,2a-diazaacenaphthylene-7-carboxamide (8.1 mg, 0.013 mmol) was added Pd/C (2 mg, 25% W/W) and the mixture was hydrogenated under $H_2$ balloon for 4 hrs. The mixture was filtered through a celite pad. The filtrate was concentrated under vacuum to give crude title compound 13d (S)-3-(3-((2-amino-4-carbamoyl-6-methoxyphenyl)amino)propyl)-2-(1-ethyl-3-methyl-1H-pyrazole-5-carboxamido)-3,4-dihydro-5-oxa-1,2a-diazaacenaphthylene-7-carboxamide (5.7 mg, 70%), which was used in the next step without further purification. MS m/z (ESI): 576 [M+1].

Step 4

(S)-3-(3-(2-amino-5-carbamoyl-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 13e To the MeOH solution (~5 mL) of (S)-3-(3-((2-amino-4-carbamoyl-6-methoxyphenyl)amino)propyl)-2-(1-ethyl-3-methyl-1H-pyrazole-5-carboxamido)-3,4-dihydro-5-oxa-1,2a-diazaacenaphthylene-7-carboxamide (5.7 mg, 0.01 mmol) was added BrCN (20 mg, 0.06 mmol, 6 eq), the reaction mixture was stirred at room temperature for overnight. The Mixture was concentrated under vacuum to give crude title compound 13e (S)-3-(3-(2-amino-5-carbamoyl-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide (5.9 mg, 100%), which was used in the next step without further purification. MS m/z (ESI): 601 [M+1].

Step 5

(S)-3-(3-(5-carbamoyl-2-(1-ethyl-3-methyl-1H-pyrazole-5-carboxamido)-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 13

To the DCM (~3 mL) and DMF (~1 mL) solution of (S)-3-(3-(2-amino-5-carbamoyl-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide (5.9 mg, 0.01 mmol) was added 1-ethyl-3-methyl-1H-pyrazole-5-carboxylic acid (2.5 mg, 0.015 mmol, 1.5 eq), HATU (5.7 mg, 0.015 mmol, 1.5 eq) and TEA (7.6 mg, 0.075 mmol, 5 eq) the reaction mixture was stirred at room temperature for 2 hr. LC-Mass showed major diamide. The mixture was concentrated under vacuum. The mixture was purified by reverse phase HPLC, eluated with $MeOH/H_2O$ to give title compound 13 (S)-3-(3-(5-carbamoyl-2-(1-ethyl-3-methyl-1H-pyrazole-5-carboxamido)-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide (2.1 mg, 28%). MS m/z (ESI): 737 [M+1]; 1H NMR (400 MHz, Methanol-$d_4$)

δ 7.54-7.49 (m, 2H), 7.38-7.28 (m, 2H), 6.61 (s, 1H), 6.53 (s, 1H), 4.79 (s, 1H), 4.67-4.54 (m, 6H), 4.45 (s, 3H), 4.26 (d, J=11.8 Hz, 1H), 3.86 (s, 3H), 2.19 (d, J=10.0 Hz, 8H), 2.10 (s, 4H), 1.37 (t, J=7.1 Hz, 6H).
Example 14
(S)-3-(3-(5-carbamoyl-2-(1-ethyl-3-methyl-1H-pyrazole-5-carboxamido)-7-methoxy-1H-benzo[d]imidazol-1-yl)prop-1-en-1-yl)-2-(1-ethyl-3-methyl-1H-pyrazole-5-carboxamido)-3,4-dihydro-5-oxa-1,2a-diazaacenaphthylene-7-carboxamide 14
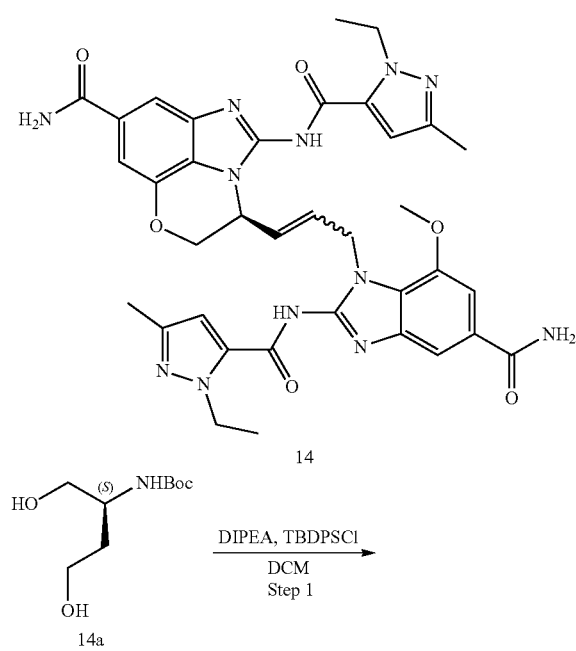
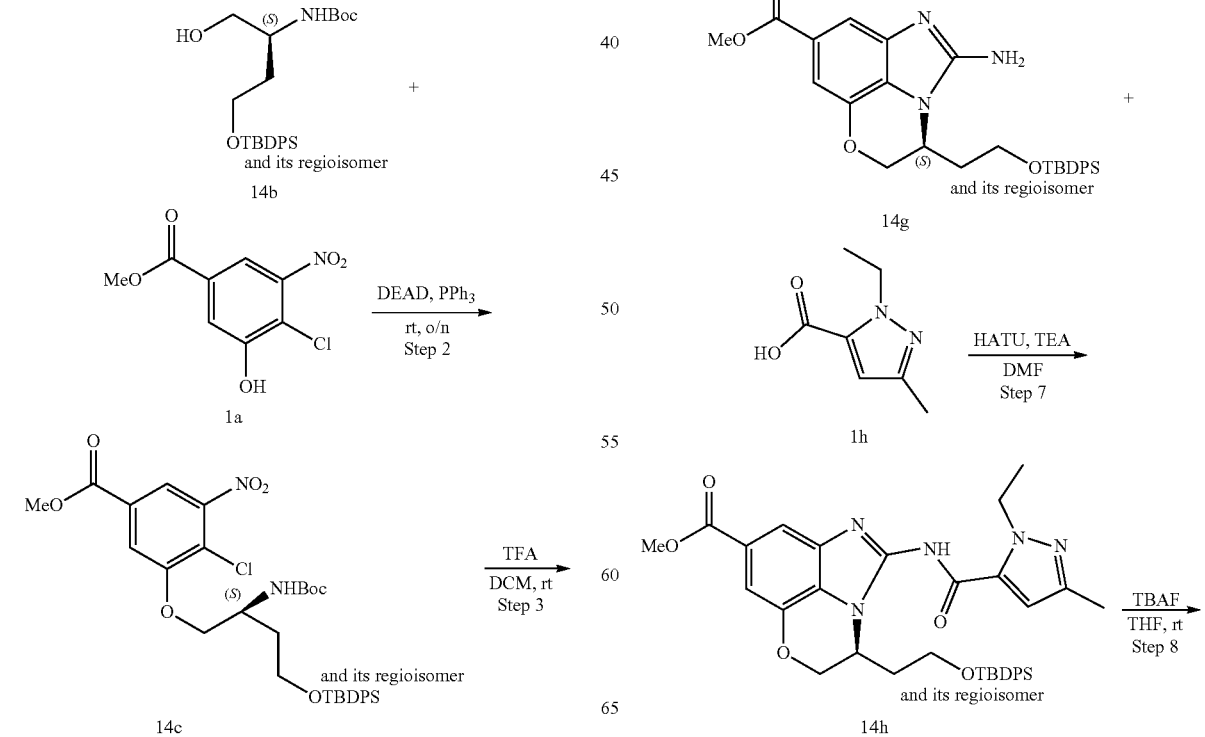
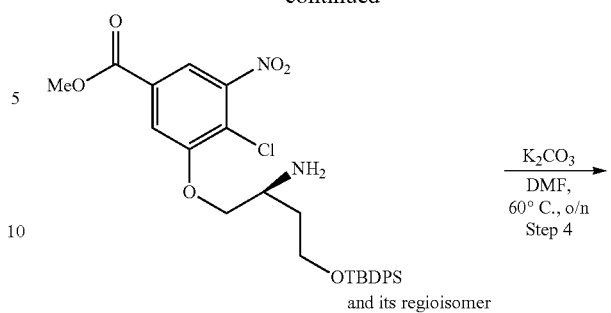
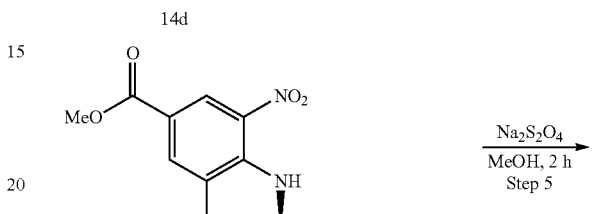
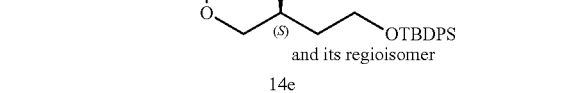
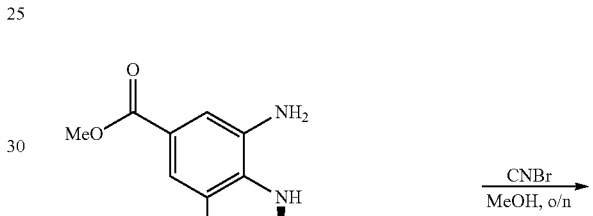
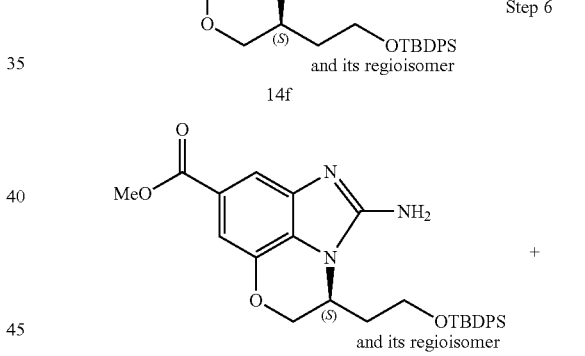
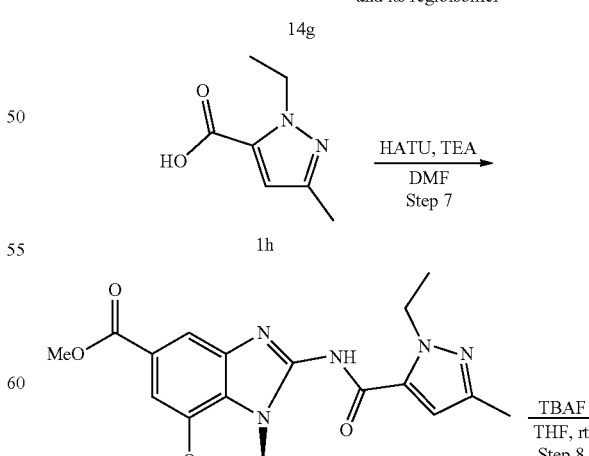

-continued

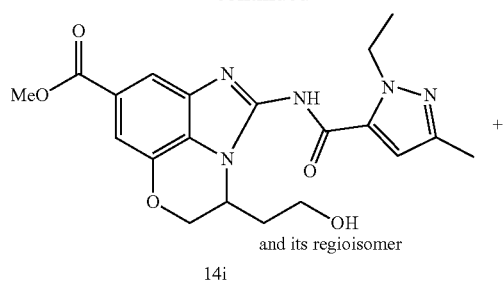

14i and its regioisomer

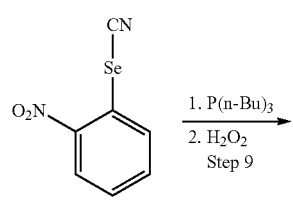

1. P(n-Bu)₃
2. H₂O₂
Step 9

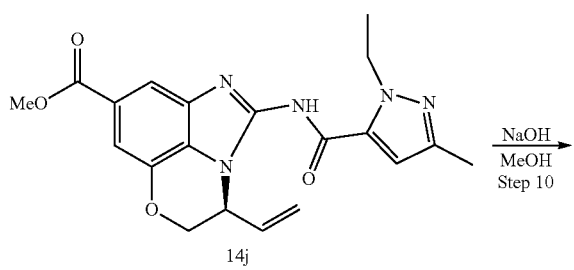

14j

NaOH
MeOH
Step 10

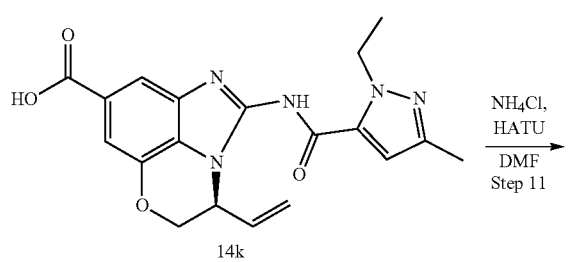

14k

NH₄Cl, HATU
DMF
Step 11

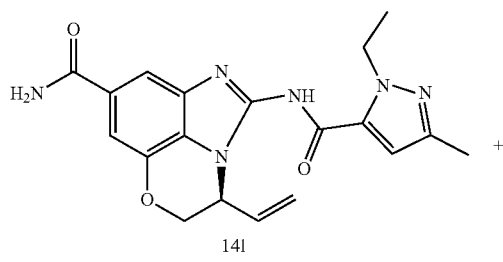

14l

+

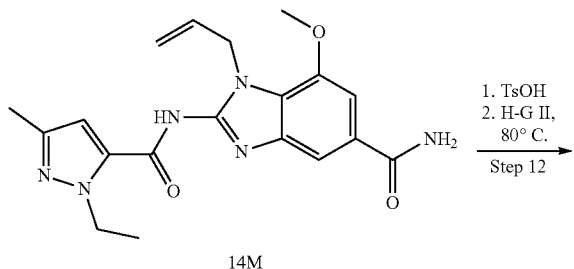

14M

1. TsOH
2. H-G II, 80° C.
Step 12

-continued

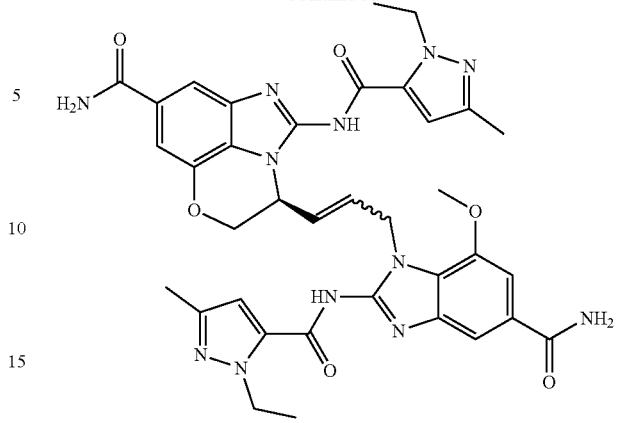

14

Step 1

(S)-tert-butyl(4-((tert-butyldiphenylsilyl)oxy)-1-hydroxybutan-2-yl)carbamate 14b To the dichloromethane solution (200 mL) of (S)-tert-butyl (1,4-dihydroxybutan-2-yl)carbamate 14a (4 g, 19.5 mmol) at room temperature was added DIPEA (6.78 mL, 39 mmol, 2 eq) and TBDPSCl (5.06 mL, 19.5 eq). The resulting solution was stirred at 45° C. for 48 hours. The mixture was concentrated under vacuum and purified by silica gel column (120 g ISCO cartridge with 0-100% EtOAc in Hexane) to give title compound (S)-tert-butyl (4-((tert-butyldiphenylsilyl)oxy)-1-hydroxybutan-2-yl)carbamate 14b and its regioisomer as ~1:1 mixture (7.7 g, 89%).

Step 2-Step 7 of Examples 14 was Prepared with the Similar Procedures as Example 5

Step 8

Methyl 2-(1-ethyl-3-methyl-1H-pyrazole-5-carboxamido)-3-(2-hydroxyethyl)-3,4-dihydro-5-oxa-1,2a-diazaacenaphthylene-7-carboxylate 14i To the tetrahydrofuran solution (30 mL) of mixture of (S)-methyl 3-(2-((tert-butyldiphenylsilyl)oxy)ethyl)-2-(1-ethyl-3-methyl-1H-pyrazole-5-carboxamido)-3,4-dihydro-5-oxa-1,2a-diazaacenaphthylene-7-carboxylate 14h and its regioisomer (1.32 g, 20 mmol) was added TBAF (2.12 mL, 21 mmol, 1.05 eq). The reaction mixture was stirred at room temperature for 2 hours. The mixture was concentrated under vacuum and purified by silica gel column (80 g ISCO cartridge with 0-100% EtOAc in Hexane) to give title compound Methyl 2-(1-ethyl-3-methyl-1H-pyrazole-5-carboxamido)-3-(2-hydroxyethyl)-3,4-dihydro-5-oxa-1,2a-diazaacenaphthylene-7-carboxylate 14i and its regioisomer (800 mg, 93%).

Step 9

(S)-methyl 2-(1-ethyl-3-methyl-1H-pyrazole-5-carboxamido)-3-vinyl-3,4-dihydro-5-oxa-1,2a-diazaacenaphthylene-7-carboxylate 14j

To the tetrahydrofuran solution (10 mL) of mixture of Methyl 2-(1-ethyl-3-methyl-1H-pyrazole-5-carboxamido)-3-(2-hydroxyethyl)-3,4-dihydro-5-oxa-1,2a-diazaacenaphthylene-7-carboxylate 14i and its regioisomer (152 mg, 0.38 mmol) at 0° C. under $N_2$ was added 2-nitrophenyl selenocyanate (250 mg, 1.10 mmol) in THF (5 mL) dropwise, followed by addition of tri-n-butylphosphine (0.276 mL, 1.10 mmol). The resulting solution was stirred at rt for 1.5 hours, cooled to 0° C., and then added $H_2O_2$ (0.2 mL, 1.47 mmol). The resulting solution was slowly warm up to room temperature and stirred for 2 hours. The mixture was concentrated under vacuum and purified by silica gel column (40 g ISCO cartridge with 0-100% EtOAc in Hexane) to give title compound (S)-methyl 2-(1-ethyl-3-methyl-1H-pyrazole-5-carboxamido)-3-vinyl-3,4-dihydro-5-oxa-1,2a-diazaacenaphthylene-7-carboxylate 14j (52 mg, 35%).

Step 10 and Step 11 of Examples 14 was Prepared with the Similar Procedures as Example 5

Step 12

(S)-3-(3-(5-carbamoyl-2-(1-ethyl-3-methyl-1H-pyrazole-5-carboxamido)-7-methoxy-1H-benzo[d]imidazol-1-yl)prop-1-en-1-yl)-2-(1-ethyl-3-methyl-1H-pyrazole-5-carboxamido)-3,4-dihydro-5-oxa-1,2a-diazaacenaphthylene-7-carboxamide 14

To the dichloromethane solution (1 mL) of (S)-2-(1-ethyl-3-methyl-1H-pyrazole-5-carboxamido)-3-vinyl-3,4-dihydro-5-oxa-1,2a-diazaacenaphthylene-7-carboxamide 14l (12 mg) and 1-allyl-2-(1-ethyl-3-methyl-1H-pyrazole-5-carboxamido)-7-methoxy-1H-benzo[d]imidazole-5-carboxamide 14m (WO2017175156, 10 mg) at room temperature was added TsOH.$H_2O$ (20 mg) in MeOH (0.5 mL). The resulting solution was stirred at room temperature for 15 min and then concentrated under vacuum. To redissolved residue in DCM (2 mL) under $N_2$ was added H-G II (15 mg). The resulting solution was stirred 6 hours at 80° C., The mixture was concentrated, and then purified by prep-HPLC, eluated with ACN/$H_2O$/$NH_4HCO_3$ to give title compound (S)-3-(3-(5-carbamoyl-2-(1-ethyl-3-methyl-1H-pyrazole-5-carboxamido)-7-methoxy-1H-benzo[d]imidazol-1-yl)prop-1-en-1-yl)-2-(1-ethyl-3-methyl-1H-pyrazole-5-carboxamido)-3,4-dihydro-5-oxa-1,2a-diazaacenaphthylene-7-carboxamide 14 (3.8 mg, 19%). MS m/z (ESI): 735 [M+1].

Example 15

(S,E)-3-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-3,4-dihydro-5-oxa-1,2a-diazaacenaphthylene-7-carboxamide

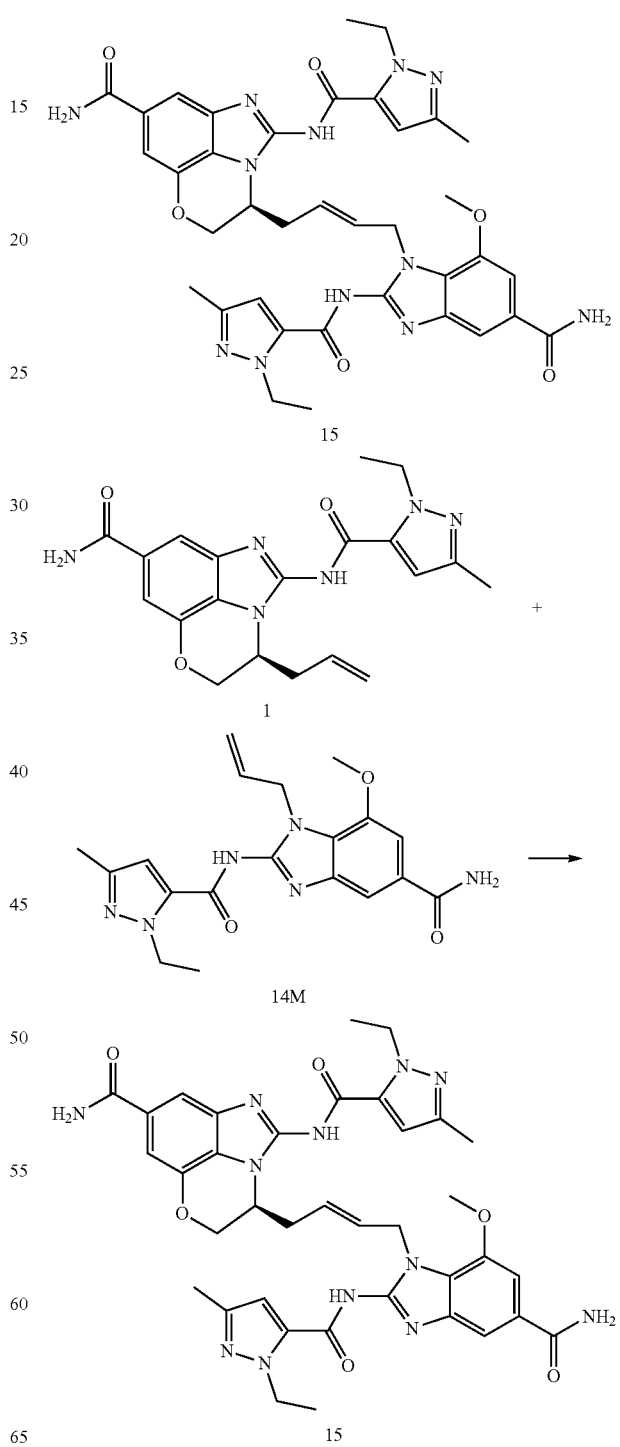

The title compound was prepared from Example 1 and compound 14M with the same method as step 12 of Example 14. MS m/z (ESI): 749 [M+1].

Example 16

(S)-3-(4-(5-carbamoyl-2-(1-ethyl-3-methyl-1H-pyrazole-5-carboxamido)-7-methoxy-1H-benzo[d]imidazol-1-yl)butyl)-2-(1-ethyl-3-methyl-1H-pyrazole-5-carboxamido)-3,4-dihydro-5-oxa-1,2a-diazaacenaphthylene-7-carboxamide 16

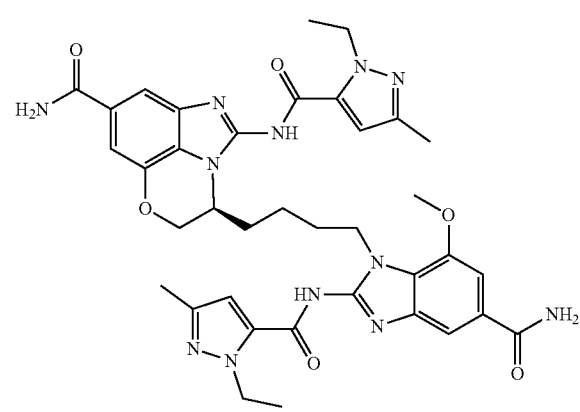

To the MeOH (0.5 mL) solution of (S,E)-3-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-3,4-dihydro-5-oxa-1,2a-diazaacenaphthylene-7-carboxamide (Example 15, 5.5 mg, 0.0073 mmol) was added 10% Pd/C (5.5 mg) and the mixture was hydrogenated under $H_2$ balloon for 18 hrs. The mixture was filtered through a celite pad. The filtrate was concentrated under vacuum to purified by reverse phase HPLC, eluated with MeCN/$H_2$O/TFA to give title compound (S)-3-(4-(5-carbamoyl-2-(1-ethyl-3-methyl-1H-pyrazole-5-carboxamido)-7-methoxy-1H-benzo[d]imidazol-1-yl)butyl)-2-(1-ethyl-3-methyl-1H-pyrazole-5-carboxamido)-3,4-dihydro-5-oxa-1,2a-diazaacenaphthylene-7-carboxamide 16 as white solid (1.4 mg). MS m/z (ESI): 751 [M+1].

Example 17

3-(2-((3-(5-carbamoyl-2-(1-ethyl-3-methyl-1H-pyrazole-5-carboxamido)-7-methoxy-1H-benzo[d]imidazol-1-yl)propyl)amino)ethyl)-2-(1-ethyl-3-methyl-1H-pyrazole-5-carboxamido)-3,4-dihydro-5-oxa-1,2a-diazaacenaphthylene-7-carboxamide 17

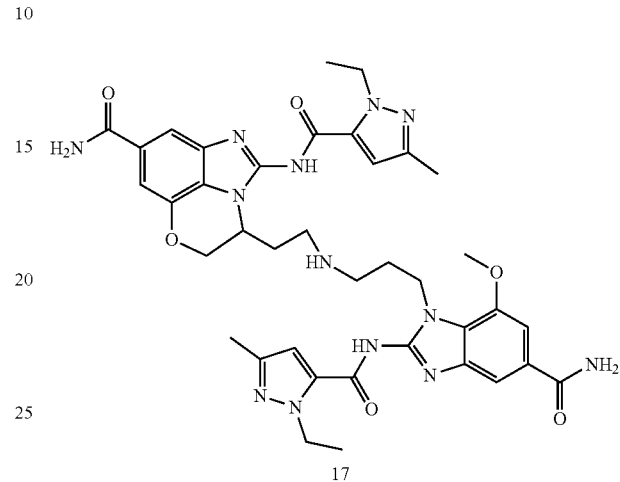

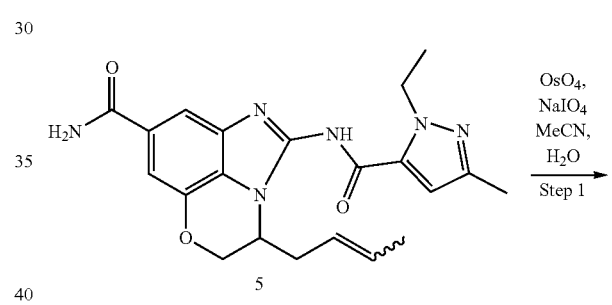

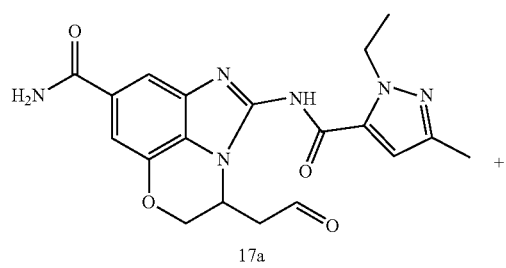

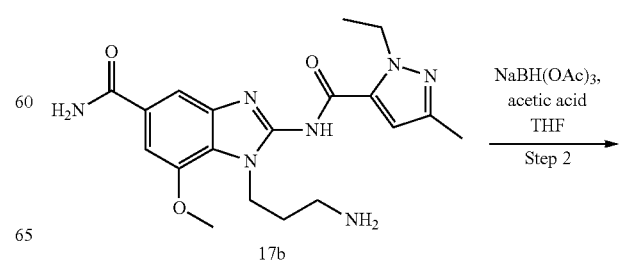

-continued

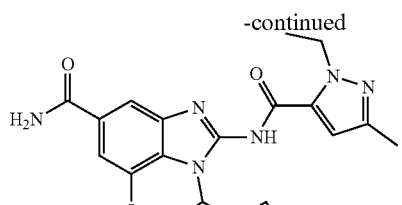

17

Step 1

2-(1-ethyl-3-methyl-1H-pyrazole-5-carboxamido)-3-(2-oxoethyl)-3,4-dihydro-5-oxa-1,2a-diazaacenaphthylene-7-carboxamide 17a To 3-(but-2-en-1-yl)-2-(1-ethyl-3-methyl-1H-pyrazole-5-carboxamido)-3,4-dihydro-5-oxa-1,2a-diazaacenaphthylene-7-carboxamide (Example 5, 55 mg, 0.135 mmol) in MeCN (5 mL) under nitrogen atmosphere at 0° C. was added $OsO_4$ (1.71 mL, 0.269 mmol, 4 wt % in $H_2O$, 2 eq). The resulting solution was stirred at 0° C. for 5 min before adding $NaIO_4$ (144 mg, 0.675 mmol, 5 eq) in water (1 mL). The resulting solution was stirred for 2 hours before quenching with saturated $NaHCO_3$ solution (30 mL), and then extracted with EtOAc (30 mL×3). The organic layer was combined, dried over $Na_2SO_4$ and filtered. The solvent was concentrated under vacuum to give title compound 2-(1-ethyl-3-methyl-1H-pyrazole-5-carboxamido)-3-(2-oxoethyl)-3,4-dihydro-5-oxa-1,2a-diazaacenaphthylene-7-carboxamide 17a, which was used in the next step without further purification.

Step 2

3-(2-((3-(5-carbamoyl-2-(1-ethyl-3-methyl-1H-pyrazole-5-carboxamido)-7-methoxy-1H-benzo[d]imidazol-1-yl)propyl)amino)ethyl)-2-(1-ethyl-3-methyl-1H-pyrazole-5-carboxamido)-3,4-dihydro-5-oxa-1,2a-diazaacenaphthylene-7-carboxamide 17

To solution of 2-(1-ethyl-3-methyl-1H-pyrazole-5-carboxamido)-3-(2-oxoethyl)-3,4-dihydro-5-oxa-1,2a-diazaacenaphthylene-7-carboxamide 17a (Crude, 0.135 mmol) and 1-(3-aminopropyl)-2-(1-ethyl-3-methyl-1H-pyrazole-5-carboxamido)-7-methoxy-1H-benzo[d]imidazole-5-carboxamide 17b (WO2017175156, 28 mg, 0.07 mmol) in DCM (5 mL) was added acetic acid (0.5 mL). The resulting solution was stirred at room temperature for 5 min before adding $NaBH(OAc)_3$ (80 mg, 0.377 mmol, 5 eq). The resulting solution was stirred overnight at room recapture. The mixture was diluted with brine (30 mL), extracted with EtOAc (30 mL×3). The mixture was concentrated under vacuum and then purified by prep-HPLC, eluated with MeCN/$H_2O$/TFA to give title compound 3-(2-((3-(5-carbamoyl-2-(1-ethyl-3-methyl-1H-pyrazole-5-carboxamido)-7-methoxy-1H-benzo[d]imidazol-1-yl)propyl)amino)ethyl)-2-(1-ethyl-3-methyl-1H-pyrazole-5-carboxamido)-3,4-dihydro-5-oxa-1,2a-diazaacenaphthylene-7-carboxamide 17 (9.6 mg, 17%). MS m/z (ESI): 780 [M+1].

Example 18

(S)-3-(3-(5-carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 18

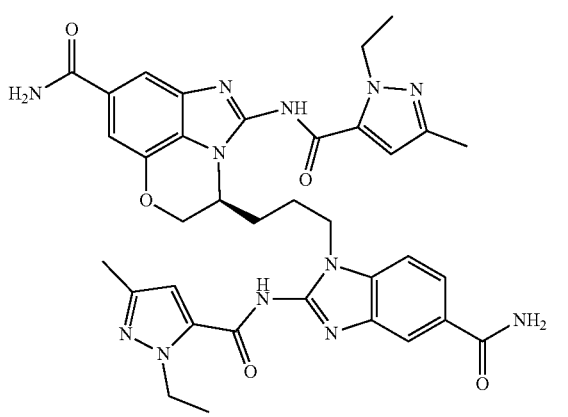

18

The procedure of synthesis for example 18 is similar with example 13. In the step 2, the intermediate 4-chloro-3-methoxy-5-nitrobenzamide is replaced by 4-chloro-3-nitrobenzamide. MS m/z (ESI): 707 [M+1]; $^1$H NMR (400 MHz, Methanol-$d_4$) δ 7.90 (s, 1H), 7.77 (d, J=8.2 Hz, 1H), 7.54 (s, 1H), 7.44-7.37 (m, 1H), 7.32 (s, 1H), 6.62 (s, 1H), 6.54 (s, 1H), 4.64 (d, J=12.3 Hz, 6H), 4.34-4.23 (m, 3H), 3.02 (s, 1H), 2.88 (s, 1H), 2.19 (d, J=9.0 Hz, 7H), 2.12 (s, 3H), 1.38 (d, J=6.9 Hz, 6H).

Example 19

(S)-3-(3-(5-carbamoyl-2-(1-ethyl-3-methyl-1H-pyrazole-5-carboxamido)-7-(3-hydroxypropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 19

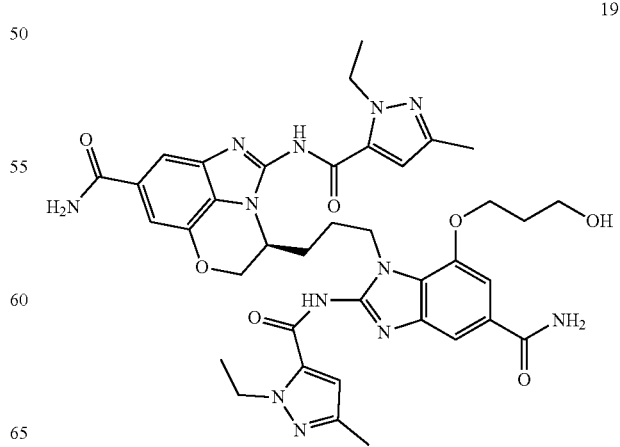

19

The procedure of synthesis for example 19 is similar with example 13. In the step 2, the intermediate 4-chloro-3-methoxy-5-nitrobenzamide is replaced by 3-(3-((tert-butyldimethylsilyl)oxy)propoxy)-4-chloro-5-nitrobenzamide. MS m/z (ESI): 781 [M+1].

Example 20

(S)-3-(3-(5-carbamoyl-2-(1-ethyl-3-methyl-1H-pyrazole-5-carboxamido)-7-(2-hydroxyethoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 20

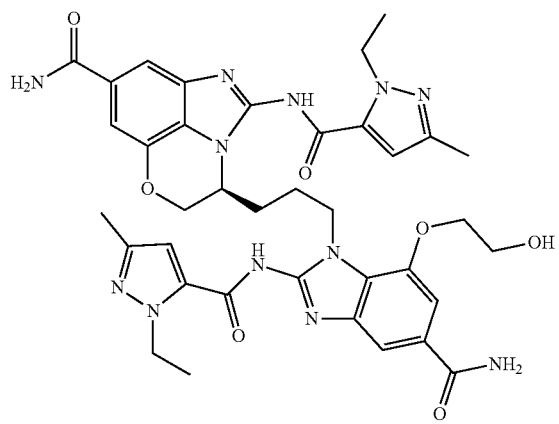

The procedure of synthesis for example 20 is similar with example 13. In the step 2, the intermediate 4-chloro-3-methoxy-5-nitrobenzamide is replaced by 3-(2-((tert-butyldimethylsilyl)oxy)ethoxy)-4-chloro-5-nitrobenzamide. MS m/z (ESI): 767 [M+1]; 1H NMR (400 MHz, MeOD) δ 7.42 (s, 2H), 7.20 (s, 2H), 6.53 (s, 1H), 6.42 (s, 1H), 4.54 (d, J=19.6 Hz, 4H), 4.44 (s, 4H), 4.16 (d, J=11.6 Hz, 1H), 4.07 (s, 1H), 3.98 (s, 1H), 3.74-3.67 (m, 1H), 3.63 (d, J=13.5 Hz, 1H), 2.09 (d, J=15.0 Hz, 7H), 2.01 (s, 4H), 1.27 (s, 8H).

Example 21

(S)-3-(3-(5-carbamoyl-2-(1-ethyl-3-methyl-1H-pyrazole-5-carboxamido)-7-(3-methoxypropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 21

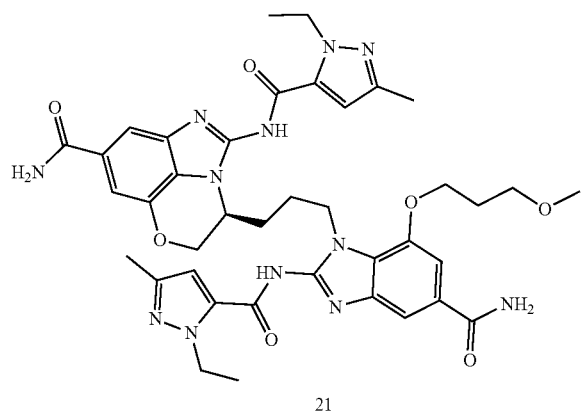

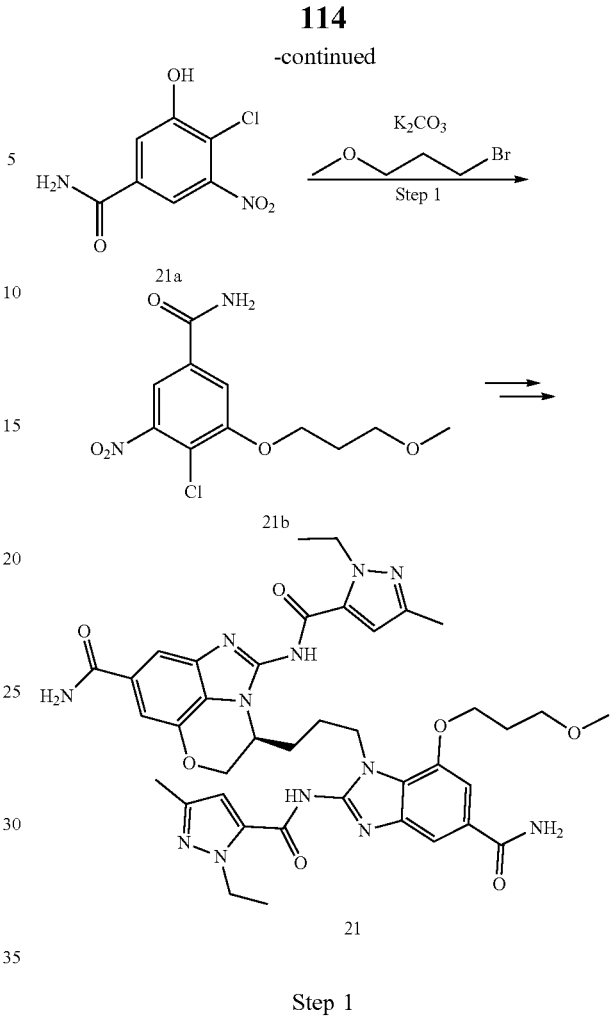

Step 1

4-chloro-3-(3-methoxypropoxy)-5-nitrobenzamide 21b

To a suspension of 4-chloro-3-hydroxy-5-nitrobenzamide (1.00 g, 4.62 mmol) in DMF (15 mL) was added 1-bromo-3-methoxypropane (1.06 g, 6.93 mmol) and $K_2CO_3$ (1.91 mg, 13.9 mmol). The reaction mixture was stirred at 60° C. in a sealed tube. After 3 hr, the reaction was cooled to RT and poured into water. The resulting light yellow precipitate was collected by filtration and washed with diethyl ether to provide the title compound 21b 4-chloro-3-(3-methoxypropoxy)-5-nitrobenzamide (1.1 g, 3.8 mmol, 83 percent yield). MS m/z (ESI): 289 [M+1].

(S)-3-(3-(5-carbamoyl-2-(1-ethyl-3-methyl-1H-pyrazole-5-carboxamido)-7-(3-methoxypropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 21

The procedure of synthesis for example 21 is similar with example 13. In the step 2, the intermediate 4-chloro-3-methoxy-5-nitrobenzamide is replaced by 4-chloro-3-(3-methoxypropoxy)-5-nitrobenzamide. MS m/z (ESI): 795 [M+1]; $^1$H NMR (400 MHz, Methanol-$d_4$) δ 7.50 (d, J=5.9 Hz, 2H), 7.32 (s, 1H), 7.27 (s, 1H), 6.67 (s, 1H), 6.63 (s, 1H), 4.64 (d, J=10.0 Hz, 4H), 4.43 (s, 1H), 4.27 (d, J=12.2 Hz, 1H), 4.13 (s, 1H), 4.04 (s, 1H), 3.45 (s, 2H), 3.33 (s, 8H), 2.21 (d, J=19.2 Hz, 6H), 1.89 (s, 2H), 1.39 (d, J=8.6 Hz, 8H), 1.31 (s, 2H).

Example 22

(S)-3-(3-(5-carbamoyl-2-(1-ethyl-3-methyl-1H-pyrazole-5-carboxamido)-7-(3-morpholinopropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

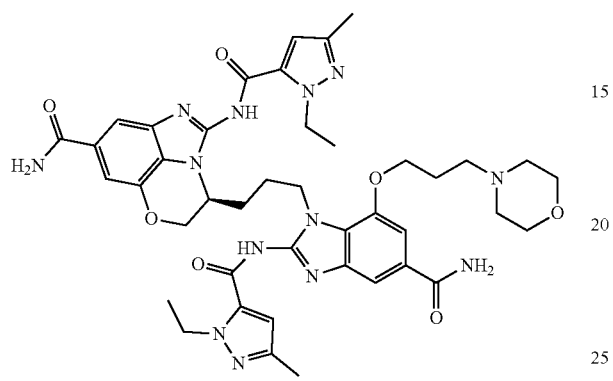

22

The procedure of synthesis for example 20 is similar with example 13. In the step 2, the intermediate 4-chloro-3-methoxy-5-nitrobenzamide is replaced by 4-chloro-3-(3-morpholinopropoxy)-5-nitrobenzamide. MS m/z (ESI): 850 [M+1]; $^1$H NMR (400 MHz, Methanol-$d_4$) δ 7.47 (d, J=4.2 Hz, 2H), 7.32 (s, 1H), 7.19 (s, 1H), 6.67 (s, 1H), 6.53 (s, 1H), 4.78 (s, 1H), 4.65 (d, J=11.3 Hz, 4H), 4.57-4.46 (m, 2H), 4.30 (t, J=12.2 Hz, 2H), 4.09 (d, J=17.0 Hz, 3H), 3.96 (s, 1H), 3.83 (d, J=12.1 Hz, 2H), 3.46 (d, J=14.3 Hz, 2H), 3.30 (d, J=26.8 Hz, 6H), 3.13 (s, 2H), 2.22 (d, J=19.0 Hz, 6H), 2.12 (s, 5H), 1.94 (s, 1H), 1.46-1.34 (m, 6H).

Example 23

(S)-3-((5-carbamoyl-1-(3-(7-carbamoyl-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-1H-benzo[d]imidazol-7-yl)oxy)propyl dihydrogen phosphate 23

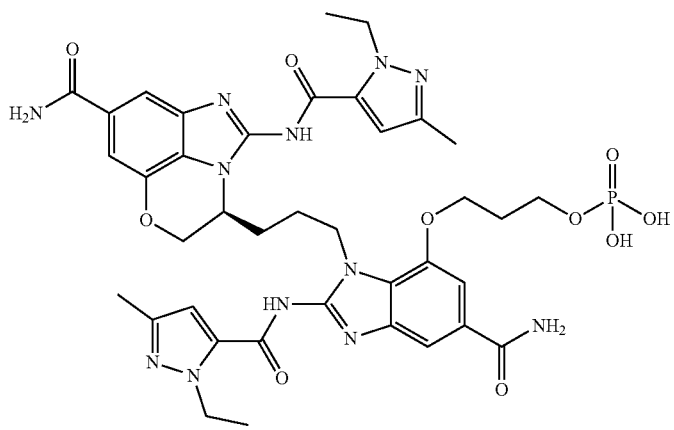

23

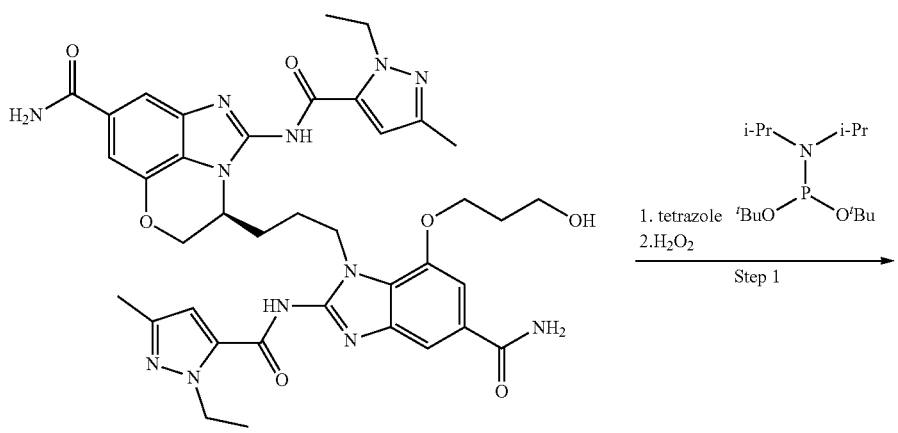

19

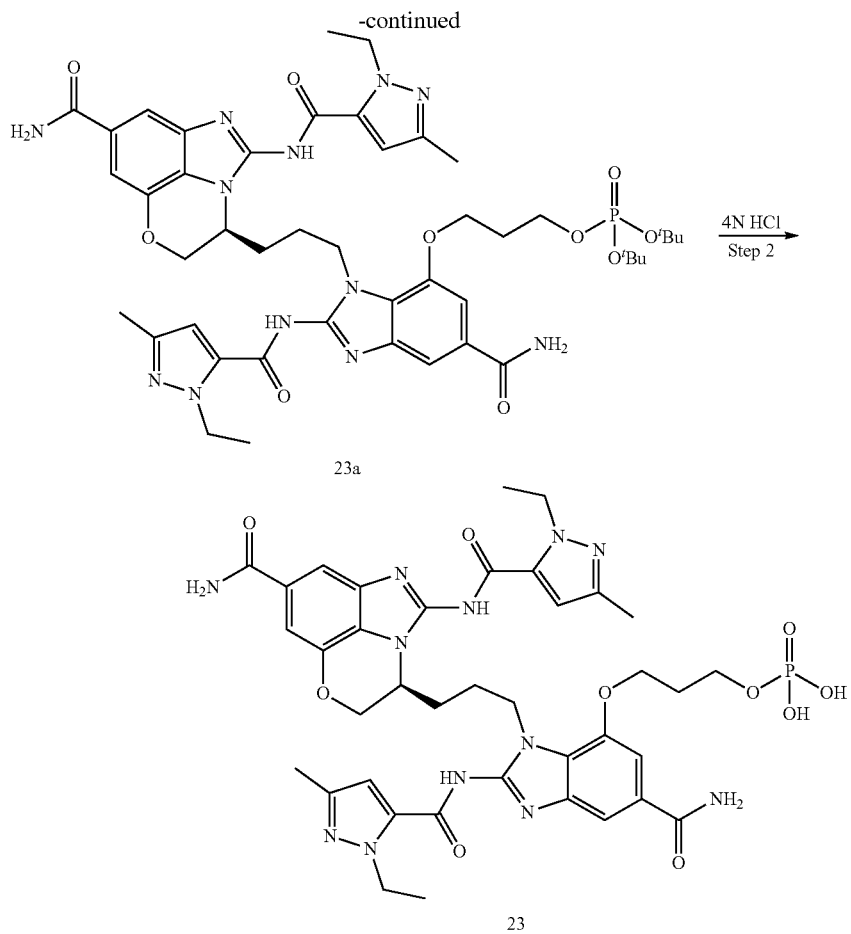

Step 1

(S)-di-tert-butyl (3-((5-carbamoyl-1-(3-(7-carbamoyl-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-1H-benzo[d]imidazol-7-yl)oxy)propyl) phosphate 23a To (S)-3-(3-(5-carbamoyl-2-(1-ethyl-3-methyl-1H-pyrazole-5-carboxamido)-7-(3-hydroxypropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide (Example 19, 15 mg, 0.019 mmol) in DMF (0.5 mL) was added tetrazole (0.21 mL, 0.096 mmol, 5 eq, 0.45 M in MeCN). The resulting solution was concentrated under vacuum to remove MeCN before cooling down to 0° C. Di-tert-butylchlorophosphine (21 mg, 0.077 mmol, 4 eq) in DMF (0.5 mL) was added to the mixture under nitrogen atmosphere. The resulting solution was slowly warm up to room temperature and stirred for 1 hour before cooled to 0° C. again. $H_2O_2$ (0.02 mL) was added to the mixture at 0° C., and then the solution was slowly warm up to room temperature again and stirred for 1 hour. The mixture was then purified by prep-HPLC, eluated with MeCN/$H_2O$ to give title compound (3-((5-carbamoyl-1-(3-(7-carbamoyl-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-1H-benzo[d]imidazol-7-yl)oxy)propyl) phosphate 23a.

Step 2

(S)-3-((5-carbamoyl-1-(3-(7-carbamoyl-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-1H-benzo[d]imidazol-7-yl)oxy)propyl dihydrogen phosphate 23

To (3-((5-carbamoyl-1-(3-(7-carbamoyl-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-1H-benzo[d]imidazol-7-yl)oxy)propyl) phosphate 23a (all from above) in water (1 mL) was added 4 N HCl in dioxane (0.1 mL). The resulting solution was stirred at room recapture for 30 min. The mixture was basified by sat $NH_4HCO_3$ at 0° C., and then purified by prep-HPLC, eluated with MeCN/$H_2O$/$NH_4HCO_3$ to give title compound (S)-3-((5-carbamoyl-1-(3-(7-carbamoyl-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-1H-benzo[d]imidazol-7-yl)oxy)propyl dihydrogen phosphate 23 (2.2 mg, 13% two steps). MS m/z (ESI): 861 [M+1].

Example 24 and 25

(S)-3-(3-(5-carbamoyl-7-(3-(dimethylamino)
propoxy)-2-(1-ethyl-3-methyl-1H-pyrazole-5-car-
boxamido)-1H-benzo[d]imidazol-1-yl)propyl)-2-(1-
ethyl-3-methyl-1H-pyrazole-5-carboxamido)-3,4-
dihydro-5-oxa-1,2a-diazaacenaphthylene-7-
carboxamide 24

(S)-3-(3-(7-(allyloxy)-5-carbamoyl-2-(1-ethyl-3-
methyl-1H-pyrazole-5-carboxamido)-1H-benzo[d]
imidazol-1-yl)propyl)-2-(1-ethyl-3-methyl-1H-pyra-
zole-5-carboxamido)-3,4-dihydro-5-oxa-1,2a-
diazaacenaphthylene-7-carboxamide 25

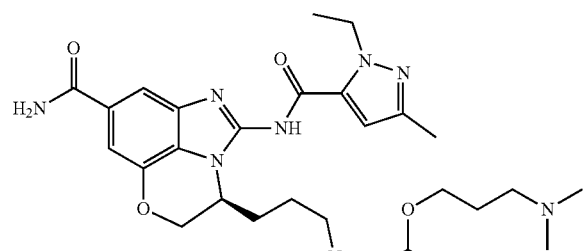

24

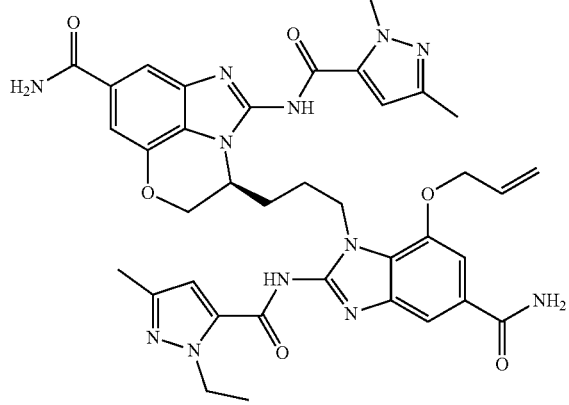

25

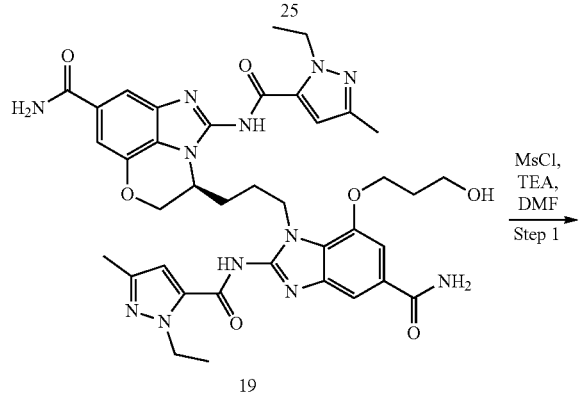

19

MsCl,
TEA,
DMF
Step 1

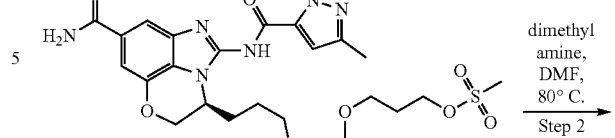

dimethyl
amine,
DMF,
80° C.
Step 2

24a

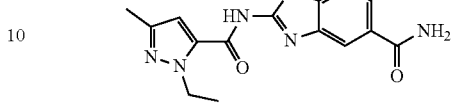

+

24

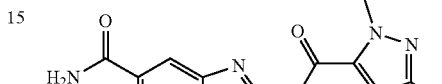

25

Step 1

(S)-3-((5-carbamoyl-1-(3-(7-carbamoyl-2-(1-ethyl-3-
methyl-1H-pyrazole-5-carboxamido)-3,4-dihydro-5-
oxa-1,2a-diazaacenaphthylen-3-yl)propyl)-2-(1-
ethyl-3-methyl-1H-pyrazole-5-carboxamido)-1H-
benzo[d]imidazol-7-yl)oxy)propyl methanesulfonate
24a To (S)-3-(3-(5-carbamoyl-2-(1-ethyl-3-methyl-1H-pyra-
zole-5-carboxamido)-7-(3-hydroxypropoxy)-1H-benzo[d]
imidazol-1-yl)propyl)-2-(1-ethyl-3-methyl-1H-pyrazole-5-
carboxamido)-3,4-dihydro-5-oxa-1,2a-diazaacenaphth-
ylene-7-carboxamide (Example 19, 32 mg, 0.041 mmol) in
DMF (1 mL) at 0° C. under nitrogen atmosphere was added
TEA (5 mg, 0.082 mmol) in DMF (0.2 mL) followed by
addition of MsCl (4.68 mg, 0.041 mmol) in DMF (0.2 mL).

The resulting solution was stirred at 0° C. for 1.5 hours. The resulting solution was used for next step without further purification.

Step 2

(S)-3-(3-(5-carbamoyl-7-(3-(dimethylamino)propoxy)-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 24

(S)-3-(3-(7-(allyloxy)-5-carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 25

To above crude solution was added K₂CO₃ (28 mg, 0.205 mmol, 5 eq) followed by dimethylamine (0.23 mL, 0.45 mmol, 11 eq). The resulting solution was stirred 1 hour at 80° C. After cooling down, the mixture was purified by prep-HPLC, eluated with AcCN/H₂O/NH₄HCO₃ to give title compound (S)-3-(3-(5-carbamoyl-7-(3-(dimethylamino)propoxy)-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 24 (3.1 mg, 9%) with MS m/z (ESI): 808 [M+1] and (S)-3-(3-(7-(allyloxy)-5-carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide 25 (2.1 mg, 7%). MS m/z (ESI): 763 [M+1].

Example 26

1-(1-ethyl-3-methyl-1H-pyrazole-5-carboxamido)-10-(hydroxymethyl)-7,8,9,10-tetrahydro-6-oxa-2,10a-diazacycloocta[cd]indene-4-carboxamide 26

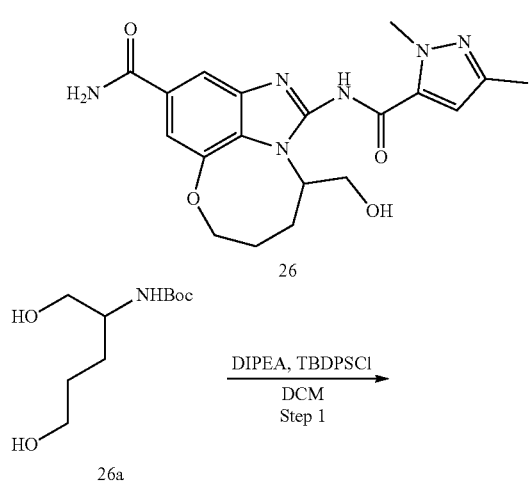

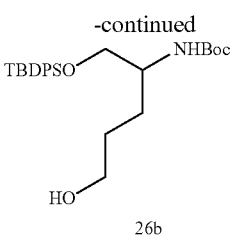

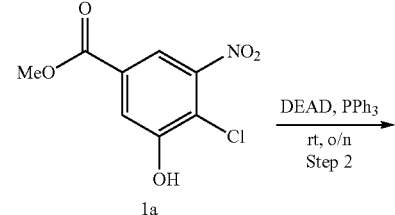

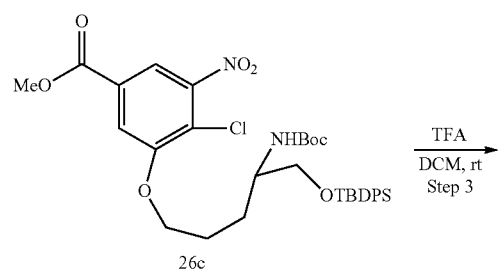

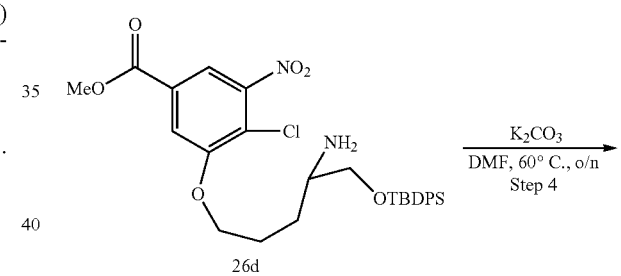

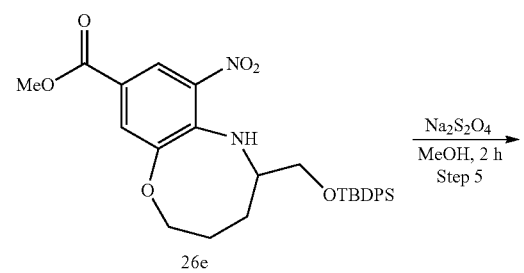

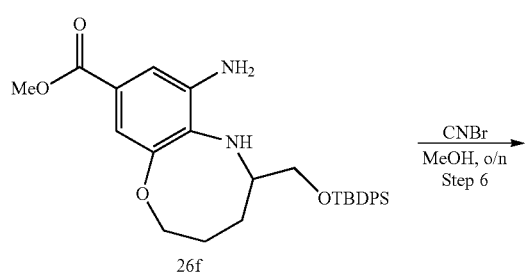

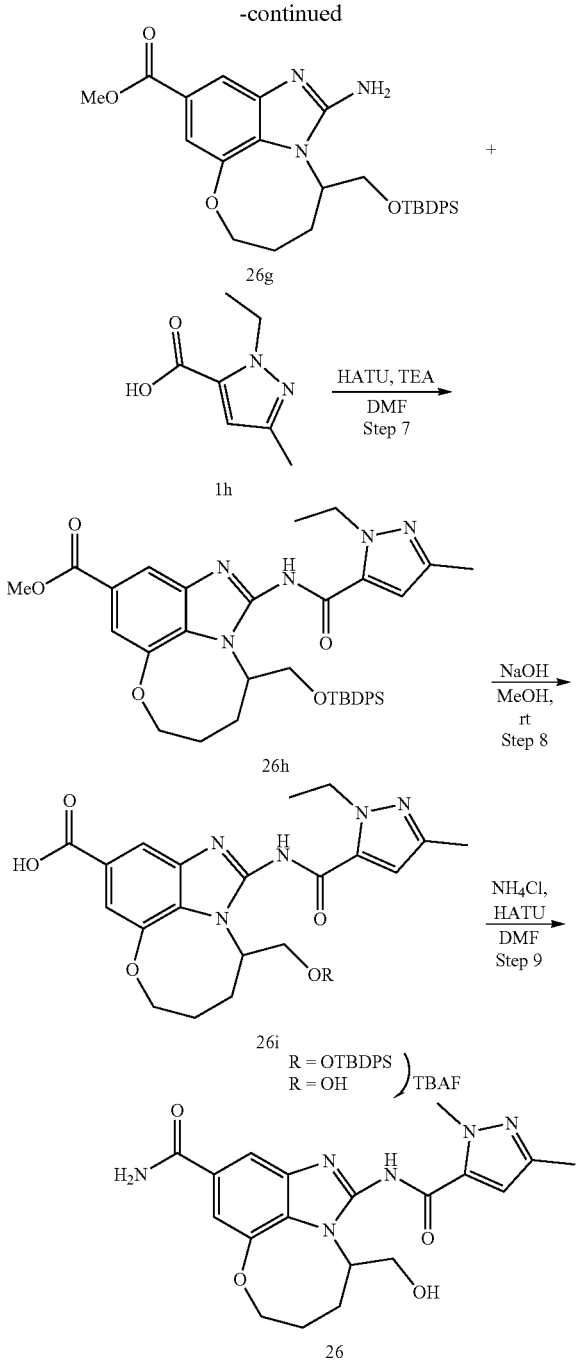

phenylsilyl)oxy)-5-hydroxypentan-2-yl)carbamate 26b (lower $R_f$ on TLC, 1.8 g, 22%).

Step 2-8 of Examples 26 was Prepared with the Similar Procedures as Example 5

In step 8, the mixture was acidified by TFA at room temperature and stirred for 1 hour. During this process, TBDPS will fall off. If not, it can be removed by TBAE Step 9 of Examples 26 was Prepared with the Similar Procedures as Example 5

In step 9, the mixture was purified by prep-HPLC, eluated with MeCN/H$_2$O/TFA to give title compound 1-(1-ethyl-3-methyl-1H-pyrazole-5-carboxamido)-10-(hydroxymethyl)-7,8,9,10-tetrahydro-6-oxa-2,10a-diazacycloocta[cd]indene-4-carboxamide 26. MS m/z (ESI): 413 [M+1].

Example 27

10-allyl-1-(1-ethyl-3-methyl-1H-pyrazole-5-carboxamido)-7,8,9,10-tetrahydro-6-oxa-2,10a-diazacycloocta[cd]indene-4-carboxamide 27

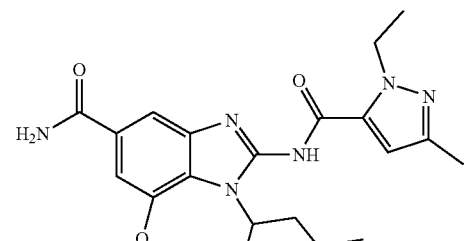

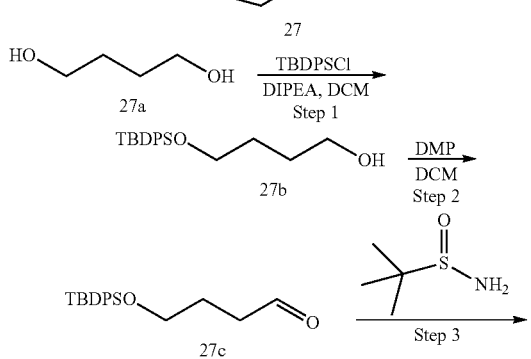

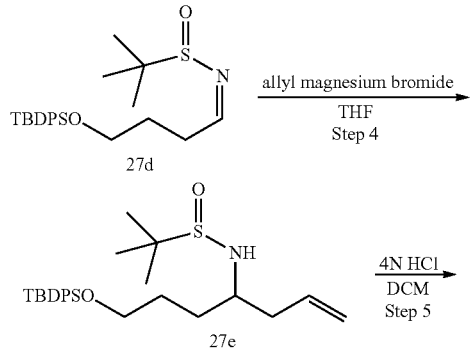

Step 1 tert-butyl (1-((tert-butyldiphenylsilyl)oxy)-5-hydroxypentan-2-yl)carbamate 26b

To the dichloromethane solution (200 mL) of tert-butyl (1,5-dihydroxypentan-2-yl)carbamate 26a (4 g, 19.5 mmol) at room temperature was added DIPEA (6.78 mL, 39 mmol, 2 eq) and TBDPSCl (5.06 mL, 19.5 eq). The resulting solution was stirred at 45° C. for 60 hours. The mixture was concentrated under vacuum and purified by silica gel column (330 g ISCO cartridge with 1:4:10 acetone:ether:hexanes) to give title compound tert-butyl (1-((tert-butyldi-

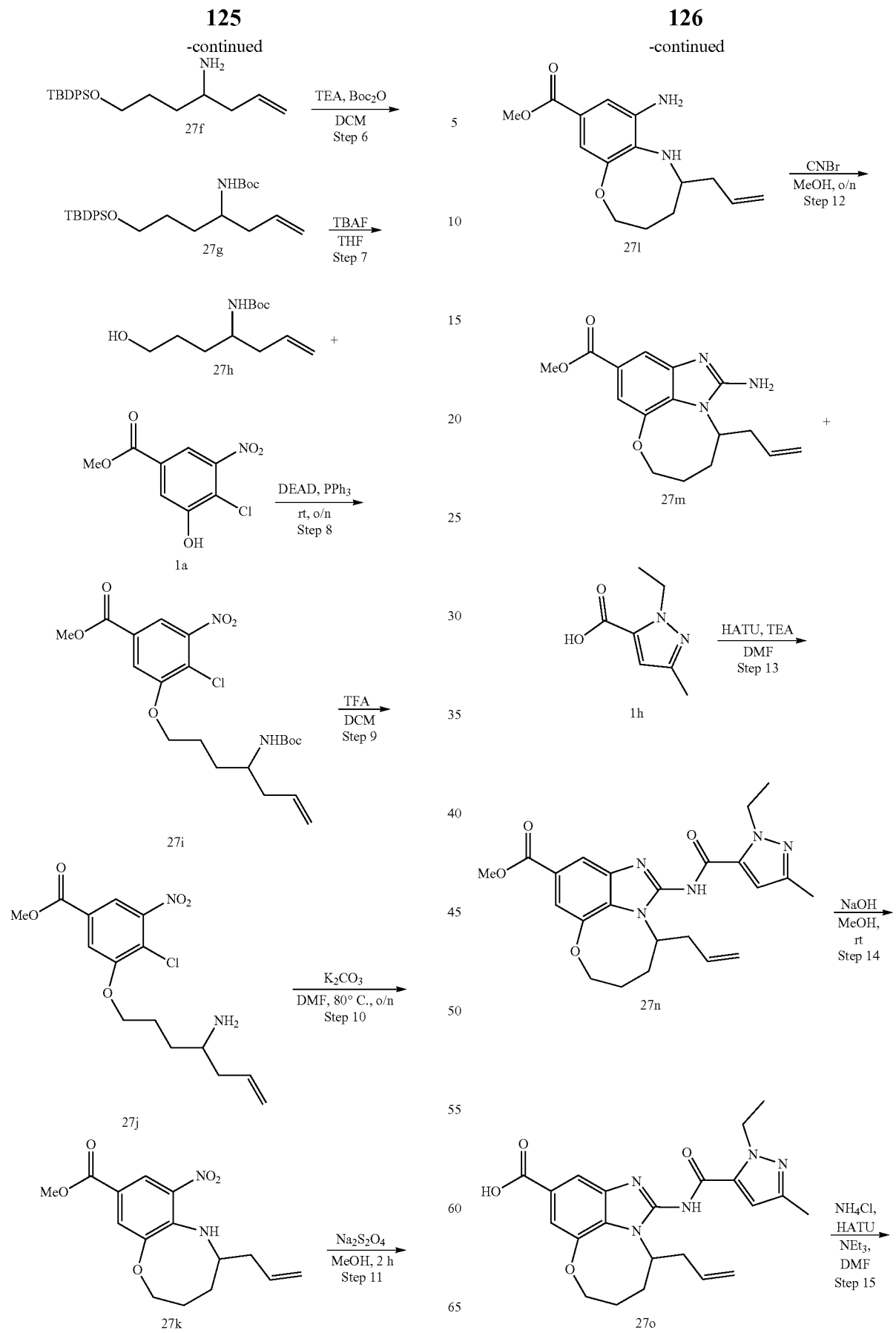

-continued

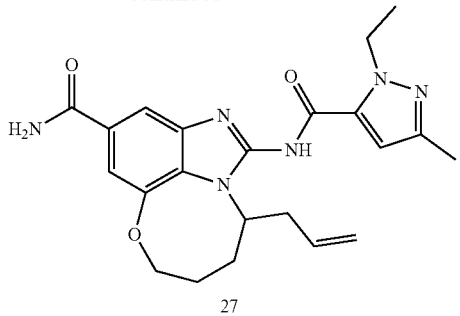

27

Step 1

4-((tert-butyldiphenylsilyl)oxy)butan-1-ol 27b

To the dichloromethane solution (600 mL) of tert-butyl butane-1,4-diol 27a (10 g, 111 mmol) and DIPEA (21.3 mL, 122 mmol, 1.1 eq) at room temperature was added TBDPSCl (31.6 mL, 122 mmol, 1.1 eq). The resulting solution was stirred at room temperature for 72 hours. The mixture was concentrated under vacuum and purified by silica gel column (330 g ISCO cartridge with 0-40% ethyl acetate in hexanes) to give title compound 4-((tert-butyldiphenylsilyl)oxy)butan-1-ol 27b (36 g, 98%).

Step 2

4-((tert-butyldiphenylsilyl)oxy)butanal 27c

To the dichloromethane solution (300 mL) of 4-((tert-butyldiphenylsilyl)oxy)butan-1-ol 27b (23.5 g, 71.6 mmol) under nitrogen atmosphere at room temperature was added DMP (45.6 g, 107 mmol, 1.5 eq). The resulting solution was stirred at room temperature for 2 hours before worked up with saturated NaCl solution. After extraction with EtOAc (500 mL×3). The organic layer was combined, dried over Na$_2$SO$_4$ and filtered. The solvent was concentrated under vacuum to give title compound 4-((tert-butyldiphenylsilyl)oxy)butanal 27c, which was used in the next step without further purification.

Step 3

N-(4-((tert-butyldiphenylsilyl)oxy)butylidene)-2-methylpropane-2-sulfinamide 27d To the THF solution (500 mL) of 4-((tert-butyldiphenylsilyl)oxy)butanal 27c (Crude, 71.6 mmol) and 2-Methyl-2-propanesulfinamide (9.5 g, 78.8 mmol, 1.1 eq) under nitrogen atmosphere at room temperature was added Ti(OEt)$_4$ (27 mL, 128 mmol, 1.8 eq). The resulting solution was stirred at room temperature for 1 hour before worked up with saturated NaHCO$_3$ solution. After extraction with EtOAc (500 mL×3). The organic layer was combined, dried over Na$_2$SO$_4$ and filtered. The solvent was concentrated under vacuum to give title compound N-(4-((tert-butyldiphenylsilyl)oxy) butylidene)-2-methylpropane-2-sulfinamide 27d, which was used in the next step without further purification.

Step 4

N-(7-((tert-butyldiphenylsilyl)oxy)hept-1-en-4-yl)-2-methylpropane-2-sulfinamide 27e To the THF solution (600 mL) of N-(4-((tert-butyldiphenylsilyl)oxy)butylidene)-2-methylpropane-2-sulfinamide 27d (Crude, 71.6 mmol) under nitrogen atmosphere at −78° C. was added allyl magnesium bromide (143 mL, 143 mmol, 2 eq). The resulting solution was stirred at −78° C. for 1 hour before worked up with saturated NH$_4$Cl solution. After extraction with EtOAc (500 mL×3). The organic layer was combined, dried over Na$_2$SO$_4$ and filtered. The solvent was concentrated under vacuum. The resulting mixture was purified by silica gel column (2*330 g ISCO cartridge with 0-50% EtOAc in hexanes) to give title compound N-(7-((tert-butyldiphenylsilyl)oxy)hept-1-en-4-yl)-2-methylpropane-2-sulfinamide 27e (8.2 g, 24% three steps).

Step 5

7-((tert-butyldiphenylsilyl)oxy)hept-1-en-4-amine 27f

To the DCM solution (600 mL) of N-(7-((tert-butyldiphenylsilyl)oxy)hept-1-en-4-yl)-2-methylpropane-2-sulfinamide 27e (8.2 g, 17.4 mmol) at room temperature was added 4N HCl in dioxane (13 mL, 52.2 mmol, 3 eq). The resulting solution was stirred overnight at room temperature. The solvent was concentrated under vacuum to give title compound 7-((tert-butyldiphenylsilyl)oxy)hept-1-en-4-amine 27f, which was used in the next step without further purification.

Step 6 tert-butyl (7-((tert-butyldiphenylsilyl)oxy)hept-1-en-4-yl)azanecarboxylate 27g

To the DCM:THF solution (1:1, 300 mL) of 7-((tert-butyldiphenylsilyl)oxy)hept-1-en-4-amine 27f (Crude, 17.4 mmol) at room temperature was added NEt$_3$ (8.23 mL, 87 mmol, 5 eq) and Boc$_2$O (7.59 g, 34.8 mmol, 2 eq). The resulting solution was stirred at room temperature for 48 hours. The solvent was concentrated under vacuum. The resulting mixture was purified by silica gel column (120 g ISCO cartridge with 0-25% EtOAc in hexanes) to give title compound tert-butyl (7-((tert-butyldiphenylsilyl)oxy)hept-1-en-4-yl)-azanecarboxylate 27g (8.14 g, 98% two steps).

Step 7 tert-butyl (7-hydroxyhept-1-en-4-yl)azanecarboxylate 27h

To the THF solution (300 mL) of 7 tert-butyl (7-((tert-butyldiphenylsilyl)oxy)hept-1-en-4-yl)azanecarboxylate 27g (8.14 g, 17.5 mmol) at room temperature was added TBAF (18.34 mL, 18.3 mmol, 1.05 eq). The resulting solution was stirred at room temperature for 6 hours. The solvent was concentrated under vacuum. The resulting mixture was purified by silica gel column (80 g ISCO cartridge with 0-100% EtOAc in hexanes) to give title compound tert-butyl (7-hydroxyhept-1-en-4-yl)azanecarboxylate 27h (1.8 g, 45%).

Step 8-15 of Examples 27 was Prepared with the Similar Procedures as Example 5

The mixture was purified by prep-HPLC, eluated with ACN/H$_2$O/TFA to give title compound 10-allyl-1-(1-ethyl-3-methyl-1H-pyrazole-5-carboxamido)-7,8,9,10-tetrahydro-6-oxa-2,10a-diazacyclooocta[cd]indene-4-carboxamide 27. MS m/z (ESI): 423 [M+1]. $^1$H NMR (400 MHz, MeOD): δ 7.82 (s, 1H), 7.57 (s, 1H), 6.78 (s, 1H), 5.71-5.61 (m, 2H), 4.83-4.64 (m, 3H), 3.78 (m, 1H), 3.01-2.72 (m, 3H), 2.34-2.09 (m, 7H), 1.74 (m, 1H), 1.48 (t, J=6.4 Hz, 3H).

Example 28

(E)-6-((S)-7-carbamoyl-2-(1-ethyl-3-methyl-1H-pyrazole-5-carboxamido)-3,4-dihydro-5-oxa-1,2a-diazaacenaphthylen-3-yl)-2-(2-(5,6-dimethoxybenzo[b]thiophen-2-yl)-2-oxoethyl)hex-4-enoic acid 28

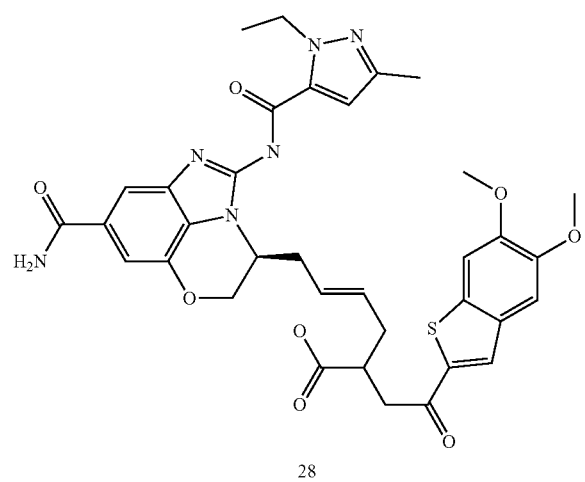

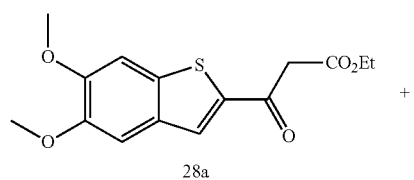

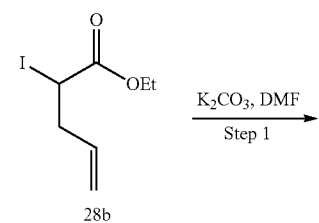

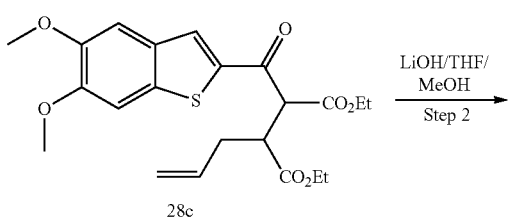

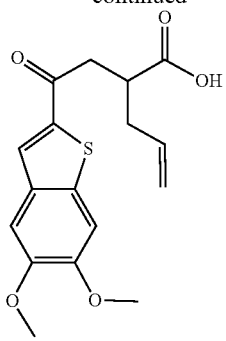

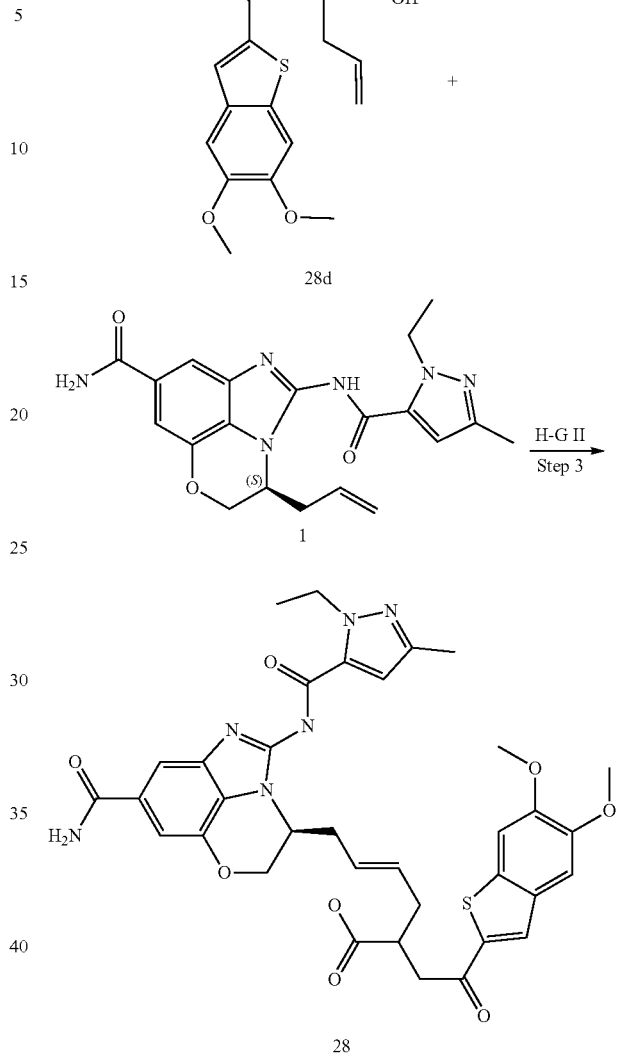

Step 1 diethyl 2-allyl-3-(5,6-dimethoxybenzo[b]thiophene-2-carbonyl)succinate 28c

To a solution of ethyl 2-iodopent-4-enoate 28b (45 mg, 0.146 mmol) in DMF (1 mL) were added ethyl 3-(5,6-dimethoxybenzo[b]thiophen-2-yl)-3-oxopropanoate 28a (45 mg, 0.146 mmol, purchased from www.specs.net) and $K_2CO_3$ (30 mg, 0.217 mmol). The mixture was stirred at room temperature for 18h. The mixture was diluted with water, extracted with EtOAc. The organic layer was combined, dried over $Na_2SO_4$, filtered and concentrated. The residue was purified by silica gel column (eluted with 0-100% EtOAc in hexane) to give title compound diethyl 2-allyl-3-(5,6-dimethoxybenzo[b]thiophene-2-carbonyl)succinate 28c (55 mg).

MS m/z (ESI): 435 [M+1].

Step 2

2-(2-(5,6-dimethoxybenzo[b]thiophen-2-yl)-2-oxo-ethyl)pent-4-enoic acid 28d To a solution of diethyl 2-allyl-3-(5,6-dimethoxybenzo[b]thiophene-2-carbonyl)succinate 28c (41 mg) in THF (1 mL) was added 1M LiOH (0.5 mL) and MeOH (0.5 mL). The resulting mixture was stirred at room temperature for 6h, acidified with 1M HCl, extracted with EtOAc. The organic layer was combined, dried over $Na_2SO_4$, filtered and concentrated. The residue was purified by prep-HPLC, eluated with $MeCN/H_2O/TFA$ to give title compound 2-(2-(5,6-dimethoxybenzo[b]thiophen-2-yl)-2-oxoethyl)pent-4-enoic acid 28d (14 mg). MS m/z (ESI): 335 [M+1].

Step 3

(E)-6-((S)-7-carbamoyl-2-(1-ethyl-3-methyl-1H-pyrazole-5-carboxamido)-3,4-dihydro-5-oxa-1,2a-diazaacenaphthylen-3-yl)-2-(2-(5,6-dimethoxybenzo[b]thiophen-2-yl)-2-oxoethyl)hex-4-enoic acid 28

The title compound was prepared from Example 1 and compound 28d with the same method as step 12 of Example 14. MS m/z (ESI): 701 [M+1].

Example 29

(S)-4-allyl-2-(1-ethyl-3-methyl-1H-pyrazole-5-carboxamido)-5,6-dihydro-4H-imidazo[1,5,4-de]quinoxaline-8-carboxamide 29

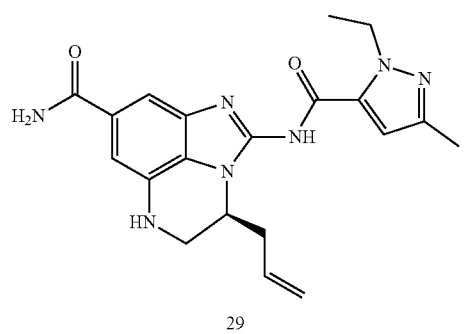

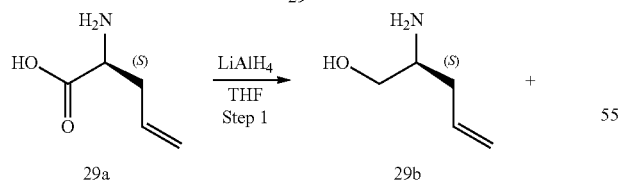

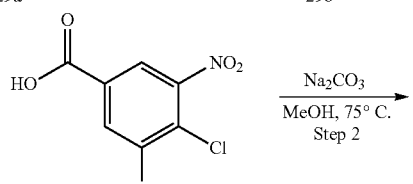

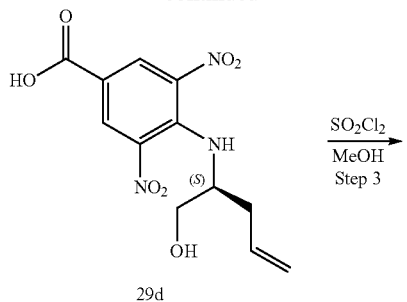

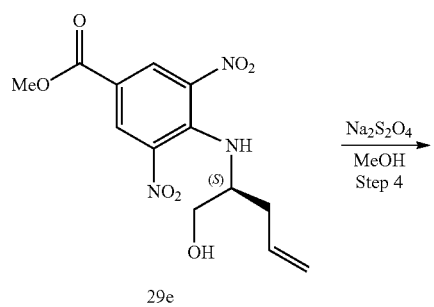

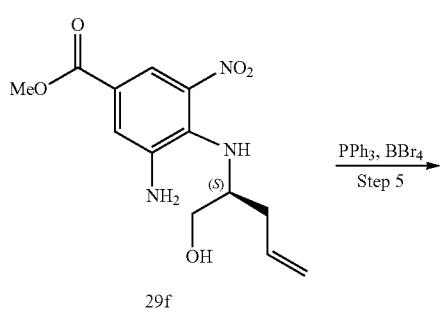

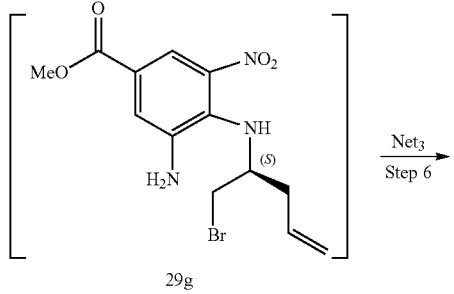

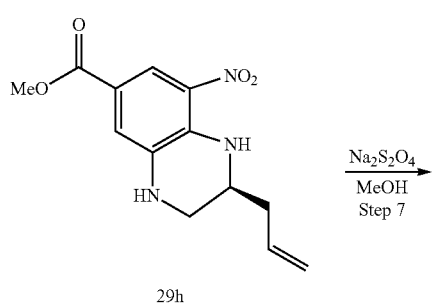

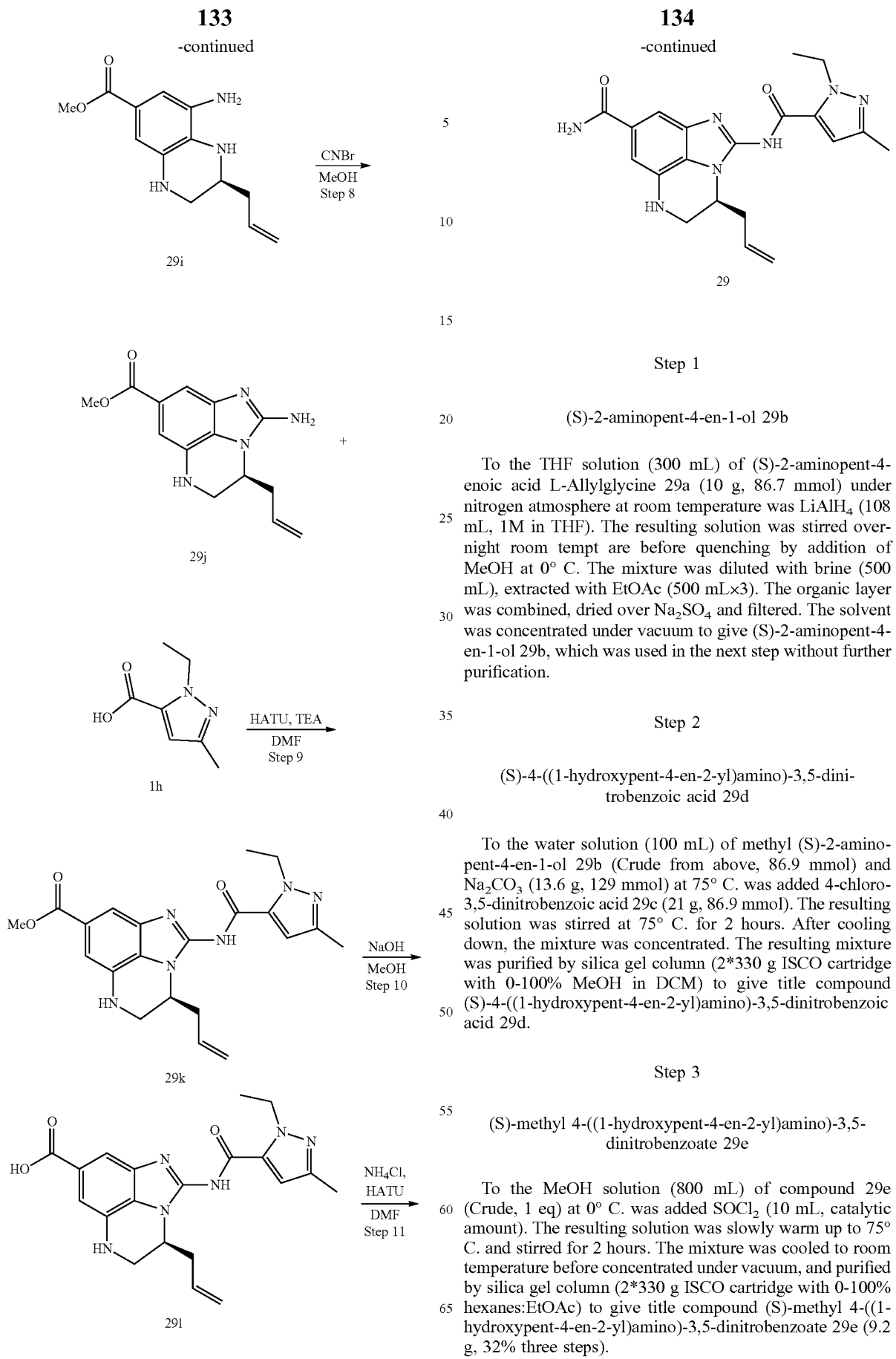

Step 1

(S)-2-aminopent-4-en-1-ol 29b

To the THF solution (300 mL) of (S)-2-aminopent-4-enoic acid L-Allylglycine 29a (10 g, 86.7 mmol) under nitrogen atmosphere at room temperature was LiAlH$_4$ (108 mL, 1M in THF). The resulting solution was stirred overnight room tempt are before quenching by addition of MeOH at 0° C. The mixture was diluted with brine (500 mL), extracted with EtOAc (500 mL×3). The organic layer was combined, dried over Na$_2$SO$_4$ and filtered. The solvent was concentrated under vacuum to give (S)-2-aminopent-4-en-1-ol 29b, which was used in the next step without further purification.

Step 2

(S)-4-((1-hydroxypent-4-en-2-yl)amino)-3,5-dinitrobenzoic acid 29d

To the water solution (100 mL) of methyl (S)-2-aminopent-4-en-1-ol 29b (Crude from above, 86.9 mmol) and Na$_2$CO$_3$ (13.6 g, 129 mmol) at 75° C. was added 4-chloro-3,5-dinitrobenzoic acid 29c (21 g, 86.9 mmol). The resulting solution was stirred at 75° C. for 2 hours. After cooling down, the mixture was concentrated. The resulting mixture was purified by silica gel column (2*330 g ISCO cartridge with 0-100% MeOH in DCM) to give title compound (S)-4-((1-hydroxypent-4-en-2-yl)amino)-3,5-dinitrobenzoic acid 29d.

Step 3

(S)-methyl 4-((1-hydroxypent-4-en-2-yl)amino)-3,5-dinitrobenzoate 29e

To the MeOH solution (800 mL) of compound 29e (Crude, 1 eq) at 0° C. was added SOCl$_2$ (10 mL, catalytic amount). The resulting solution was slowly warm up to 75° C. and stirred for 2 hours. The mixture was cooled to room temperature before concentrated under vacuum, and purified by silica gel column (2*330 g ISCO cartridge with 0-100% hexanes:EtOAc) to give title compound (S)-methyl 4-((1-hydroxypent-4-en-2-yl)amino)-3,5-dinitrobenzoate 29e (9.2 g, 32% three steps).

Step 4 of Examples 29 was Prepared with the Similar Procedures as Example 5

Step 5 and Step 6

(S)-methyl 2-allyl-8-nitro-1,2,3,4-tetrahydroquinoxaline-6-carboxylate 29h

To the MeCN solution (40 mL) of methyl (S)-3-amino-4-((1-hydroxypent-4-en-2-yl)amino)-5-nitrobenzoate 29f (1.2 g, 4.06 mmol) and PPh$_3$ (2.34 g, 8.95 mmol, 2.2 eq) under nitrogen atmosphere at room temperature was added CBr$_4$ (3 g, 8.95 mmol, 2.2 eq) in MeCN (10 mL). The resulting solution was stirred at room temperature for 15 min before addition of NEt$_3$ (1.7 mL, 17.8 mmol, 4.4 eq). After stirring 30 min at room temperature, the mixture was concentrated. The resulting mixture was purified by silica gel column (40 g ISCO cartridge with 0-100% with 0-100% EtOAc in Hexanes) to give title compound methyl (S)-2-allyl-8-nitro-1,2,3,4-tetrahydroquinoxaline-6-carboxylate 29h (872 mg, 77%).

Step 7-11 of Examples 29 was Prepared with the Similar Procedures as Example 5

In step 11, the mixture was purified by prep-HPLC, eluated with ACN/H$_2$O/TFA to give title compound (S)-4-allyl-2-(1-ethyl-3-methyl-1H-pyrazole-5-carboxamido)-5,6-dihydro-4H-imidazo[1,5,4-de]quinoxaline-8-carboxamide 29. MS m/z (ESI): 394 [M+1].

Example 30

(S)-4-allyl-2-(1-ethyl-3-methyl-1H-pyrazole-5-carboxamido)-6-(3-methoxypropyl)-5,6-dihydro-4H-imidazo[1,5,4-de]quinoxaline-8-carboxamide 30

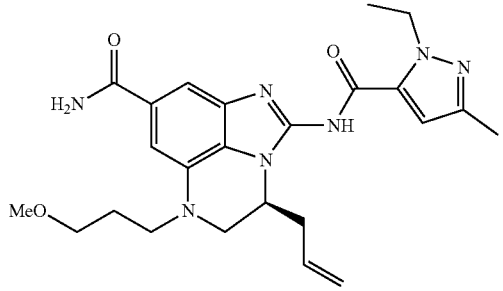

30

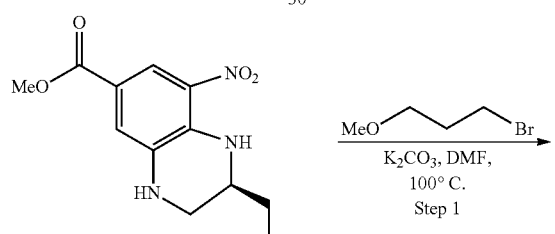

29h

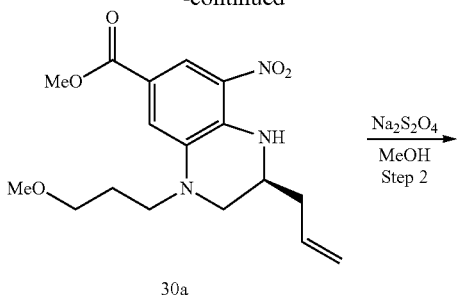

30a

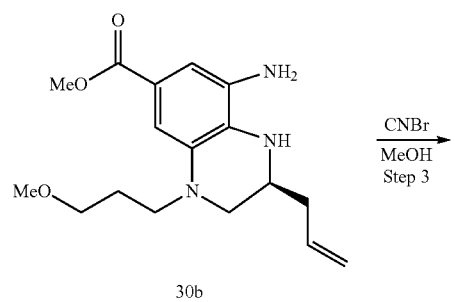

30b

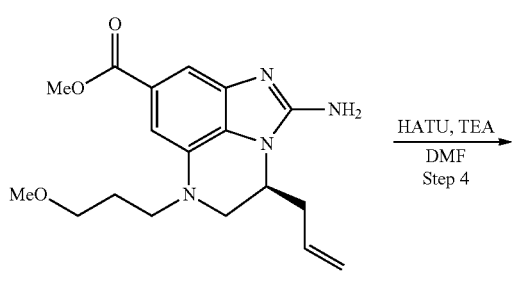

30c

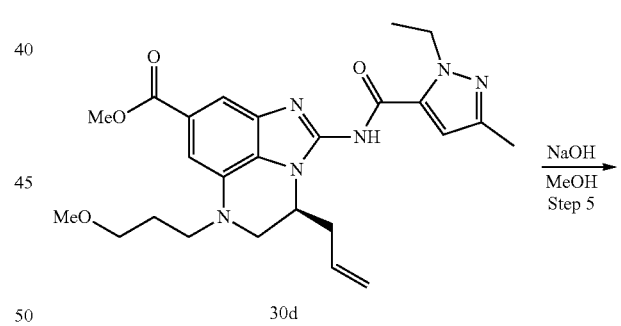

30d

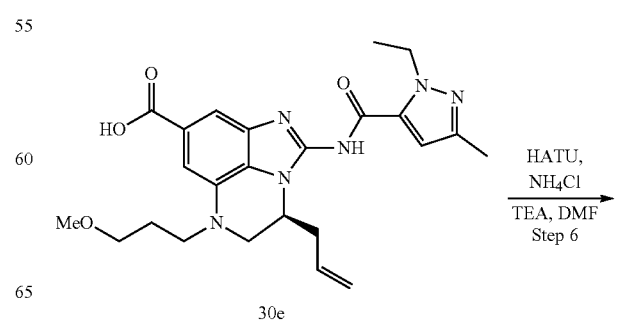

30e

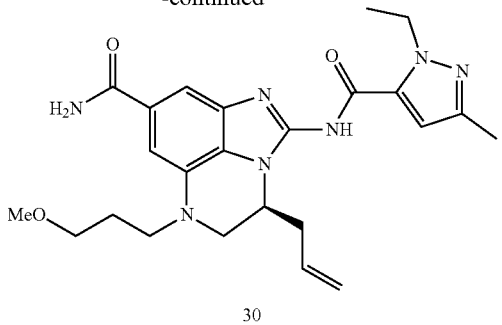

30

Step 1

(S)-methyl 2-allyl-4-(3-methoxypropyl)-8-nitro-1,2, 3,4-tetrahydroquinoxaline-6-carboxylate 30a To the DMF solution (5 mL) of methyl (S)-2-allyl-8-nitro-1,2,3,4-tetrahydroquinoxaline-6-carboxylate 29h (97 mg, 0.35 mmol) and K₂CO₃ (97 mg, 0.70 mmol, 2 eq) under nitrogen atmosphere at 100° C. was added 1-bromo-3-methoxypropane (2 mL). The resulting solution was stirred overnight at 100° C. The mixture was concentrated under vacuum and purified by silica gel column (20 g ISCO cartridge with 0-100% EtOAc in Hexanes) to give title compound (S)-2-allyl-4-(3-methoxypropyl)-8-nitro-1,2,3,4-tetrahydroquinoxaline-6-carboxylate 30a and its regioisomer (100 mg, 81%).

Step 2-6 of Examples 30 was Prepared with the Similar Procedures as Example 5

In step 6, the mixture was purified by prep-HPLC, eluated with MeCN/H₂O/formic acid to give title compound (S)-4-allyl-2-(1-ethyl-3-methyl-1H-pyrazole-5-carboxamido)-6-(3-methoxypropyl)-5,6-dihydro-4H-imidazo[1,5,4-de]quinoxaline-8-carboxamide 30. MS m/z (ESI): 466 [M+1]. ¹H NMR (400 MHz, MeOD): δ 7.25 (s, 1H), 7.04 (s, 1H), 6.59 (s, 1H), 5.96-5.86 (m, 1H), 5.04-5.00 (m, 2H), 4.66-4.64 (m, 2H), 3.78-3.35 (m, 6H), 3.25-3.23 (m, 1H), 3.22 (s, 3H), 2.56-2.18 (m, 2H), 2.15 (s, 3H), 1.86-1.83 (m, 2H), 1.29 (t, J=7.2 Hz, 3H).

Example 31

(S)-4-allyl-2-(1-ethyl-3-methyl-1H-pyrazole-5-carboxamido)-6-methyl-5,6-dihydro-4H-imidazo[1,5,4-de]quinoxaline-8-carboxamide 31

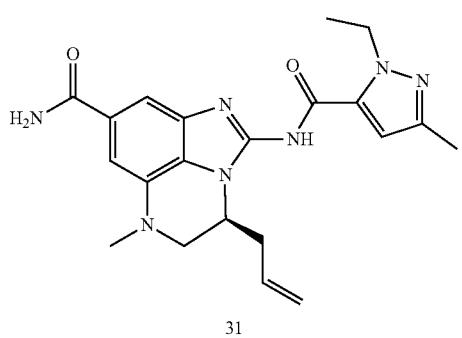

31

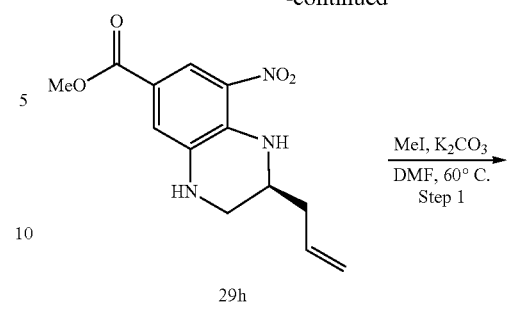

29h

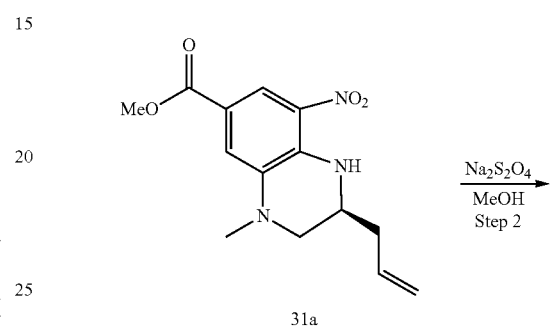

31a

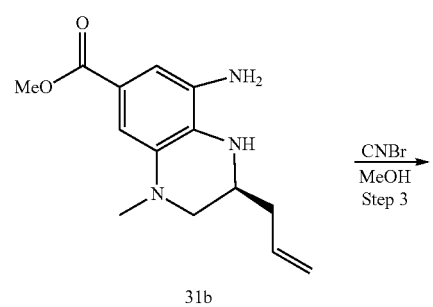

31b

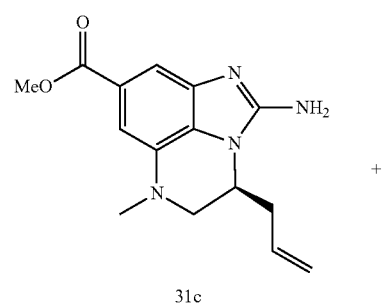

31c

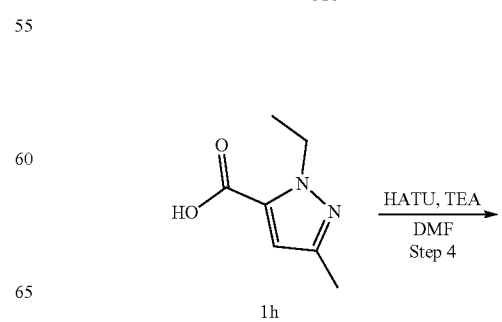

1h

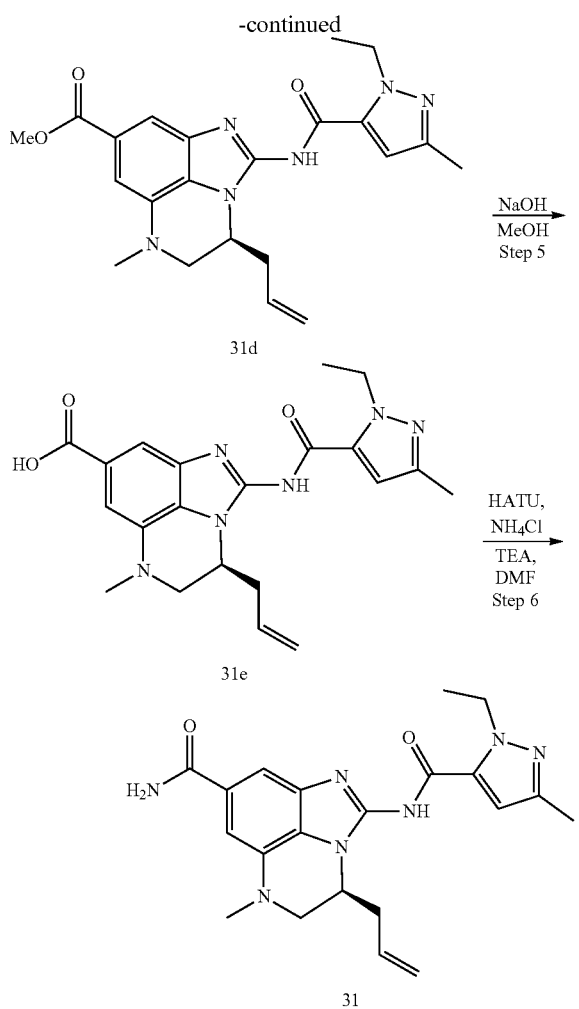

Step 1-6 of Examples 31 was Prepared with the Similar Procedures as Example 30

In step 6, the mixture was purified by prep-HPLC, eluated with ACN/H$_2$O/formic acid to give title compound (S)-4-allyl-2-(1-ethyl-3-methyl-1H-pyrazole-5-carboxamido)-6-methyl-5,6-dihydro-4H-imidazo[1,5,4-de]quinoxaline-8-carboxamide 31. MS m/z (ESI): 408 [M+1]. $^1$H NMR (400 MHz, MeOD): δ 7.42 (s, 1H), 7.12 (s, 1H), 6.71 (s, 1H), 6.05-5.96 (m, 1H), 5.15-5.12 (m, 2H), 4.76-4.68 (m, 3H), 3.56-3.37 (m, 1H), 3.36-3.33 (m, 1H), 3.33 (s, 3H), 2.70-2.61 (m, 2H), 2.27 (s, 3H), 1.45 (t, J=7.2 Hz, 3H).

Biological Assays

Test Example 1. Thermal Shift Assay for Measuring the Relative Binding Affinity to hSTING c-Terminal Domain Material and Reagents
1. SYPRO Orange Stain (Thermo Fisher Scientific)
2. Buffer—20 mM HEPES pH 7.2, 150 mM NaCl (Sigma)
3. DMSO (Thermo Fisher Scientific)
4. Purified hSTING (aa154-342)
5. Compounds—10 mM stock in DMSO
6. cGAMP—10 mM stock in DMSO (Sigma)
7. Light Cycler 480 II (Roche)
8. Light Cycler 480 Multi-well Plates, 384-well white (Roche)

Experimental Procedure

From each of the 10 mM stock solutions of compounds in DMSO, dilutions are made to create samples with three concentrations 10 mM, 5 mM and 2.5 mM. From these dilutions a final 50 fold dilution is made into assay buffer, giving concentrations of 200 μM, 100 μM, and 50 μM. From each of the buffer dilutions, 5 μL is added to the 384 well assay plate. A positive control is setup with cGAMP using the same dilution scheme as the ligands. A baseline thermal shift for the negative control is determined using buffer and 2% DMSO.

An aliquot of protein is thawed on ice and SYPRO orange reagent is brought to room temperature. The 5000× SYPRO orange stock is diluted in assay buffer to a concentration of 10×. Protein is diluted to a concentration of 10 μM in the prepared buffer/dye solution. Five micro-liters of protein/buffer/dye solution is added to each of the sample and control wells, and the plate is sealed with the provided films. The plate is centrifuged for 5 min at 20° C. at 1000 rpm.

On the Light Cycler instrument, measurements are made over a temperature gradient from 20° C. to 99° C. at 0.07° C./s and data acquisitions collected at a rate of 8/° C. is used to measure the change in fluorescence as a function of temperature. Data analysis is performed using the Roche Light Cycler Software to determine the melting temperature (Tm ° C.) of each sample. A mean Tm ° C. for the negative control is calculated and subtracted from each of the samples to generate the ΔTm ° C. values for each of the ligands.

The relative binding affinity to hSTING c-terminal domain of the compounds of the present invention was determined by the above assay, and ΔTm ° C. values are shown in the following table 1.

TABLE 1

Thermal Shift ΔTm ° C. values of the compounds in the present invention.

| Example No. | Thermal Shift ΔTm (° C.) at 100 μM |
| --- | --- |
| 1 | 5.7 |
| 2 | 1.1 |
| 3 | 0.7 |
| 4 | 4.6 |
| 5 | 2.9 |
| 6 | −0.5 |
| 7 | 5.4 |
| 8 | 7.5 |
| 9 | −0.1 |
| 11 | 5.5 |
| 13 | 10.7 |
| 14 | 4 |
| 15 | 3 |
| 16 | 1 |
| 17 | 2 |
| 20 | 13 |
| 21 | 13 |
| 23 | 11 |
| 24 | 12 |
| 25 | 13 |

Conclusion: The compounds of the present invention showed binding affinity to a human STING protein.

Test Example 2. Human THP1 Reporter Cell Assay

Materials and Reagents
1. Human THP1-Dual KI-hSTING-R232 Cells (InvivoGen, Cat. #thpd-r232)
2. QUANTI-LUC (InvivoGen, Cat. #rep-qlc2)
3. Media for cell culture and compound dilution: RPMI with high glucose and glutamine (Genesee, Cat. #25-506), 10% fetal bovine serum (Life Technologies, Cat. #10082147), 25 mM HEPES (Genesee, Cat. #25-534), 100 µg/ml Normocin (InvivoGen, Cat. #ant-nr-2), 10 µg/ml blasticidin (InvivoGen, Cat. #ant-bl-05), 100 µg/ml Zeocin (InvivoGen, Cat. #ant-zn-5p) and Penicillin-Streptomycin (100×) (Life Technologies, Cat. #15140122)
4. Infinite M1000 plate reader (TECAN)

Experimental Procedure

Activation of STING in THP1-Dual KI-hSTING-R232 cells was determined by measuring the luminescence signal resulting from the expression of the IRF luciferase reporter gene. All reagent preparation and assay procedures were conducted according to the protocols provided by InvivoGen. In brief, test compounds and cells ($1 \times 10^5$ cells per well) were dispensed into 96-well plates with a final volume per well of 150 µl. Plates were incubated in a humidified, 5% $CO_2$ incubator at 37° C. for 24 hours. The expression level of the reporter gene was measured by transferring 20 µl of the supernatant to a non-transparent 96-well plate to which 50 µl of QUANTI-LUC was dispensed into each well. The resulting luminescence signal was immediately read using a TECAN plate reader. The background luminescence signal from media was subtracted. The fold induction effect of the luminescence signal at each compound concentration was determined relative to controls that lack compound treatment. The plot of fold induction effect versus the log of compound concentration was fit in GraphPad Prism with a 4-parameter concentration response equation to calculate $EC_{50}$ and Emax.

Activation of STING in THP1 of the compounds in the present invention was determined by the above assay, and $EC_{50}$ values are shown in the following table 2.

TABLE 2

Human THP1 reporter cell assay

| Example No. | $EC_{50}$ (THP1 R232, µM) |
|---|---|
| 1 | 1.6 |
| 5 | 3 |
| 5-1 | >20 |
| 5-2 | 1.3 |
| 5-3 | 1.3 |
| 8 | 2.6 |
| 13 | 0.03 |
| 18 | 0.16 |
| 20 | 0.1 |
| 21 | 0.06 |
| 22 | 0.1 |
| 23 | 0.7 |
| 24 | 0.35 |
| 25 | 0.5 |
| 27 | >20 |
| 28 | >20 |
| 29 | 12 |
| 30 | 1.5 |
| 31 | 2.4 |

Conclusion: The compounds of the present invention had significant stimulatory activity on human STING.

Test Example 3. IFNβ Secretion in Human PBMC

Materials and Reagents
1. Human PBMC cells (STEMCELL Technologies)
2. Lymphocyte Medium (Zenbio)
3. Culture and compound dilution media: RPMI with high glucose and glutamine (Genesee, Cat. #25-506), 10% fetal bovine serum (Life Technologies, Cat. #10082147), 100 µg/ml Normocin (InvivoGen, Cat. #ant-nr-2) and Penicillin-Streptomycin (100×) (Life Technologies, Cat. #15140122)
4. Human IFNβ Quantikine ELISA kit (R&D systems)
5. Infinite M1000 plate reader (TECAN)

Experimental Procedure

Cryopreserved peripheral blood human mononuclear cells (PBMCs) were rapidly thawed and resuspended in Lymphocyte Media and centrifuged at 500×g for 5 minutes. The supernatant was removed and the cell pellets were gently resuspended in cell culture and compound dilution media. Human PBMC cells were plated in a 96-well format at a concentration of $1.5 \times 10^5$ cells per well. The test compounds, at varying concentrations, or vehicle control (<0.3% DMSO) were mixed with the cells giving a final volume of 150 µl per well. The plates were incubated for 5 hours in a humidified, 5% $CO_2$ incubator at 37° C. After incubation, the human IFNβ in the supernatant and the IFNβ standard controls were measured using human IFNβ Quantikine ELISA kit according to the manufacturer's protocol. The absorbance at 450 nm was measured with Infinite M1000 plate reader and corrected by background reading at 540 nm of each well. The amount of was calculated based on the standard curves. The plot of IFNβ concentration versus the log of compound concentration was fit in GraphPad Prism with a 4-parameter concentration response equation to calculate $EC_{50}$ and Emax.

TABLE 3

IFNβ secretion in human PBMC

| Example No | $EC_{50}$ (µM) |
|---|---|
| 1 | 1.1 |
| 5 | 2 |
| 5-2 | 1.9 |
| 5-3 | 1.5 |
| 11 | 17 |
| 13 | 0.1 |
| 14 | 1.8 |
| 15 | 19 |
| 18 | 0.3 |
| 19 | 0.7 |
| 22 | 0.34 |

Conclusion: The compounds of the present invention showed significant activity in STING-specific IFNβ generation.

The foregoing examples and description of the preferred embodiments should be taken as illustrating, rather than as limiting, the present invention as defined by the claims. Numerous variations and combinations of the features set forth above may be utilized without departing from the present invention as set forth in the claims. All literature and references cited are incorporated herein by reference in their entireties.

What is claimed is:

1. A compound of formula (I), or a tautomer, or a pharmaceutically acceptable salt thereof:

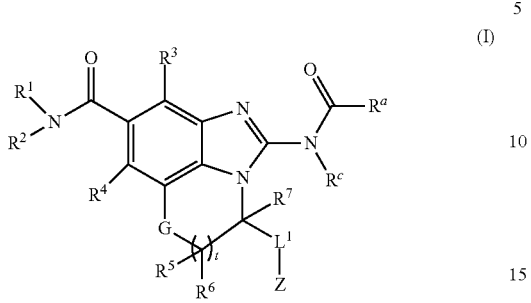

wherein:
- $R^a$ is selected from the group consisting of alkyl, alkenyl, alkynyl, haloalkyl, and hydroxyalkyl, wherein the alkyl, alkenyl or alkynyl is unsubstituted or substituted with one or more substituents independently selected from the group consisting of halogen, alkyl, alkoxy, haloalkyl, amino, nitro, cyano, hydroxy, hydroxyalkyl, carboxylic acid, cycloalkyl, heterocyclyl, aryl and heteroaryl;
- or $R^a$ is

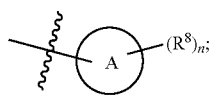

ring A is selected from the group consisting of cycloalkyl, heterocyclyl, aryl and heteroaryl;
- G is O;
- $R^c$ is selected from the group consisting of hydrogen, alkyl, haloalkyl, alkenyl and alkynyl;
- $R^1$ and $R^2$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, alkyl, alkoxy, haloalkyl, amino, nitro, cyano, hydroxy, hydroxyalkyl, cycloalkyl, heterocyclyl, aryl and heteroaryl;
- $R^3$ and $R^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;
- $R^5$, $R^6$ and $R^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;
- $L^1$ is selected from the group consisting of alkylene, alkenylene, NH, —$(CH_2)_sNH$—, —$(CH_2)_sNH(CH_2)_r$—, O, $S(O)_m$, C(O), —C(O)NH—, —NHC(O)— or —HNC(O)NH—, wherein the alkylene or alkenylene is unsubstituted or substituted with one or more substituents selected from the group consisting of halogen, alkyl, alkoxy, haloalkyl, amino, nitro, hydroxy, hydroxyalkyl, cyano, oxo, —C(O)OR$^{18}$, $R^{19}$, cycloalkyl, heterocyclyl, aryl and heteroaryl;
two substitutes on the same carbon can form a cycloalkyl or heterocyclyl ring; two substitutes on adjacent carbons can form a cycloalkyl, heterocyclyl, aryl and heteroaryl ring;
- or $L^1$ is absent;
- Z is selected from the group consisting of —C(O)O-benzyl, butyloxy carbonyl, hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, —$NR^9R^{10}$, oxo, —C(O)OR$^{18}$, $R^{19}$, cycloalkyl, heterocyclyl, aryl and heteroaryl;
- or Z is selected from a formula (Za) or a tautomer:

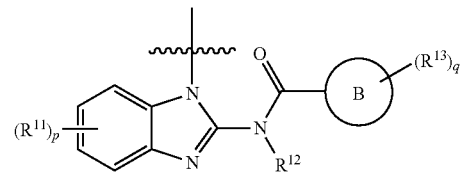

wherein, ring B is selected from the group consisting of cycloalkyl, heterocyclyl, aryl and heteroaryl;
- $R^8$ at each occurrence is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents independently selected from the group consisting of halogen, alkyl, alkoxy, haloalkyl, amino, nitro, hydroxy, hydroxyalkyl, cyano, cycloalkyl, heterocyclyl, aryl and heteroaryl;
- $R^9$ and $R^{10}$ are identical or different, and each is independently selected from the group consisting of hydrogen, alkyl, —C(O)O-benzyl, haloalkyl, cycloalkyl, heterocyclyl, aryl and heteroaryl;
- $R^{11}$ each is identical or different, and each is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl; wherein the alkyl or alkoxy is unsubstituted or substituted with one or more substituents selected from the group consisting of halogen, alkyl, alkoxy, alkenyl, alkynyl, haloalkyl, amino, nitro, hydroxy, hydroxyalkyl, cyano, —O—P(O)(OH)$_2$, cycloalkyl, heterocyclyl and NR$^{16}$R$^{17}$;
- $R^{12}$ is selected from the group consisting of hydrogen, alkyl, alkenyl and alkynyl;
- $R^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^{14}$ and $R^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, hydroxy, cyano, nitro, alkyl, alkoxy, cycloalkyl, heterocyclyl, aryl and heteroaryl;

$R^{16}$ and $R^{17}$ are identical or different, and each is independently selected from hydrogen or alkyl;

or, $R^{16}$ and $R^{17}$ together with the nitrogen atom to which they are attached form a heterocyclyl, wherein the heterocyclyl contains one or two identical or different heteroatoms selected from the group consisting of N, O and S, and the heterocyclyl is optionally substituted by one or more substituents selected from the group consisting of alkyl, alkoxy, halogen, amino, cyano, nitro, hydroxy and hydroxyalkyl;

$R^{18}$ is hydrogen or alkyl;

$R^{19}$ is cycloalkyl, heterocyclyl, aryl or heteroaryl, wherein the cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl and cyano;

n is 0, 1, 2, 3 or 4;

m is 0, 1 or 2;

s is integer of 1 to 6;

r is 1, 2, 3 or 4;

t is 1;

p is 0, 1, 2, 3 or 4; and q is 0, 1, 2, 3 or 4.

2. The compound of formula (I) according to claim 1, being a compound of formula (II):

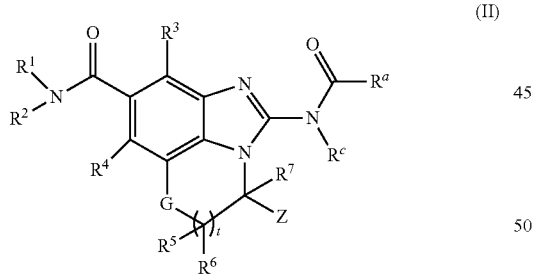

(II)

or a tautomer, or a pharmaceutically acceptable salt thereof, wherein:

Z is selected from the group consisting of hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, oxo, —C(O) OR$^{18}$, R$^{19}$, —NHC(O)O— benzyl, cycloalkyl, heterocyclyl, aryl and heteroaryl; and G, $R^{18}$, $R^{19}$, t, $R^a$, $R^c$, $R^1$, $R^2$, $R^3$, $R^4$, $R^5$, $R^6$, and $R^7$ are each as defined in claim 1.

3. The compound of formula (I) according to claim 1, being a compound of formula (III):

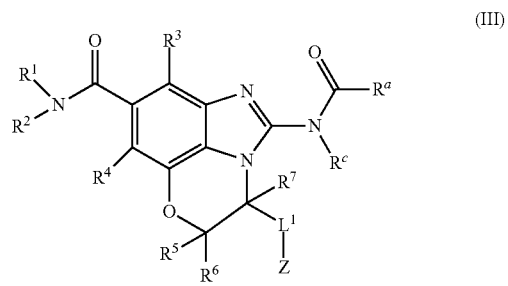

(III)

or a tautomer, or a pharmaceutically acceptable salt thereof, wherein:

$R^a$ is selected from the group consisting of alkyl, alkenyl, alkynyl, haloalkyl, and hydroxyalkyl, wherein the alkyl, alkenyl or alkynyl is unsubstituted or substituted with one or more substituents selected from the group consisting of halogen, alkyl, alkoxy, haloalkyl, amino, nitro, cyano, hydroxy, hydroxyalkyl, carboxylic acid, cycloalkyl, heterocyclyl, aryl and heteroaryl;

or $R^a$ is

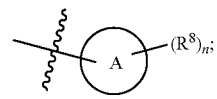

ring A is selected from the group consisting of cycloalkyl, heterocyclyl, aryl and heteroaryl;

$R^c$ is selected from the group consisting of hydrogen, alkyl, haloalkyl, alkenyl and alkynyl;

$R^1$ and $R^2$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, alkyl, alkoxy, haloalkyl, amino, nitro, cyano, hydroxy, hydroxyalkyl, cycloalkyl, heterocyclyl, aryl and heteroaryl;

$R^3$ and $R^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$R^5$, $R^6$ and $R^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$L^1$ is selected from the group consisting of alkylene, alkenylene, NH, —(CH$_2$)$_s$NH—, O, S(O)$_m$, C(O), —C(O)NH—, —NHC(O)— or —HNC(O)NH—, wherein the alkylene or alkenylene is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;

two substitutes on the same carbon can form a cycloalkyl or heterocyclyl ring; two substitutes on adjacent carbons can form a cycloalkyl, heterocyclyl, aryl and heteroaryl ring;

or $L^1$ is absent;

Z is selected from the group consisting of —C(O)O-benzyl, butyloxy carbonyl, hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, —$NR^9R^{10}$, cycloalkyl, heterocyclyl, aryl and heteroaryl;

or Z is selected from a formula (Za) or a tautomer:

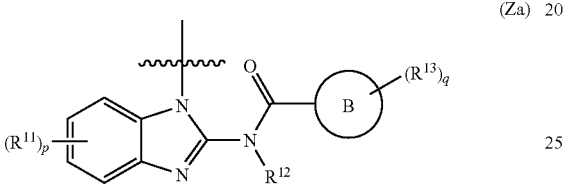

(Za)

wherein, ring B is selected from the group consisting of cycloalkyl, heterocyclyl, aryl and heteroaryl;

$R^8$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^9$ and $R^{10}$ are identical or different, and each is independently selected from the group consisting of hydrogen, alkyl, —C(O)O-benzyl, haloalkyl, cycloalkyl, heterocyclyl, aryl and heteroaryl;

$R^{11}$ each is identical or different, and each is independently selected from the group consisting of hydrogen, halogen, alkyl, alkoxy, haloalkyl, amino, nitro, hydroxy, hydroxyalkyl, cyano, —C(O)$NR^{14}R^{15}$, cycloalkyl, heterocyclyl, aryl and heteroaryl;

$R^{12}$ is selected from the group consisting of hydrogen, alkyl, alkenyl and alkynyl;

$R^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^{14}$ and $R^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, hydroxy, cyano, nitro, alkyl, alkoxy, cycloalkyl, heterocyclyl, aryl and heteroaryl;

n is 0, 1, 2, 3 or 4;

m is 0, 1 or 2;

s is integer of 1 to 6;

p is 0, 1, 2, 3 or 4; and q is 0, 1, 2, 3 or 4.

4. The compound of formula (I) according to claim 1, being a compound of formula (IV):

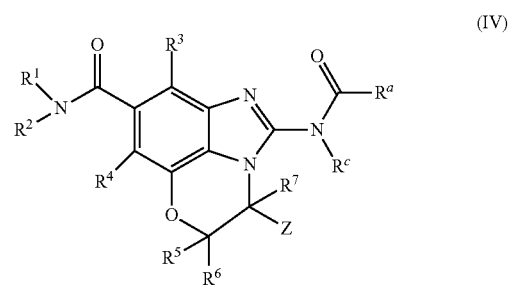

(IV)

or a tautomer, or a pharmaceutically acceptable salt thereof, wherein:

Z is selected from the group consisting of hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, —NHC(O)O-benzyl, cycloalkyl, heterocyclyl, aryl and heteroaryl; and $R^a$, $R^c$, $R^1$, $R^2$, $R^3$, $R^4$, $R^5$, $R^6$, and $R^7$ are each as defined in claim 1.

5. The compound of formula (I), or a tautomer, or a pharmaceutically acceptable salt thereof, according to claim 1, wherein $R^a$ is alkyl, wherein the alkyl is unsubstituted or substituted with one or more carboxylic acid (—$CO_2H$) groups;

or $R^a$ is

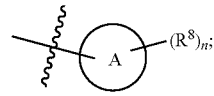

and ring A, $R^8$, and n are each as defined in claim 1.

6. The compound of formula (I) according to claim 1, being a compound of formula (V):

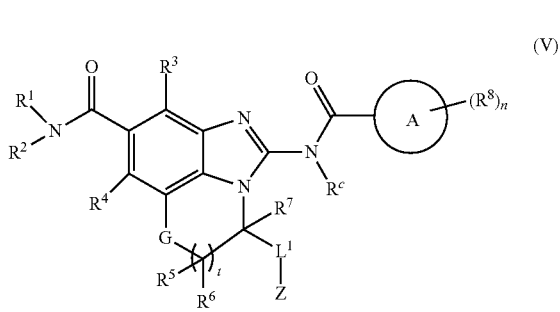

(V)

or a tautomer, or a pharmaceutically acceptable salt thereof, wherein:

G, t, ring A, $R^c$, $R^1$, $R^2$, $R^3$, $R^4$, $R^5$, $R^6$, $R^7$, $R^8$, $L^1$, Z, and n are each as defined in claim 1.

7. The compound of formula (I) according to claim 1, being a compound of formula (VI):

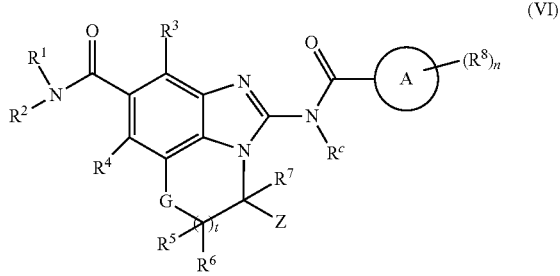

(VI)

or a tautomer, or a pharmaceutically acceptable salt thereof, wherein:

Z is selected from the group consisting of hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, oxo, —C(O)OR$^{18}$, R$^{19}$, —NHC(O)O— benzyl, cycloalkyl, heterocyclyl, aryl and heteroaryl; and G, R$^{18}$, R$^{19}$, t, ring A, R$^c$, R$^1$, R$^2$, R$^3$, R$^4$, R$^5$, R$^6$, R$^7$, R$^8$, and n are each as defined in claim 1.

8. The compound of formula (I) according to claim 2, being a compound of formula (VIII):

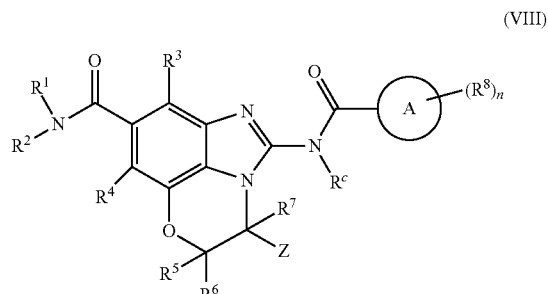

(VIII)

or a tautomer, or a pharmaceutically acceptable salt thereof, wherein:

Z is selected from the group consisting of hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, —NHC(O)O-benzyl, cycloalkyl, heterocyclyl, aryl and heteroaryl; and ring A, R$^c$, R$^1$, R$^2$, R$^3$, R$^4$, R$^5$, R$^6$, R$^7$, R$^8$, and n are each as defined in claim 2.

9. The compound of formula (I), or a tautomer, or a pharmaceutically acceptable salt thereof, according to claim 1, wherein R$^7$ is selected from the group consisting of hydrogen and alkyl.

10. The compound of formula (I), or a tautomer, or a pharmaceutically acceptable salt thereof, according to claim 1, wherein Z is selected from the group consisting of hydrogen, alkyl and alkenyl, wherein the alkyl is unsubstituted or substituted with one or more substituents selected from the group consisting of halogen, hydroxyl and —NHC(O)O-benzyl.

11. The compound of formula (I), or a tautomer, or a pharmaceutically acceptable salt thereof, according to claim 1, wherein R$^{11}$ is selected from the group consisting of hydrogen, alkoxy and —C(O)NR$^{14}$R$^{15}$; wherein the alkoxy is unsubstituted or substituted with one or more substituents selected from the group consisting of alkoxy, alkenyl, amino, hydroxy, hydroxyalkyl, cyano, —O—P(O)(OH)$_2$, cycloalkyl, heterocyclyl and NR$^{16}$R$^{17}$;

R$^{14}$ and R$^{15}$ are identical or different, and each is independently selected from hydrogen or alkyl;

R$^{16}$ and R$^{17}$ are identical or different, and each is independently selected from hydrogen or alkyl;

or, R$^{16}$ and R$^{17}$ together with the nitrogen atom to which they are attached form a heterocyclyl, wherein the heterocyclyl contains one or two identical or different heteroatoms selected from the group consisting of N, O and S.

12. The compound of formula (I) of claim 1, being a compound of formula (IX):

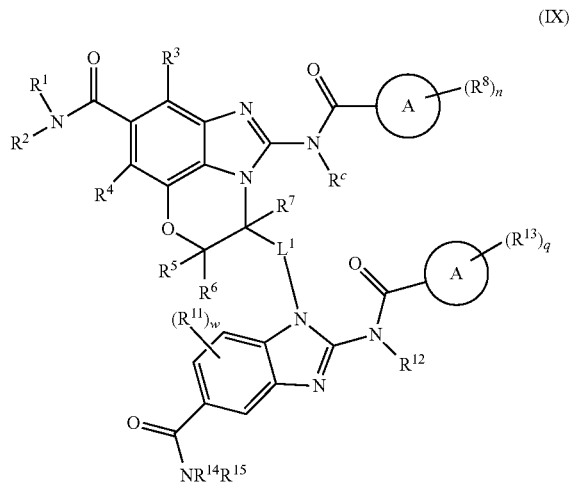

or a tautomer, or a pharmaceutically acceptable salt thereof,
wherein:
- $L^1$ is selected from the group consisting of —(CH$_2$)$_s$NH(CH$_2$)$_r$—, alkylene and alkenylene, wherein the alkylene or alkenylene is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl; two substitutes on the same carbon can form a cycloalkyl or heterocyclyl ring; two substitutes on adjacent carbons can form a cycloalkyl, heterocyclyl, aryl and heteroaryl ring;
- $R^{11}$ each is identical or different, and each is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl;
- $R^{14}$ and $R^{15}$ are identical or different, and each is independently selected from the group consisting of hydrogen and alkyl;
- w is 0, 1, 2 or 3; and
- ring A, ring B, $R^c$, $R^1$, $R^2$, $R^3$, $R^4$, $R^5$, $R^6$, $R^8$, $R^{12}$, $R^{13}$, r, s, n and q are each as defined in claim 1.

13. The compound of formula (I), or a tautomer, or a pharmaceutically acceptable salt thereof, according to claim 1, wherein $L^1$ is selected from the group consisting of alkylene and alkenylene, wherein the alkylene or alkenylene is unsubstituted or substituted with one or more substituents selected from the group consisting of oxo, —C(O)OR$^{18}$, $R^{19}$, halogen and hydroxy; and $R^{18}$ is hydrogen or alkyl; $R^{19}$ is heteroaryl unsubstituted or substituted with one or more substituents selected from alkyl or alkoxy.

14. The compound of formula (I), or a tautomer, or a pharmaceutically acceptable salt thereof, according to claim 1, wherein ring A is selected from the group consisting of heteroaryl and aryl.

15. The compound of formula (I), or a tautomer, or a pharmaceutically acceptable salt thereof, according to claim 1, wherein ring B is selected from the group consisting of heteroaryl and aryl.

16. The compound of formula (I), or a tautomer, or a pharmaceutically acceptable salt thereof, according to claim 1, wherein $R^c$ is selected from the group consisting of hydrogen and alkyl.

17. The compound of formula (I), or a tautomer, or a pharmaceutically acceptable salt thereof, according to claim 1, wherein $R^1$ and $R^2$ are identical or different, and each is independently selected from the group consisting of hydrogen and alkyl; wherein the alkyl is unsubstituted or substituted with one or more hydroxy.

18. The compound of formula (I), or a tautomer, or a pharmaceutically acceptable salt thereof, according to claim 1, wherein $R^3$, $R^4$, $R^5$ or $R^6$ are identical or different, and each is independently hydrogen.

19. The compound of formula (I), or a tautomer, or a pharmaceutically acceptable salt thereof, according to claim 1, wherein $R^8$ at each occurrence is independently selected from the group consisting of hydrogen and alkyl.

20. The compound of formula (I), or a tautomer, or a pharmaceutically acceptable salt thereof, according to claim 1, wherein the compound is selected from the group consisting of:

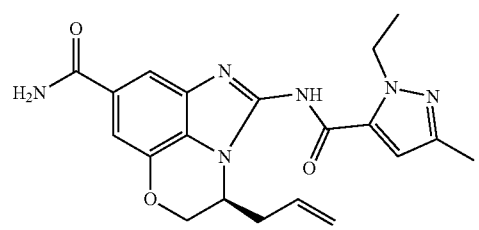

1

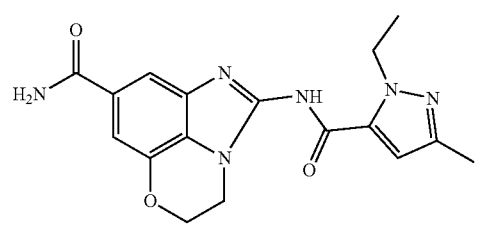

2

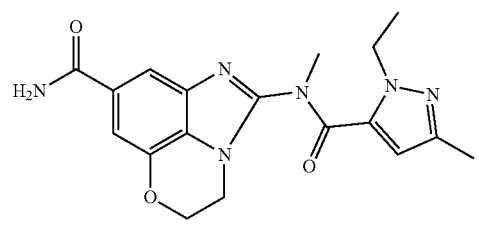

3

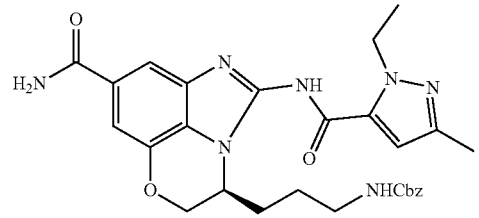

4

153
-continued
5
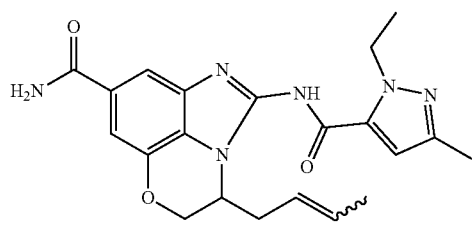
5-1
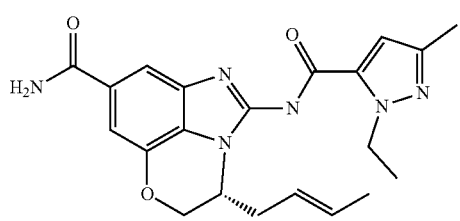
5-2
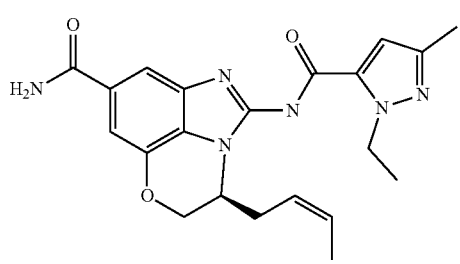
5-3
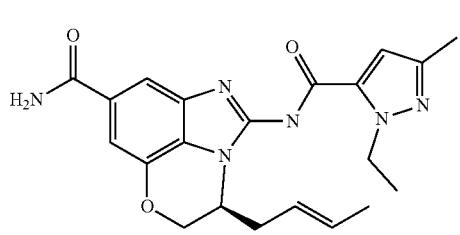
6
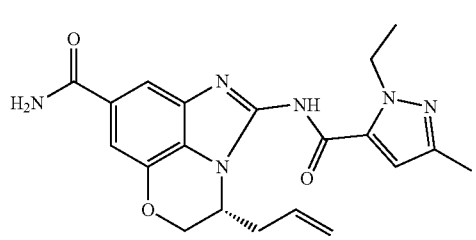
7
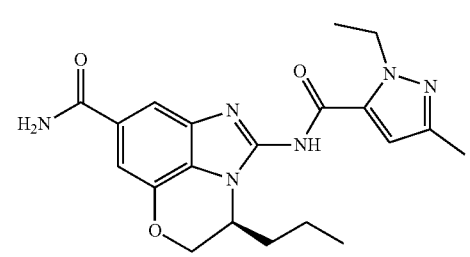
8
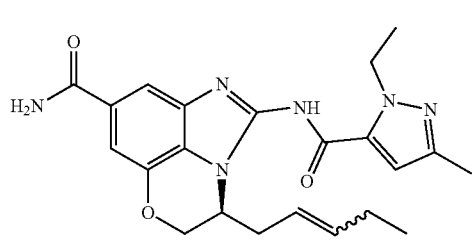
154
-continued
9
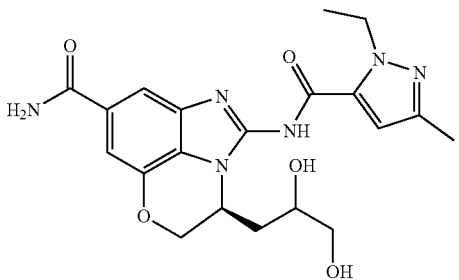
10
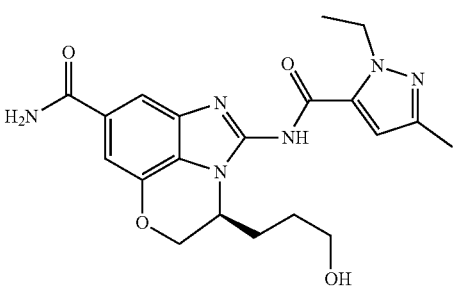
11
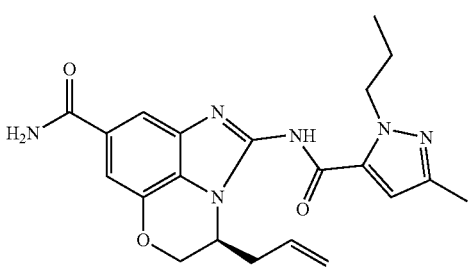
12
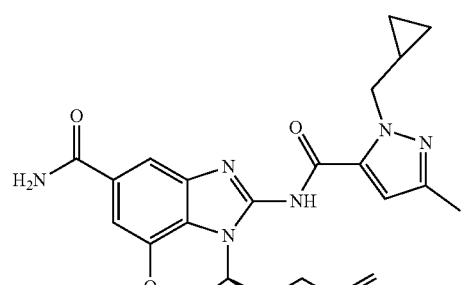
13
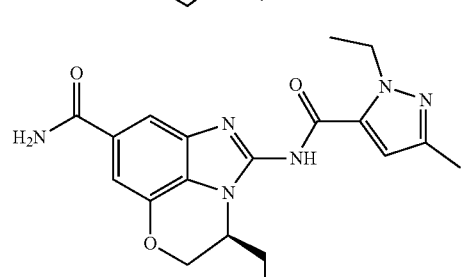
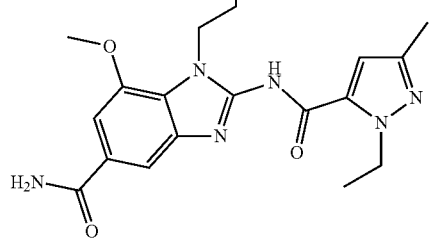

14
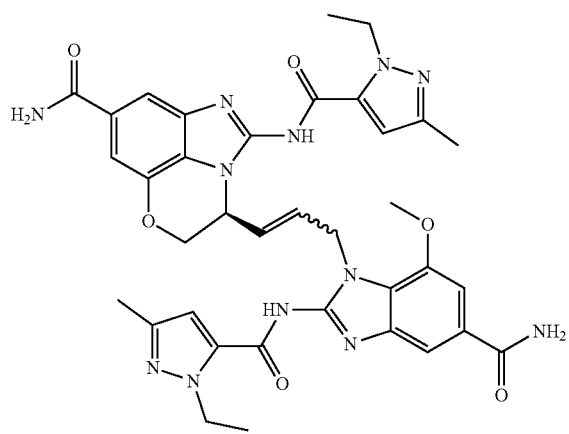
15
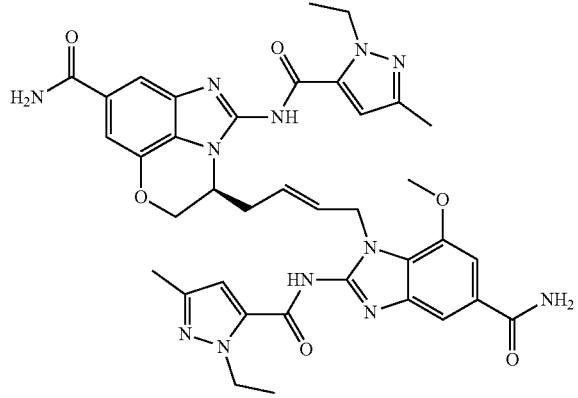
16
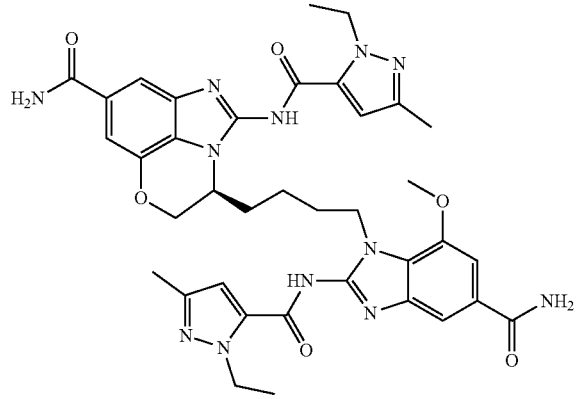
17
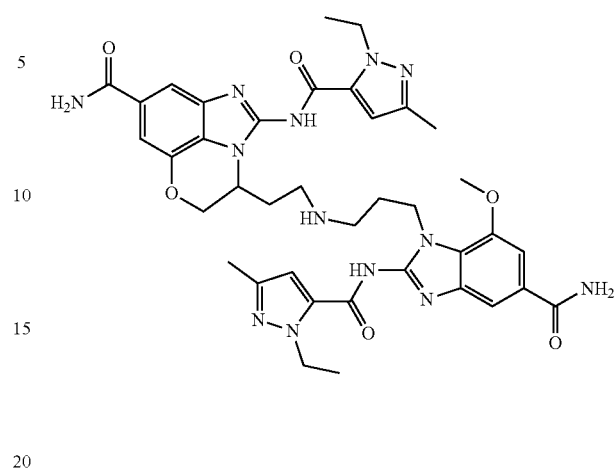
18
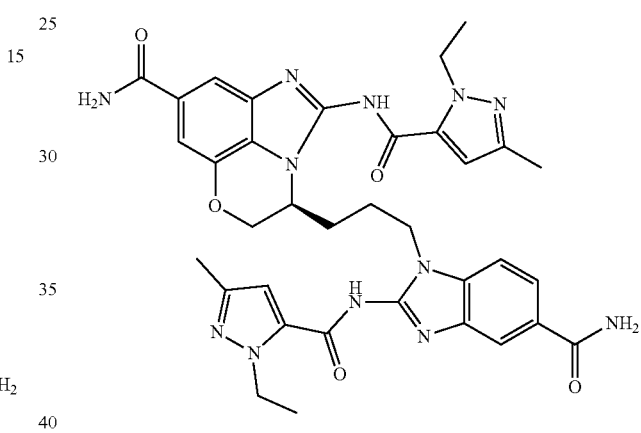
19
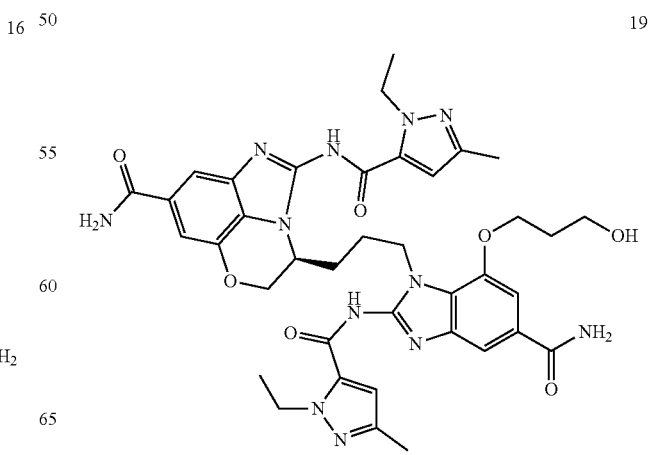

20
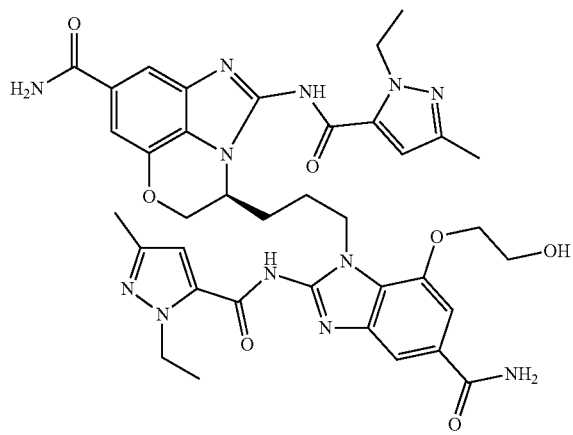
21
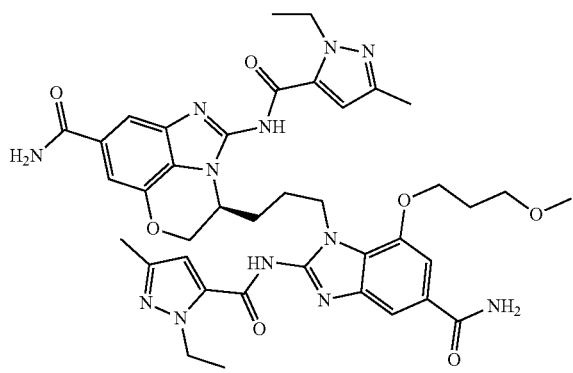
22
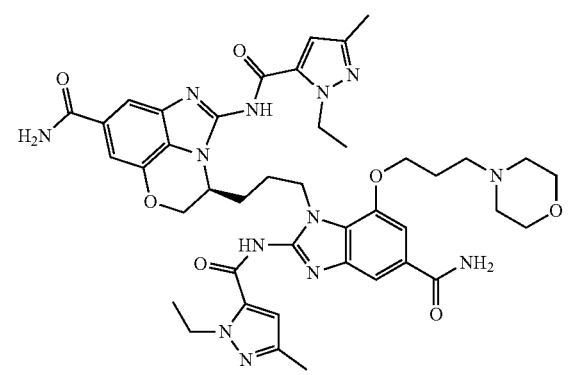
23
24
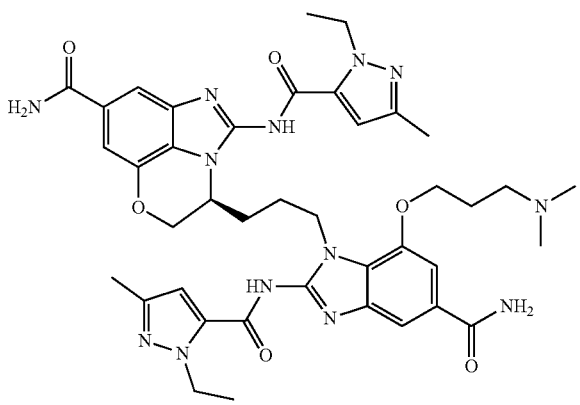
25
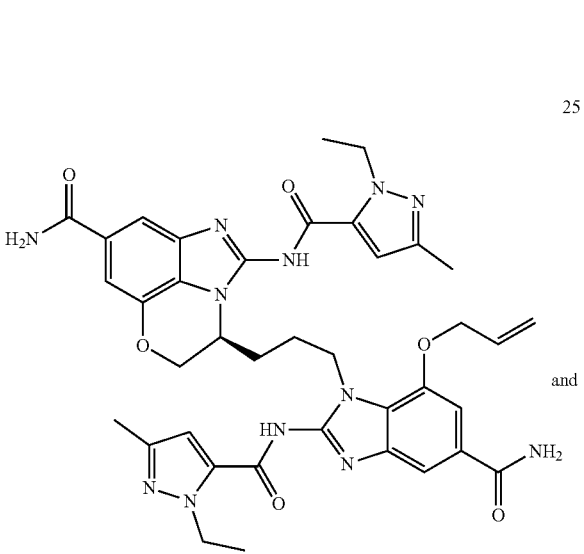
and
28
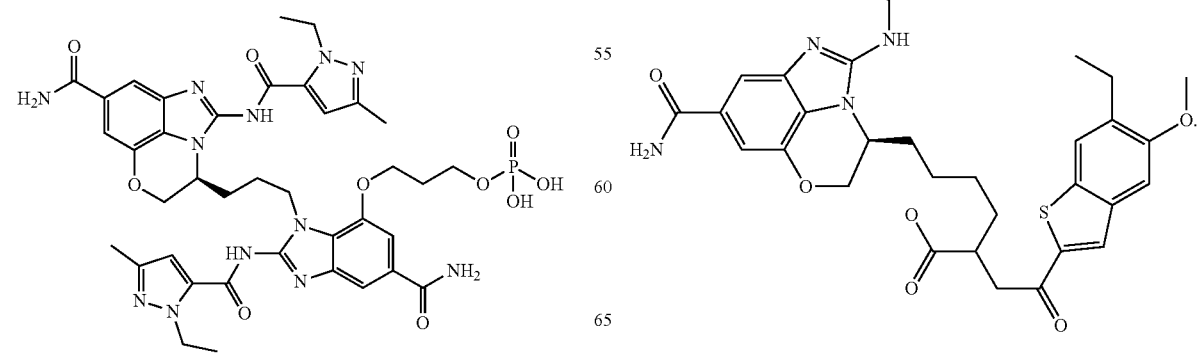

21. A compound of formula (IA), or a tautomer, or a pharmaceutically acceptable salt thereof:

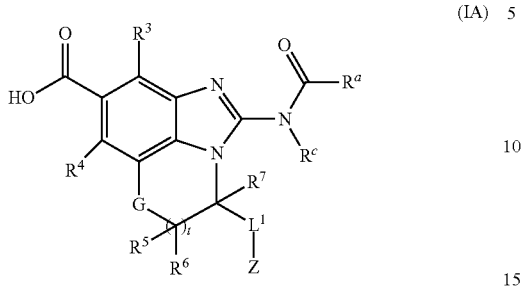

wherein:
R$^a$ is selected from the group consisting of alkyl, alkenyl, alkynyl, haloalkyl, hydroxyalkyl, wherein the alkyl, alkenyl or alkynyl is unsubstituted or substituted with one or more substituents selected from the group consisting of halogen, alkyl, alkoxy, haloalkyl, amino, nitro, cyano, hydroxy, hydroxyalkyl, carboxylic acid, cycloalkyl, heterocyclyl, aryl and heteroaryl;
or R$^a$ is

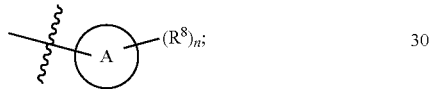

ring A is selected from the group consisting of cycloalkyl, heterocyclyl, aryl and heteroaryl;
G is O;
R$^c$ is selected from the group consisting of hydrogen, alkyl, haloalkyl, alkenyl and alkynyl;
R$^3$ and R$^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;
R$^5$, R$^6$ and R$^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;
L$^1$ is selected from the group consisting of alkylene, alkenylene, NH, —(CH$_2$)$_s$NH—, —(CH$_2$)$_s$NH (CH$_2$)$_r$—, O, S(O)$_m$, C(O), —C(O)NH—, —NHC (O)— or —HNC(O)NH—, wherein the alkylene or alkenylene is unsubstituted or substituted with one or more substituents selected from the group consisting of halogen, alkyl, alkoxy, haloalkyl, amino, nitro, hydroxy, hydroxyalkyl, cyano, oxo, —C(O)OR$^{18}$, R$^{19}$, cycloalkyl, heterocyclyl, aryl and heteroaryl; two substitutes on the same carbon can form a cycloalkyl or heterocyclyl ring; two substitutes on adjacent carbons can form a cycloalkyl, heterocyclyl, aryl and heteroaryl ring;
or L$^1$ is absent;
Z is selected from the group consisting of —C(O)O-benzyl, butyloxy carbonyl, hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, —NR$^9$R$^{10}$, oxo, —C(O)OR$^{18}$, R$^{19}$, cycloalkyl, heterocyclyl, aryl and heteroaryl;
or Z is selected from a formula (Za) or a tautomer:

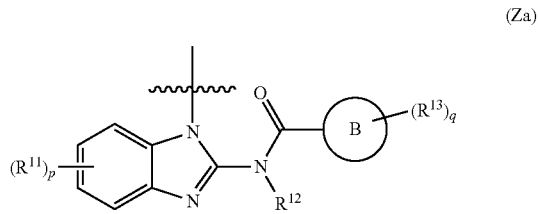

wherein, ring B is selected from the group consisting of cycloalkyl, heterocyclyl, aryl and heteroaryl;
R$^8$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;
R$^9$ and R$^{10}$ are identical or different, and each is independently selected from the group consisting of hydrogen, alkyl, —C(O)O-benzyl, haloalkyl, cycloalkyl, heterocyclyl, aryl and heteroaryl;
R$^{11}$ each is identical or different, and each is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl; wherein the alkyl or alkoxy is unsubstituted or substituted with one or more substituents selected from the group consisting of halogen, alkyl, alkoxy, alkenyl, alkynyl, haloalkyl, amino, nitro, hydroxy, hydroxyalkyl, cyano, —O—P(O)(OH)$_2$, cycloalkyl, heterocyclyl and NR$^{16}$R$^{17}$;
R$^{12}$ is selected from the group consisting of hydrogen, alkyl, alkenyl and alkynyl;
R$^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;
R$^{14}$ and R$^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, hydroxy, cyano, nitro, alkyl, alkoxy, cycloalkyl, heterocyclyl, aryl and heteroaryl;

$R^{16}$ and $R^{17}$ are identical or different, and each is independently selected from hydrogen or alkyl;

or, $R^{16}$ and $R^{17}$ together with the nitrogen atom to which they are attached form a heterocyclyl, wherein the heterocyclyl contains one or two identical or different heteroatoms selected from the group consisting of N, O and S, and the heterocyclyl is optionally substituted by one or more substituents selected from the group consisting of alkyl, alkoxy, halogen, amino, cyano, nitro, hydroxy and hydroxyalkyl;

$R^{18}$ is hydrogen or alkyl;

$R^{19}$ is cycloalkyl, heterocyclyl, aryl or heteroaryl, wherein the cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl and cyano;

n is 0, 1, 2, 3 or 4;

m is 0, 1 or 2;

s is integer of 1 to 6;

r is 1, 2, 3 or 4;

t is 1;

p is 0, 1, 2, 3 or 4; and q is 0, 1, 2, 3 or 4.

22. A compound of formula (IB), or a tautomer, or a pharmaceutically acceptable salt thereof:

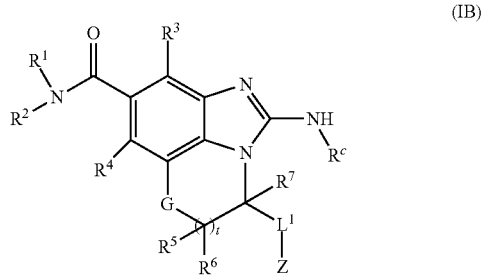

(IB)

wherein:

G is O;

$R^c$ is selected from the group consisting of hydrogen, alkyl, haloalkyl, alkenyl and alkynyl;

$R^1$ and $R^2$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, alkyl, alkoxy, haloalkyl, amino, nitro, cyano, hydroxy, hydroxyalkyl, cycloalkyl, heterocyclyl, aryl and heteroaryl;

$R^3$ and $R^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$R^5$, $R^6$ and $R^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$L^1$ is selected from the group consisting of alkylene, alkenylene, NH, —$(CH_2)_s$NH—, —$(CH_2)_s$NH$(CH_2)_r$—, O, S(O)$_m$, C(O), —C(O)NH—, —NHC(O)— or —HNC(O)NH—, wherein the alkylene or alkenylene is unsubstituted or substituted with one or more substituents selected from the group consisting of halogen, alkyl, alkoxy, haloalkyl, amino, nitro, hydroxy, hydroxyalkyl, cyano, oxo, —C(O)OR$^{18}$, $R^{19}$, cycloalkyl, heterocyclyl, aryl and heteroaryl; two substitutes on the same carbon can form a cycloalkyl or heterocyclyl ring; two substitutes on adjacent carbons can form a cycloalkyl, heterocyclyl, aryl and heteroaryl ring;

or $L^1$ is absent;

Z is selected from the group consisting of —C(O)O-benzyl, butyloxy carbonyl, hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, —NR$^9$R$^{10}$, oxo, —C(O)OR$^{18}$, R$^{19}$, cycloalkyl, heterocyclyl, aryl and heteroaryl;

or Z is selected from a formula (Za) or a tautomer:

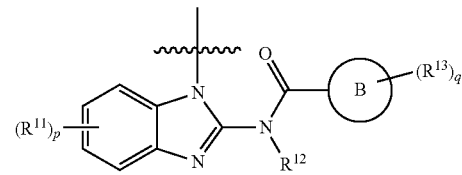

(Za)

wherein, ring B is selected from the group consisting of cycloalkyl, heterocyclyl, aryl and heteroaryl;

$R^9$ and $R^{10}$ are identical or different, and each is independently selected from the group consisting of hydrogen, alkyl, —C(O)O-benzyl, haloalkyl, cycloalkyl, heterocyclyl, aryl and heteroaryl;

$R^{11}$ each is identical or different, and each is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl; wherein the alkyl or alkoxy is unsubstituted or substituted with one or more substituents selected from the group consisting of halogen, alkyl, alkoxy, alkenyl, alkynyl, haloalkyl, amino, nitro, hydroxy, hydroxyalkyl, cyano, —O—P(O)(OH)$_2$, cycloalkyl, heterocyclyl and NR$^{16}$R$^{17}$;

$R^{12}$ is selected from the group consisting of hydrogen, alkyl, alkenyl and alkynyl;

$R^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^{14}$ and $R^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, hydroxy, cyano, nitro, alkyl, alkoxy, cycloalkyl, heterocyclyl, aryl and heteroaryl;

$R^{16}$ and $R^{17}$ are identical or different, and each is independently selected from hydrogen or alkyl;

or, $R^{16}$ and $R^{17}$ together with the nitrogen atom to which they are attached form a heterocyclyl, wherein the heterocyclyl contains one or two identical or different heteroatoms selected from the group consisting of N, O and S, and the heterocyclyl is optionally substituted by one or more substituents selected from the group consisting of alkyl, alkoxy, halogen, amino, cyano, nitro, hydroxy and hydroxyalkyl;

$R^{18}$ is hydrogen or alkyl;

$R^{19}$ is cycloalkyl, heterocyclyl, aryl or heteroaryl, wherein the cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl and cyano;

m is 0, 1 or 2;

s is integer of 1 to 6;

r is 1, 2, 3 or 4;

t is 1;

p is 0, 1, 2, 3 or 4; and q is 0, 1, 2, 3 or 4.

23. A compound of formula (IIIA), or a tautomer, or a pharmaceutically acceptable salt thereof:

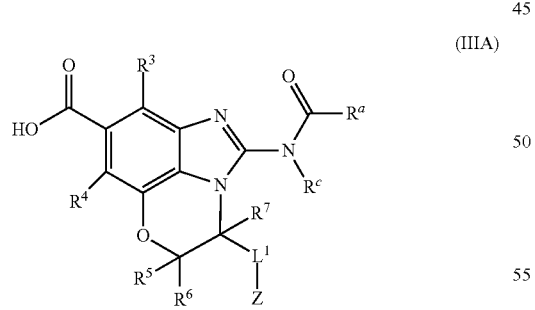

(IIIA)

wherein:

$R^a$ is selected from the group consisting of alkyl, alkenyl, alkynyl, haloalkyl, hydroxyalkyl, wherein the alkyl, alkenyl or alkynyl is unsubstituted or substituted with one or more substituents selected from the group consisting of halogen, alkyl, alkoxy, haloalkyl, amino, nitro, cyano, hydroxy, hydroxyalkyl, carboxylic acid, cycloalkyl, heterocyclyl, aryl and heteroaryl;

or $R^a$ is

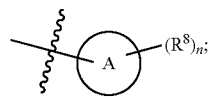

ring A is selected from the group consisting of cycloalkyl, heterocyclyl, aryl and heteroaryl;

$R^c$ is selected from the group consisting of hydrogen, alkyl, haloalkyl, alkenyl and alkynyl;

$R^3$ and $R^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$R^5$, $R^6$ and $R^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$L^1$ is selected from the group consisting of alkylene, alkenylene, NH, —$(CH_2)_s$NH—, O, $S(O)_m$, C(O), —C(O)NH—, —NHC(O)— or —HNC(O)NH—, wherein the alkylene or alkenylene is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl; two substitutes on the same carbon can form a cycloalkyl or heterocyclyl ring; two substitutes on adjacent carbons can form a cycloalkyl, heterocyclyl, aryl and heteroaryl ring;

or $L^1$ is absent;

Z is selected from the group consisting of —C(O)O-benzyl, butyloxy carbonyl, hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkenyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, —$NR^9R^{10}$, cycloalkyl, heterocyclyl, aryl and heteroaryl;

or Z is selected from a formula (Za) or a tautomer:

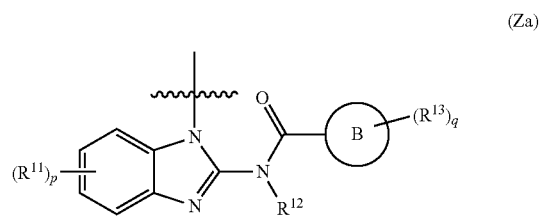

(Za)

wherein, ring B is selected from the group consisting of cycloalkyl, heterocyclyl, aryl and heteroaryl;

$R^8$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^9$ and $R^{10}$ are identical or different, and each is independently selected from the group consisting of hydrogen, alkyl, —C(O)O-benzyl, haloalkyl, cycloalkyl, heterocyclyl, aryl and heteroaryl;

$R^{11}$ each is identical or different, and each is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl;

$R^{12}$ is selected from the group consisting of hydrogen, alkyl, alkenyl and alkynyl;

$R^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^{14}$ and $R^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, hydroxy, cyano, nitro, alkyl, alkoxy, cycloalkyl, heterocyclyl, aryl and heteroaryl;

n is 0, 1, 2, 3 or 4;
m is 0, 1 or 2;
s is integer of 1 to 6;
p is 0, 1, 2, 3 or 4; and
q is 0, 1, 2, 3 or 4.

24. A compound of formula (IIIB), or a tautomer, or a pharmaceutically acceptable salt thereof:

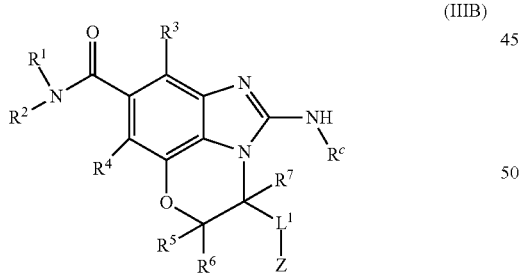

(IIIB)

wherein:
$R^c$ is selected from the group consisting of hydrogen, alkyl, haloalkyl, alkenyl and alkynyl;

$R^1$ and $R^2$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, alkyl, alkoxy, haloalkyl, amino, nitro, cyano, hydroxy, hydroxyalkyl, cycloalkyl, heterocyclyl, aryl and heteroaryl;

$R^3$ and $R^4$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$R^5$, $R^6$ and $R^7$ are identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl;

$L^1$ is selected from the group consisting of alkylene, alkenylene, NH, —(CH$_2$)$_s$NH—, O, S(O)$_m$, C(O), —C(O)NH—, —NHC(O)— or —HNC(O)NH—, wherein the alkylene or alkenylene is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl; two substitutes on the same carbon can form a cycloalkyl or heterocyclyl ring; two substitutes on adjacent carbons can form a cycloalkyl, heterocyclyl, aryl and heteroaryl ring;
or $L^1$ is absent;

Z is selected from the group consisting of —C(O)O-benzyl, butyloxy carbonyl, hydrogen, halogen, alkyl, alkenyl, alkynyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, —NR$^9$R$^{10}$, cycloalkyl, heterocyclyl, aryl and heteroaryl;
or Z is selected from a formula (Za) or a tautomer:

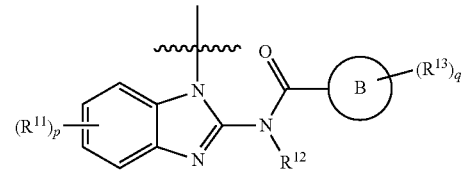

(Za)

wherein, ring B is selected from the group consisting of cycloalkyl, heterocyclyl, aryl and heteroaryl;

$R^9$ and $R^{10}$ are identical or different, and each is independently selected from the group consisting of hydrogen, alkyl, —C(O)O-benzyl, haloalkyl, cycloalkyl, heterocyclyl, aryl and heteroaryl;

$R^{11}$ each is identical or different, and each is independently selected from the group consisting of hydrogen, halogen, alkyl, alkoxy, haloalkyl, amino, nitro, hydroxy, hydroxyalkyl, cyano, —C(O)NR$^{14}$R$^{15}$, cycloalkyl, heterocyclyl, aryl and heteroaryl;

$R^{12}$ is selected from the group consisting of hydrogen, alkyl, alkenyl and alkynyl;

$R^{13}$ each is identical or different, and each is independently selected from the group consisting of hydrogen, halogen, alkyl, alkoxy, haloalkyl, amino, nitro, hydroxy, hydroxyalkyl, cyano, cycloalkyl, heterocyclyl, aryl and heteroaryl, wherein the alkyl, alkoxy, cycloalkyl, heterocyclyl, aryl or heteroaryl is unsubstituted or substituted with one or more substituents selected from the group consisting of halogen, alkyl, alkoxy, haloalkyl, amino, nitro, hydroxy, hydroxyalkyl, cyano, cycloalkyl, heterocyclyl, aryl and heteroaryl;

$R^{14}$ and $R^{15}$ are identical or different, and each is independently selected from the group consisting of hydrogen, alkyl, haloalkyl, cycloalkyl, heterocyclyl, aryl and heteroaryl; wherein the alkyl, cycloalkyl, heterocyclyl, aryl or heteroaryl is unsubstituted or substituted with one or more substituents selected from the group consisting of halogen, hydroxy, cyano, nitro, alkyl, alkoxy, cycloalkyl, heterocyclyl, aryl and heteroaryl;

m is 0, 1 or 2;
s is integer of 1 to 6;
p is 0, 1, 2, 3 or 4; and
q is 0, 1, 2, 3 or 4.

25. A process of preparing the compound of formula (I) according to claim 1, or a tautomer, or a pharmaceutically acceptable salt thereof, comprising a step of:

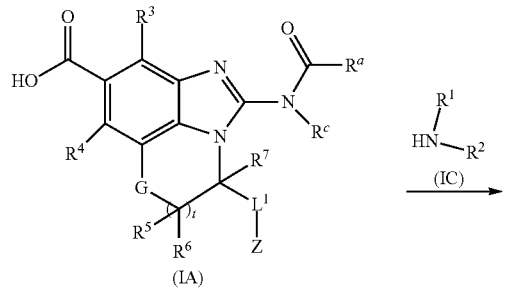
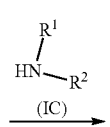
(IA)
(IC)

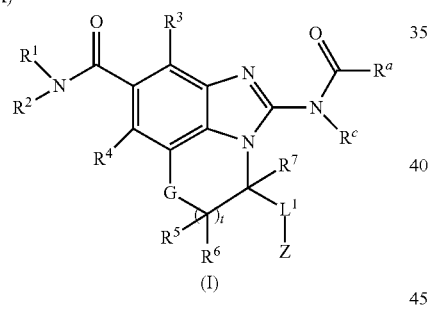
(I)

reacting a compound of formula (IA) with a compound of formula (IC) to obtain the compound of formula (I); wherein G, t, $R^a$, $R^c$, $R^1$, $R^2$, $R^3$, $R^4$, $R^5$, $R^6$, $R^7$, $L^1$ and Z are each as defined in claim 1.

26. A process of preparing the compound of formula (D) according to claim 1, or a tautomer, or a pharmaceutically acceptable salt thereof, comprising a step of:

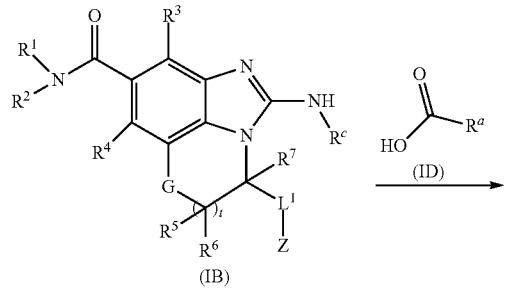
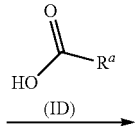
(IB)
(ID)

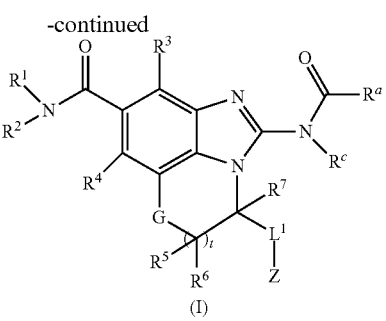
(I)

reacting a compound of formula (IB) with a compound of formula (ID) to obtain the compound of formula (I); wherein G, t, $R^a$, $R^c$, $R^1$, $R^2$, $R^3$, $R^4$, $R^5$, $R^6$, $R^7$, $L^1$ and Z are each as defined in claim 1.

27. A process of preparing the compound of formula (III) according to claim 3, or a tautomer, or a pharmaceutically acceptable salt thereof, comprising a step of:

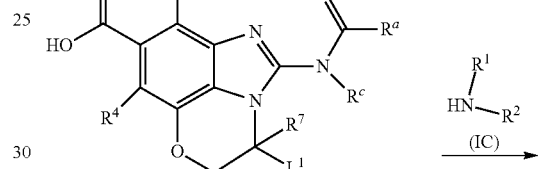
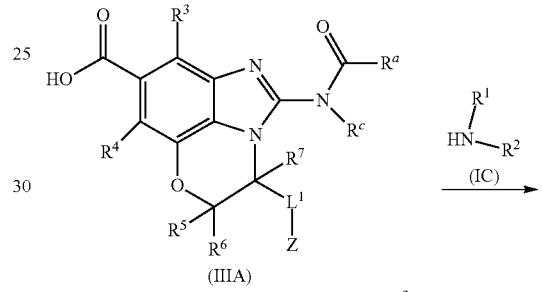
(IIIA)
(IC)

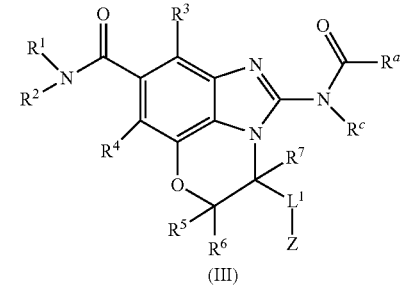
(III)

reacting a compound of formula (IA) with a compound of formula (IC) to obtain the compound of formula (I); wherein $R^a$, $R^c$, $R^1$, $R^2$, $R^3$, $R^4$, $R^5$, $R^6$, $R^7$, $L^1$ and Z are each as defined in claim 3.

28. A process of preparing the compound of formula (III) according to claim 3, or a tautomer, or a pharmaceutically acceptable salt thereof, comprising a step of:

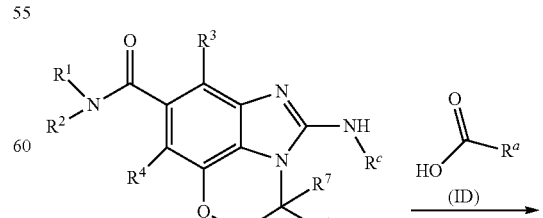
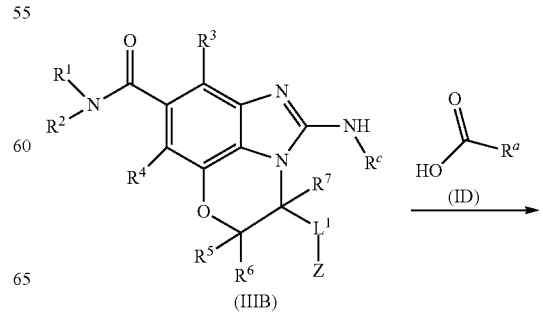
(IIIB)
(ID)

-continued

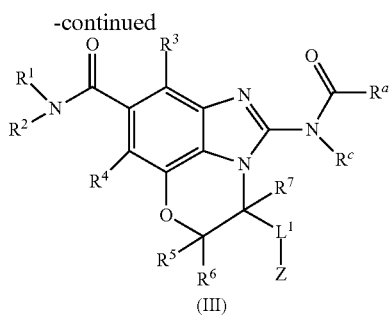

(III)

reacting a compound of formula (IIIB) with a compound of formula (ID) to obtain the compound of formula (III);

wherein $R^a$, $R^c$, $R^1$, $R^2$, $R^3$, $R^4$, $R^5$, $R^6$, $R^7$, $L^1$ and Z are each as defined in claim 3.

29. A pharmaceutical composition comprising a therapeutically effective amount of a compound, or a tautomer, or a pharmaceutically acceptable salt thereof according to claim 1, and one or more pharmaceutically acceptable carriers, diluents or other excipients.

30. A method for treating a disease in which modulation of STING is beneficial, wherein the disease is selected from the group consisting of hepatitis B virus (HBV), hepatitis C virus (HCV), influenza, human immunodeficiency virus infection, AIDS, and as immunogenic composition or vaccine adjuvants, the method comprising administering to a subject in need thereof a therapeutically effective amount of a compound, or a tautomer, or a pharmaceutically acceptable salt thereof according to claim 1.

31. A method for treating a STING-mediated disease or disorder, wherein the disease or disorder is viral infections, the method comprising a step of administering to a subject in need thereof a therapeutically effective amount of a compound, or a tautomer, or a pharmaceutically acceptable salt thereof according to claim 1.

32. The compound of formula (I), or a tautomer, or a pharmaceutically acceptable salt thereof, according to claim 13, wherein $L^1$ is selected from the group consisting of alkylene and alkenylene, wherein the alkylene or alkenylene is unsubstituted or substituted with one or more hydroxyl.

33. The compound of formula (I), or a tautomer, or a pharmaceutically acceptable salt thereof, according to claim 1, wherein ring A is selected from the group consisting of pyrazolyl or imidazolyl, and/or ring B is selected from the group consisting of pyrazolyl or imidazolyl.

* * * * *